(12) United States Patent
Saha et al.

(10) Patent No.: US 11,439,669 B2
(45) Date of Patent: *Sep. 13, 2022

(54) C. NOVYI FOR THE TREATMENT OF SOLID TUMORS IN HUMANS

(71) Applicants: BIOMED VALLEY DISCOVERIES, INC., Kansas City, NY (US); THE JOHNS HOPKINS UNIVERSITY, Baltimore, MD (US)

(72) Inventors: Saurabh Saha, Wellesley Hills, MA (US); Shibin Zhou, Owings Mills, MD (US); Bert Vogelstein, Baltimore, MD (US); Kenneth W. Kinzler, Bel Air, MD (US)

(73) Assignees: BIOMED VALLEY DISCOVERIES, INC., Kansas City, MO (US); THE JOHNS HOPKINS UNIVERSITY, Baltimore, MD (US)

( * ) Notice: Subject to any disclaimer, the term of this patent is extended or adjusted under 35 U.S.C. 154(b) by 151 days.

This patent is subject to a terminal disclaimer.

(21) Appl. No.: 16/836,003

(22) Filed: Mar. 31, 2020

(65) Prior Publication Data

US 2020/0330525 A1 Oct. 22, 2020

Related U.S. Application Data

(63) Continuation of application No. 14/781,273, filed as application No. PCT/US2014/032196 on Mar. 28, 2014, now Pat. No. 10,617,723.

(60) Provisional application No. 61/806,497, filed on Mar. 29, 2013.

(51) Int. Cl.
| | |
|---|---|
| *A61K 35/74* | (2015.01) |
| *A61K 35/742* | (2015.01) |
| *A61K 31/65* | (2006.01) |
| *A61K 45/06* | (2006.01) |
| *A61N 5/10* | (2006.01) |
| *A61K 35/00* | (2006.01) |

(52) U.S. Cl.
CPC .............. *A61K 35/74* (2013.01); *A61K 31/65* (2013.01); *A61K 35/742* (2013.01); *A61K 45/06* (2013.01); *A61N 5/10* (2013.01); *A61K 2035/11* (2013.01)

(58) Field of Classification Search
CPC ...... A61K 35/74; A61K 31/65; A61K 35/742; A61K 45/06; A61K 2035/11; A61N 5/10
USPC ...................................................... 424/93.41
See application file for complete search history.

(56) References Cited

U.S. PATENT DOCUMENTS

| | | |
|---|---|---|
| 4,599,331 A | 7/1986 | Schreiber et al. |
| 4,771,042 A | 9/1988 | Braughler et al. |
| 6,905,480 B2 | 6/2005 | McGuckin, Jr. et al. |
| 7,331,947 B2 | 2/2008 | McGuckin, Jr. et al. |
| 7,344,710 B2 | 3/2008 | Dang et al. |
| 2005/0079157 A1 | 4/2005 | Dang et al. |
| 2010/0034814 A1 | 2/2010 | Sabbadini |

FOREIGN PATENT DOCUMENTS

| | | |
|---|---|---|
| EP | 20021236471 A2 | 9/2002 |
| EP | 1675465 B1 | 3/2010 |
| WO | 1987002672 | 5/1987 |
| WO | 1990015816 | 12/1990 |
| WO | 2003045153 A1 | 6/2003 |
| WO | 2005018332 A1 | 3/2005 |
| WO | 2008073148 A2 | 6/2008 |

OTHER PUBLICATIONS

Kim et al., "Atypical radiological features of a leiomyosarcoma that arose from the ovarian vein and mimicked a vascular tumor," The British Journal of Radiology, 83 (2010), e95-e97.
Dunn et al., "Disseminated Osteomyelitis Caused by Clostridium novyi in a Cat," Case Report, Can Vet J, 24 (1983) 312-315.
OB-GYN 101 Pharmacy, "Antibiotics of Choice," Available Online at: www.brooksidepress.org/Products/OBGYN101/MyDocuments4/Pharmacy/AntibioticsofChoice.htm, at least as early as Dec. 18, 2005 per Internet Archive Wayback Machine.
Korman et al., "Checkpoint Blockade in Cancer Immunotherapy," Adv Immunol, 90 (2006), 297-339.
Tourneau, et al. "Dose Escalation Methods in Phase I Cancer Clinial Trials," J Natl Cancer Inst. 10:708:720.
EP Appin. No. 14774988.1 Office Action dated Aug. 2018.
Krick E.L. et al. "Evaluation of Clostridium novyi-NT spores in dogs with naturally occurring tumors," Am J Vet Res. Jan. 2012;73(1):112-8.

(Continued)

*Primary Examiner* — Jennifer M. H. Tichy

(74) *Attorney, Agent, or Firm* — Bryan Cave Leighton Paisner LLP

(57) ABSTRACT

The present invention provides, inter alia, methods for treating or ameliorating an effect of a solid tumor present in a human. These methods include administering intratumorally to the human a unit dose of *C. novyi*, preferably *C. novyi* NT, colony forming units (CFUs), which contains about $1 \times 10^3$-$1 \times 10^7$ CFUs suspended in a pharmaceutically acceptable carrier or solution. Methods for debulking a solid tumor present in a human, methods for ablating a solid tumor present in a human, a method for microscopically precise excision of tumor cells in a human, methods for treating or ameliorating an effect of a solid tumor that has metastasized to one or more sites in a human, unit doses of *C. novyi*, preferably *C. novyi* NT, CFUs, and kits for treating or ameliorating an effect of a solid tumor present in a human are also provided.

45 Claims, 44 Drawing Sheets

Figure 1A:
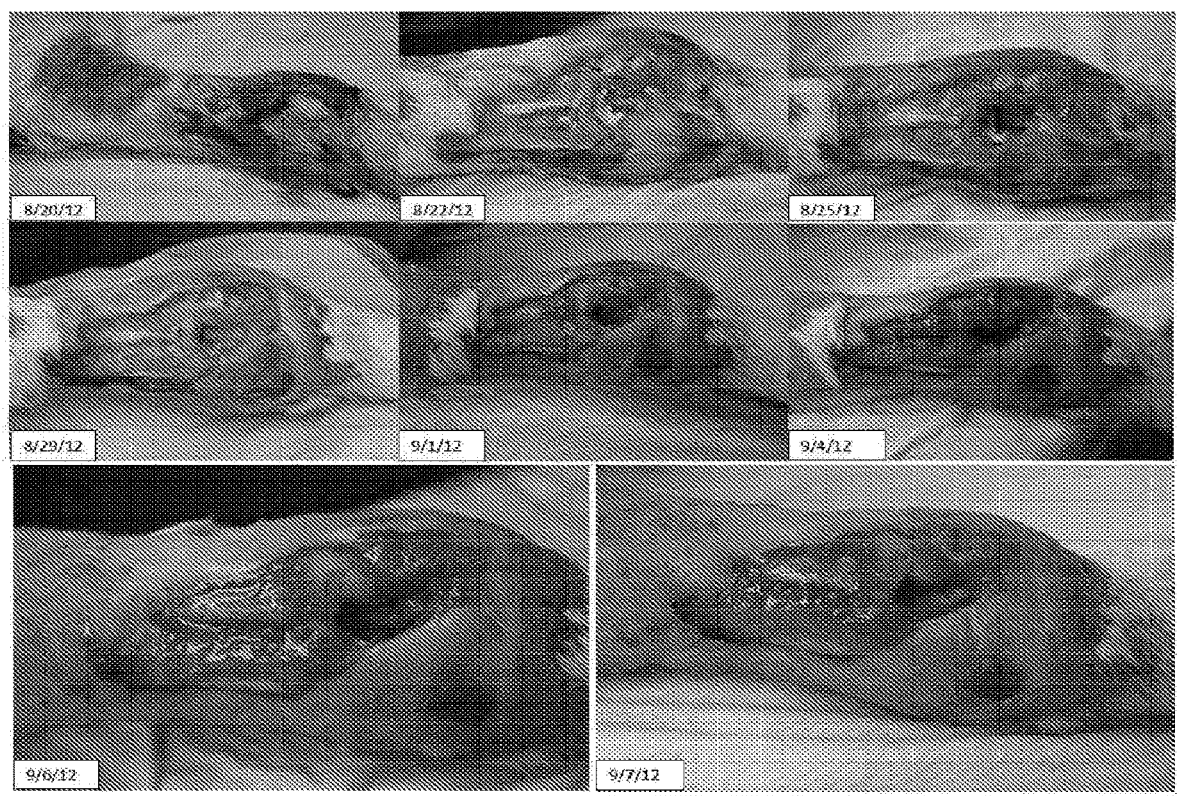

Specification includes a Sequence Listing.

(56) References Cited

OTHER PUBLICATIONS

Pawelek et al. "Bacteria as tumour-targeting vectors". The lancet oncology. Sep. 30, 2003;4(9):548-56.

Mose, J.R., "Clostridium Strain M55 and its effectson Malignant Tumors," In Bacteries anaerobies 1st edn (ed. Fredette, V.) 229-247, Montreal Institute e Microbiologie et Hygiene de Universite de Montreal, 1967.

Mose, J.R. Onkolyse durch Clostridien in 3rd International Congress of Chemotherapy (ed.) Thieme, G., 1972, Stuttgurt, Germany.

Komeda, et al., "A Third Mode of DNA Binding: Phosphate Clamps by a Polynuclear Platinum Complex," J. Am. Chem. Soc., 2006, 128 (50), pp. 16092-16103.

Senderowitz, A.M., et al., "Information needed to conduct first-in human oncology trials in the U.S.: a view from a former FDA medical reviewer," Clin. Cancer. Res. 2010, 16: 1719-25.

Qu, et al., "Synthesis and DNA conformational changes of non-covalent polynuclear platinum complexes," J. Inorg. Biochem. Oct. 2004;98(10):1591-98.

Kleinman, et al., "Sequence- and target-independent angiogenesis suppression by siRNA via TLR3," Nature. Apr. 3, 2008; 452(7187): 591-597.

Makrides, S.C., 1998. "Strategies for optimizing heterologous protein expression in *Escherichia coli*." Trends Biotechnol. 16: 54-60.

Maurer, T., "Small-molecule ligands bind to a distinct pocket in Ras and inhibit SOS-mediated nucleotide excange activity," PNAS 109(14): 5299-304 (2012).

Shima, et al., "In silica discovery of small-molecule Ras inhibitors that display antitumor activity by blocking the Ras-affector interaction," Proc Natl Arad Sci U S A, 110(20):8182-7 (2013).

Patgirl, et al., "An Orthosteric inhibitor of the Ras-Sos interaction", Na. Chem. Biol. 7:585-587 (2011).

Remington, The Science and practice of pharmacy, 21 Ed., Lippincott Williams and Wilkins, Philadelphia, PA.

The National Formulary, American Pharmaceutical Association, Washington, DC.

Dennis, et al., "Prognostic Factors for Cutaneous and Subcutaneous Soft Tissue Sarcomas in Dogs," The American College of Veterinary Pathologists, 2011,48(1), pp. 73-84.

Van Mellaert, et al., (2006) Clostridium spores as anti-tumour agents. Trends Microbial 14:190-196.

Harris, et al., "Synthesis, Characterization, and Cytotoxicity of a Novel Highly Charged Trinuclear Platinum Compound. Enhancement of Cellular Uptake with Charge," Inarg Chem., 2005, 44 (26), pp. 9598-9600.

International Search Report dated Aug. 25, 2014.

Agrawal, et al. "Bacteriolytic therapy can generate a potent immune response against experimental tumors," Proc Natl Acad Sci USA 101, 15172-7 (2004).

Bai, et al. "V. Antiparasitic mebendazole shows survival benefit in 2 preclinical models of glioblastoma multiforme," Neuro-oncology 13, 974-982 (2011).

Barretina, et al. "Subtype-specific genomic alterations define new targets for soft-tissue sarcoma therapy," Nature genetics 42,715-721 (2010).

Bettegowda, et al. "The genome and transcriptomes of the anti-tumor agent Clostridium novyi-NT," Nature biotechnology 24, 1573-1580 (2006).

Bettegowda, C., & Saha, S. "Clostridium novyi-NT Cancer Therapeutic," Chordoma Foundation. Mar. 22, 2013.

Bettegowada, et al. "Overcoming the hypoxic barrier to radiation therapy with anaerobic bacteria," Proc Natl Acad Sci U S A. Dec. 9, 2003; 100(25): 15083-15088.

Breed, et al. "The No. of Colonies Allowable on Satisfactory Agar Plates". Journal of Bacteriology 1 (3): 321-331 (1916).

Brook, I. "Anaerobic infections in children," Microbes Infect. Oct. 2002;4(12):1271-80.

Carey, et al. "Clostridial oncolysis in man," Eur. J. Cancer 3, 37-46 (1967).

Chmielecki, et al. "Whole-exome sequencing identifies a recurrent NAB2-STAT6 fusion in solitary fibrous tumors," Nature genetics 45, 131-132 (2013).

Dang, et al. "Targeting Vascular and Avascular Compartments of Tumors with C. novyi-NT and Anti-Microtubule Agents," Cancer Biol Ther 3, 326-37 (2004).

Dang, et al., "Combination bacteriolytic therapy for the treatment of experimental tumors." PNAS. vol. 98, pp. 15155-15160 (2001).

Diaz, et al. "Pharmacologic and toxicologic evaluation of C. novyi-NT spores," Toxicol Sci 88, 562-75 (2005).

European Medicines Agency, Combined VeDDRA list of clinical terms for reporting suspected adverse reactions in animals and humans to veterinary medicinal products (2012).

Gavhane, et al., "Solid Tumors: Facts, Challenges and Solutions." International J. of Pharma Science and Research, vol. 2, pp. 1-12 (2011).

International Search Report for PCT/US2014/032196, dated Aug. 25, 2014.

Jain, et al. "Can engineered bacteria help control cancer?" Proc Natl Acad Sci U S A 98,14748-50 (2001).

Jones, et al. "Frequent mutations of chromatin remodeling gene ARID1A in ovarian clear cell carcinoma," Science 330, 228-231 (2010).

Joseph, et al. "Exomic Analysis of myxoid liposarcomas, synovial sarcomas and osteosarcomas," Genes Chromosomes Cancer. Jan. 2014;53(1):15-24.

Lee, et al. "A remarkably simple genome underlies highly malignant pediatric rhabdoid cancers," J Clin Invest. Aug. 2012;122(8):2983-8.

Leu, et al. "Laboratory and clinical evidence of synergistic cytotoxicity of sequential treatment with gemcitabine followed by docetaxel in the treatment of sarcoma," J Clin Oncol. May 1, 2004,22(9):1706-12.

Nemunaitis, et al. "Pilot trial of genetically modified, attenuated *Salmonella* expressing the *E. coli* cytosine deaminase gene in refractory cancer patients," Cancer Gene Ther. Oct. 2003;10(10):737-44.

Nicolson, et al. "Gulf War illnesses: complex medical, scientific and political paradox," Med Confl Surviv. Apr.-Jun. 1998;14(2):156-65.

Paoloni, et al. "Translation of new cancer treatments from pet dogs to humans," Nature Reviews Cancer 8, 147-156 (2008).

Parker, et al. "Effect of histolyticus infection and toxin on transplantable mouse tumors," Proc. Soc. Exp. Biol. Med. 66, 461 (1947).

Patnaik, et al. "Canine cutaneous mast cell tumor: morphologic grading and survival time in 83 dogs," Veterinary pathology 21, 469-474 (1984).

Roberts, et al. "Intratumoral injection of Clostridium novyi-NT spores induces antitumor responses," Sci Transl Med. Aug. 13, 2014;6(249):249ra111.

Sabattini, et al. "Histologic Grading of Canine Mast Cell Tumor: Is 2 Better Than 3?," Vet Pathol. Jan. 2015;52(1):70-3.

Schlom "Recent advances in therapeutic cancer vaccines," Cancer Biother Radiopharm. Feb. 2012;27(1):2-5.

Smedley, et al. "Prognostic markers for canine melanocytic neoplasms: a comparative review of the literature and goals for future investigation," Veterinary pathology 48, 54-72 (2011).

Vail, et al. "Spontaneously occurring tumors of companion animals as models for human cancer," Cancer investigation 18, 781-792 (2000).

Van Mellaert, et al. "Clostridium spores as anti-tumour agents," Trends Microbiol. Apr. 2006;14(4):190-6.

Veterinary Co-operative Oncology Group Veterinary Co-operative Oncology Group—Common Terminology Criteria for Adverse Events (VCOG-CTCAE) following chemotherapy or biological antineoplastic therapy in dogs and cats v1.0. Veterinary and comparative oncology 2, 195-213 (2004).

Vogelstein, et al. "Cancer genome landscapes," Science 339, 1546-1558 (2013).

Walther, et al. "Novel jet-injection technology for nonviral intratumoral gene transfer in patients with melanoma and breast cancer," Clin Cancer Res. Nov. 15, 2008;14(22):7545-53.

(56) References Cited

OTHER PUBLICATIONS

Written Opinion of the International Searching Authority for PCT/US2014/032196, dated Aug. 25, 2014.
Roberts, et al. "Intratumoral injection of Clostridium novyi-NT spores induces antitumor responses," Sci Transl Med. Aug. 13, 2014;6(249):249r3111.
Written Opinion of the International Searching Authority for PCT/U82014/032196, dated Aug. 25, 2014.

Figure 5

| | | 04-R03 | 16-R03 | 16-R02 | 11-R04 | 11-R02 |
|---|---|---|---|---|---|---|
| Sample Characteristics | | | | | | |
| | Tumor Type | STS | STS | STS | STS | STS-PNST |
| | Tumor Location | Left antebrachium | Left forepaw | Left thigh | Right forepaw | Left stifle |
| | Sample Type | FFPE | FFPE | FFPE | FFPE | FFPE |
| | Sample Acquisition | Pre-study initiation | Pre-study initiation | Post-study initiation | Pre-study initiation | Pre-study initiation |
| | Pathological Tumor Purity | 90% | 70% | 70% | 70% | 80% |
| | Mutation based Tumor Purity | 71% | 37% | 41% | 51% | 45% |
| | Source of normal DNA | Blood | Blood | Blood | Blood | Blood |
| Analysis Characteristics | | | | | | |
| | Analysis type | Next-generation sequencing | Next-generation sequencing | Next-generation sequencing | Next-generation sequencing | Next-generation sequencing |
| | Enrichment approach | In solution DNA capture | In solution DNA capture | In solution DNA capture | In solution DNA capture | In solution DNA capture |
| | Genome regions analyzed | 30,194 coding genes | 30,194 coding genes | 30,194 coding genes | 30,194 coding genes | 30,194 coding genes |
| | Bases sequenced | 32,893,252 bases | 32,893,252 bases | 32,893,252 bases | 32,893,252 bases | 32,893,252 bases |
| | Sequence Read Length | 100 bp | 100 bp | 100 bp | 100 bp | 100 bp |
| Somatic Tumor-Specific Alterations | | | | | | |
| | Number of somatic sequence alterations identified | 8 | 2 | 4 | 3 | 14 |
| | Number of somatic copy number alterations identified | 2 | 0 | 0 | 0 | 17 |
| Overall Statistics (Tumor) | | | | | | |
| | Sequenced Bases Mapped to Genome | 14,429,862,200 | 21,425,345,200 | 12,124,067,000 | 19,196,019,800 | 15,780,857,820 |
| | Sequenced Bases Mapped to Target Regions | 6,089,590,437 | 9,789,715,947 | 4,858,071,422 | 11,459,270,433 | 10,233,153,813 |
| | Fraction of Sequenced Bases Mapped to Target Regions | 42% | 46% | 40% | 60% | 65% |
| | Bases in target regions with at least 10 reads | 36,537,164 | 37,343,313 | 36,043,139 | 50,430,237 | 48,966,409 |
| | Fraction of bases in target regions with at least 10 reads | 92% | 94% | 91% | 94% | 91% |
| Overall Statistics (Normal) | | | | | | |
| | Sequenced Bases Mapped to Genome | 13,693,458,500 | 14,561,175,800 | 17,329,903,700 | 15,677,511,300 | 14,950,236,100 |
| | Sequenced Bases Mapped to Target Regions | 7,318,085,121 | 5,586,179,511 | 6,882,015,752 | 8,201,336,539 | 7,394,567,092 |
| | Fraction of Sequenced Bases Mapped to Target Regions | 37% | 38% | 40% | 52% | 49% |
| | Bases in target regions with at least 10 reads | 37,102,993 | 36,602,585 | 38,229,451 | 50,263,991 | 50,057,763 |
| | Fraction of bases in target regions with at least 10 reads | 93% | 92% | 96% | 93% | 93% |
| Sequence Reads at Each Base (Tumor) | | | | | | |
| | Average Number of Total High Quality Sequences at Each Base | 138 | 227 | 110 | 190 | 172 |
| | Average Number of Distinct High Quality Sequences at Each Base | 114 | 202 | 99 | 160 | 127 |
| Sequence Reads at Each Base (Normal) | | | | | | |
| | Average Number of Total High Quality Sequences at Each Base | 178 | 137 | 168 | 145 | 130 |
| | Average Number of Distinct High Quality Sequences at Each Base | 149 | 121 | 152 | 127 | 112 |
| Tumor/Normal Matching | | | | | | |
| | Germline SNPs present | 9,204 | 13,895 | 15,138 | 16,454 | 12,407 |
| | Percent T/N Matching | 100% | 100% | 100% | 100% | 100% |
| Summary Data | | | | | | |
| | Mutations/Mb | 0.24 | 0.06 | 0.12 | 0.09 | 0.43 |
| | CNAs/Mb | 0.06 | 0.00 | 0.00 | 0.00 | 0.52 |

STS - soft tissue sarcoma; STS-PNST - soft tissue sarcoma, peripheral nerve sheath tumor; OSA - chondroblastic osteosarcoma; T - tumor; N - normal; Mb - megabase; CNAs - copy number alterations; SNPs - single nucleotide polymorphisms; FFPE - formalin fixed paraffin embedded; NA -

Figure 5 (Con't)

| | 11-R01 | 04-R08 | 04-R02 | 04-R01 | 01-R02 | 04-R04 | Min | Max | Average | |
|---|---|---|---|---|---|---|---|---|---|---|
| | STS-PNST | STS-PNST | STS-PNST | STS-PNST | STS-PNST | OSA | | | | |
| | Left pinna | Right hindpaw | Right Metacarpus | Right mid maxillary area | Left thoracic flank | Right humerus | | | | |
| | FFPE | FFPE | FFPE | FFPE | FFPE | FFPE | | | NA | |
| | Post-study initiation | Post-study initiation | Pre-study initiation | Pre-study initiation | Pre-study initiation | Pre-study initiation | | | NA | |
| | 90% | 90% | 90% | 80% | 80% | 90% | 70% | 90% | 83% | |
| | 54% | 67% | 69% | NA | 29% | 65% | 29% | 71% | 57% | |
| | Blood | Blood | Blood | Blood | Blood | Blood | NA | NA | NA | |
| | Next-generation sequencing | Next-generation sequencing | Next-generation sequencing | Next-generation sequencing | Next-generation sequencing | Next-generation sequencing | | | | |
| | In solution DNA capture | In solution DNA capture | In solution DNA capture | In solution DNA capture | In solution DNA capture | In solution DNA capture | | | | |
| | 30,194 coding genes | 30,194 coding genes | 30,194 coding genes | 30,194 coding genes | 30,194 coding genes | 30,194 coding genes | NA | NA | NA | |
| | 32,893,252 bases | 32,893,252 bases | 32,893,252 bases | 32,893,252 bases | 32,893,252 bases | 32,893,252 bases | NA | NA | NA | |
| | 100 bp | 100 bp | 100 bp | 100 bp | 100 bp | 100 bp | NA | NA | NA | |
| | 4 | 55 | 6 | 0 | 20 | 14 | 0 | 95 | 16 | STS only |
| | 0 | 0 | 0 | 0 | 9 | 4 | 0 | 17 | 3 | STS only |
| | 19,163,476,700 | 8,055,248,900 | 19,418,702,600 | 23,322,445,500 | 9,336,883,200 | 10,439,082,100 | 8,055,248,900 | 23,322,445,500 | 15,629,271,909 | |
| | 8,571,289,371 | 3,317,956,697 | 8,491,584,341 | 9,068,570,137 | 3,967,568,909 | 4,609,328,923 | 3,317,956,697 | 11,459,770,433 | 7,314,196,403 | |
| | 45% | 41% | 44% | 39% | 42% | 44% | 38.9% | 64.8% | 46.2% | |
| | 37,167,238 | 35,180,875 | 37,503,866 | 36,941,231 | 36,056,022 | 36,426,112 | 35,180,875 | 50,430,237 | 38,972,328 | |
| | 94% | 89% | 93% | 93% | 91% | 92% | 88.5% | 94.4% | 92.1% | |
| | 16,042,663,700 | 16,931,763,000 | 15,728,989,700 | 16,150,073,600 | 15,151,630,300 | 18,183,947,700 | 14,561,175,800 | 19,693,458,500 | 16,391,943,309 | |
| | 6,245,786,511 | 6,370,965,466 | 6,167,005,020 | 6,222,256,939 | 5,777,414,557 | 6,883,542,265 | 5,586,793,511 | 8,201,336,539 | 6,640,832,434 | |
| | 39% | 38% | 39% | 38% | 38% | 38% | 37.2% | 52.3% | 40.7% | |
| | 37,018,789 | 37,230,015 | 37,216,686 | 37,236,461 | 37,246,921 | 37,128,882 | 36,602,585 | 50,263,991 | 39,575,867 | |
| | 93% | 94% | 94% | 94% | 94% | 93% | 92.1% | 95.2% | 93.5% | |
| | 195 | 73 | 190 | 201 | 84 | 104 | 73 | 227 | 153 | |
| | 174 | 67 | 159 | 170 | 59 | 79 | 59 | 202 | 128 | |
| | 154 | 152 | 150 | 152 | 140 | 166 | 130 | 178 | 152 | |
| | 125 | 130 | 127 | 133 | 120 | 143 | 112 | 152 | 131 | |
| | 14,801 | 12,953 | 14,163 | 14,502 | 9,828 | 11,861 | 8,204 | 16,454 | 13,110 | |
| | 100% | 100% | 100% | 100% | 100% | 100% | 100% | 100% | 100% | |
| | 0.12 | 2.89 | 0.18 | 0.00 | 0.61 | 0.43 | 0.00 | 2.89 | 0.47 | |
| | 0.00 | 0.00 | 0.00 | 0.00 | 0.27 | 0.12 | 0.00 | 0.52 | 0.09 | |

Figure 6

| Case ID | Tumor Type | Gene Symbol | Gene Description | Gene Accession | Nucleotide Position (Genomic) | Fold amplification | Mutation type |
|---|---|---|---|---|---|---|---|
| 04-R03 | STS | AIG1 | androgen-induced 1 | ENSCAFG00000000303 | chr1:37686977-37687647 | 3.2 | Amplification |
| | | NKAIN1 | Na+/K+ transporting ATPase interacting 1 | ENSCAFG00000011175 | chr2:72699008-72705959 | 3.1 | Amplification |
| | | PIK3C2B | phosphatidylinositol-4-phosphate 3-kinase, catalytic subunit type 2 beta | ENSCAFG00000009661 | chr38:4011051-4013492 | 10.2 | Amplification |
| | | MDM4 | Mdm4 p53 binding protein homolog | ENSCAFG00000009669 | chr38:4055972-4103319 | 12.3 | Amplification |
| | | LRRN2 | leucine rich repeat neuronal 2 | ENSCAFG00000009675 | chr38:4164479-4166666 | 4.1 | Amplification |
| | | NFASC | neurofascin | ENSCAFG00000009901 | chr38:4474563-4542491 | 9.2 | Amplification |
| | | CNTN2 | contactin 2 (axonal) | ENSCAFG00000024609 | chr38:4576761-4596329 | 7.3 | Amplification |
| | | TMEM81 | transmembrane protein 81 | ENSCAFG00000009956 | chr38:4604335-4605118 | 10.0 | Amplification |
| | | RBP5 | retinoblastoma binding protein 5 | ENSCAFG00000009970 | chr38:4608590-4634589 | 11.4 | Amplification |
| | | DUSTY_CANFA | dual serine/threonine and tyrosine protein kinase | ENSCAFG00000009999 | chr38:4669577-4715897 | 11.3 | Amplification |
| 11-R02 | STS-PNST | TMCC2 | transmembrane and coiled-coil domain family 2 | ENSCAFG00000010030 | chr38:4734043-4773669 | 5.8 | Amplification |
| | | NUAK2 | NUAK family, SNF1-like kinase, 2 | ENSCAFG00000010038 | chr38:4798849-4816487 | 7.6 | Amplification |
| | | KLHDC8A | kelch domain containing 8A | ENSCAFG00000010046 | chr38:4833445-4838372 | 6.7 | Amplification |
| | | LEMD1 | LEM domain containing 1 | ENSCAFG00000025208 | chr38:4872059-4896801 | 10.4 | Amplification |
| | | CDK18 | cyclin-dependent kinase 18 | ENSCAFG00000010082 | chr38:4993764-5001820 | 7.7 | Amplification |
| | | Novel Gene | uncharacterized protein | ENSCAFG00000010106 | chr38:5028755-5029725 | 6.2 | Amplification |
| | | MFSD4 | major facilitator superfamily domain containing 4 | ENSCAFG00000010137 | chr38:5037069-5063455 | 7.6 | Amplification |
| | | ELK4 | ELK4, ETS-domain protein (SRF accessory protein 1) | ENSCAFG00000010144 | chr38:5077862-5083778 | 11.7 | Amplification |
| | | SLC45A3 | solute carrier family 45, member 3 | ENSCAFG00000010148 | chr38:5111400-5116718 | 5.8 | Amplification |
| | | PGBD5 | piggyBac transposable element derived 5 | ENSCAFG00000012098 | chr4:11983074-12023545 | 6.3 | Amplification |
| 04-R04 | OSA_c | DLG5 | discs, large homolog 5 (Drosophila) | ENSCAFG00000015499 | chr4:30898933-31016619 | 5.4 | Amplification |
| | | MAT1A | methionine adenosyltransferase I, alpha | ENSCAFG00000015807 | chr4:32662979-32676594 | 5.3 | Amplification |
| | | Novel gene | uncharacterized protein | ENSCAFG00000015098 | chr20:47978916-47984829 | 5.3 | Amplification |
| | | AIG1 | androgen-induced 1 | ENSCAFG00000000303 | chr1:37686977-37687647 | 5.7 | Amplification |
| | | XM_844172.1 | uncharacterized protein | ENSCAFG00000023337 | chr2:7738782-7751246 | 5.9 | Amplification |
| | | Novel gene | uncharacterized protein | ENSCAFG00000024028 | chr3:40494283-40494577 | 6.4 | Amplification |
| | | SIX3 | SIX homeobox 3 | ENSCAFG00000025547 | chr10:50465860-50469140 | 5.3 | Amplification |
| 01-R02 | STS-PNST | LST1 | leukocyte specific transcript 1 | ENSCAFG00000023691 | chr12:4088376-4089275 | 6.7 | Amplification |
| | | FAM9A | family with sequence similarity 9A, member A | ENSCAFG00000003647 | chr17:13630517-13631423 | 5.0 | Amplification |
| | | TLX2 | T-cell leukemia homeobox 2 | ENSCAFG00000008415 | chr17:51694813-51696234 | 5.1 | Amplification |
| | | SOX3 | SRY (sex determining region Y)-box 3 | ENSCAFG00000019026 | chrX:113431902-113463234 | 5.6 | Amplification |
| | | Novel gene | uncharacterized protein | ENSCAFG00000019588 | chrX:125230197-125231662 | 5.3 | Amplification |

STS - soft tissue sarcoma; STS-PNST - soft tissue sarcoma, peripheral nerve sheath tumor; OSA_c - chondroblastic osteosarcoma.

C. NOVYI FOR THE TREATMENT OF SOLID TUMORS IN HUMANS

CROSS-REFERENCE TO RELATED APPLICATIONS

This application is a continuation application of U.S. application Ser. No. 14/781,273, filed Sep. 29, 2015, which is a U.S. National Stage Application of International Application No. PCT/US2014/032196, filed Mar. 28, 2014, which claims benefit to U.S. Provisional Application No. 61/806,497 filed Mar. 29, 2013. The entire contents of the above applications are incorporated by reference as if recited in full herein.

GOVERNMENT FUNDING

This invention was made with government support under CA062924 awarded by the National Institutes of Health. The government has certain rights in the invention.

FIELD OF INVENTION

The present invention provides, inter alia, methods for treating or ameliorating an effect of a solid tumor present in a human, for debulking a solid tumor present in a human, for microscopically precise excising of tumor cells in a human, and for ablating a solid tumor present in a human. Unit doses of C. novyi CFUs and kits are also provided.

INCORPORATION BY REFERENCE OF SEQUENCE LISTING

This application contains references to amino acids and/or nucleic acid sequences that have been filed as sequence listing text file "1065272-000591-seq.txt", file size of 44 KB, created on Jun. 18, 2020. The aforementioned sequence listing is hereby incorporated by reference in its entirety pursuant to 37 C.F.R. § 1.52(e)(5).

BACKGROUND OF THE INVENTION

Strategies that successfully target and destroy human cancers recognize differences between normal and malignant tissues (Dang et al., 2001). Such differences can be found at the molecular level, as is the case with genetic aberrations, or more holistically, as with the physiological aberrations in a tumor.

It is known that malignant solid tumors are usually composed of a necrotic core and a viable rim. Therapeutic interventions to date have focused on the well-vascularized outer shell of the tumor, but few have targeted the inner hypoxic core (Jain et al., 2001). The inner core of a tumor has unique characteristics that differentiate it from normal tissues. The core has a poor vascular supply and is therefore deficient in nutrients and oxygen. As a site of active cellular necrosis, the lack of a functional vascular supply limits the clearance of noxious cell breakdown and results in a low pH. Such an environment is not suitable for growth of most human cells but is a rich environment for the growth of certain anaerobic bacteria. More than sixty-years ago, this concept led investigators to inject spores of *Clostridium histolyticus* into tumor-bearing animals (Parker et al., 1947). Remarkably, the bacteria germinated only in the necrotic core of the tumor and liquefied the tumors. In the 1950s and 1960s, spores from *Clostridium butyricum* were injected into patients with a variety of very advanced solid tumor malignancies (Mose, 1967; Mose, 1972). Many patients had significant germination and destruction of large portions of their tumors, but the very poor health and advanced stage of these patients made their clinical management difficult and the absence of complete clinical responses subdued further pursuit of this approach.

Successful treatment of solid tumors remains an unfulfilled medical goal. Accordingly, there is a need to find treatments for solid tumors. The present invention is directed to meeting this and other needs.

SUMMARY OF THE INVENTION

One embodiment of the present invention is a method for treating or ameliorating an effect of a solid tumor present in a human. This method comprises administering intratumorally to the human a unit dose of C. novyi colony forming units (CFUs) comprising about $1 \times 10^3$-$1 \times 10^7$ CFUs suspended in a pharmaceutically acceptable carrier or solution.

Another embodiment of the present invention is a method for debulking a solid tumor present in a human. This method comprises administering intratumorally to the human a unit dose of C. novyi CFUs comprising about $1 \times 10^3$-$1 \times 10^7$ CFUs suspended in a pharmaceutically acceptable carrier or solution.

An additional embodiment of the present invention is a method for debulking a solid tumor present in a human. This method comprises administering intratumorally to the human one to four cycles of a unit dose of C. novyi NT spores comprising about $1 \times 10^4$ spores per cycle, each unit dose of C. novyi NT being suspended in a pharmaceutically acceptable carrier or solution.

A further embodiment of the present invention is a method for treating or ameliorating an effect of a solid tumor present in a human. This method comprises administering intratumorally to the human one to four cycles of a unit dose of C. novyi NT spores comprising about $1 \times 10^4$ spores per cycle, each unit dose of C. novyi NT spores being suspended in a pharmaceutically acceptable carrier or solution.

Another embodiment of the present invention is method for ablating a solid tumor present in a human. This method comprises administering intratumorally to the human a unit dose of C. novyi CFUs comprising about $1 \times 10^3$-$1 \times 10^7$ CFUs suspended in a pharmaceutically acceptable carrier or solution, wherein the tumor is ablated leaving a margin of normal tissue.

A further embodiment of the present invention is a unit dose of C. novyi CFUs. This unit dose comprises about $1 \times 10^3$-$1 \times 10^7$ CFUs in a pharmaceutically acceptable carrier or solution, which is effective for treating or ameliorating an effect of a solid tumor present in a human.

An additional embodiment of the present invention is a kit for treating or ameliorating an effect of a solid tumor present in a human. This kit comprises a unit dose of C. novyi CFUs comprising about $1 \times 10^3$-$1 \times 10^7$ CFUs in a pharmaceutically acceptable carrier or solution and instructions for use of the kit.

Another embodiment of the present invention is a method for microscopically precise excision of tumor cells in a human. This method comprises administering intratumorally to the human a unit dose of C. novyi NT colony forming units (CFUs) comprising about $1 \times 10^3$-$1 \times 10^7$ CFUs suspended in a pharmaceutically acceptable carrier or solution.

A further embodiment of the present invention is a method for treating or ameliorating an effect of a solid tumor that has metastasized to one or more sites in a human. This method comprises administering intratumorally to the human a unit dose of *C. novyi* NT colony forming units (CFUs) comprising at least about $1\times10^3$-$1\times10^7$ CFUs suspended in a pharmaceutically acceptable carrier or solution.

BRIEF DESCRIPTION OF THE DRAWINGS

FIGS. 1A-B show various images of canine osteosarcomas on the right distal radius/ulna of test subjects "Sasha" (FIG. 1A) and "Sampson" (FIG. 1B) after radiation treatment and intravenous (IV) *C. novyi* NT injection.

FIG. 2A shows Kaplan-Meier curves showing survival of F433 Fisher rats after orthotopic implantation of a syngeneic glioma cell line (F98). Outer line—*C. novyi*-NT spores injected into tumor 12-15 days after tumor implantation. Inner line—control. FIG. 2B shows bioluminescence (Xenogen imaging system) in three representative F433 Fisher rats after orthotopic implantation of F98 glioma cell line. Images acquired on day 0 (pretreatment—day of *C. novyi*—NT spore injection), day 1 after IT injection of *C. novyi*-NT spores, and day 2 after IT injection of *C. novyi*-NT spores. FIG. 2C shows luciferase activity (count in millions) on day 0 (pretreatment), day 1 after IT injection of *C. novyi*-NT spores, and day 2 after IT injection of *C. novyi*-NT spores.

FIGS. 3A-B and 4A-B show germinated *C. novyi*-NT bacteria within microscopic brain tumor lesions. In these Figures, gram stain showed vegetative *C. novyi*-NT bacteria (white or black arrowheads) localized in tumor (T) and stellate micro-invasion (S), but not in normal brain tissue (Br). FIG. 3A is a 100× magnification showing the interface of tumor and normal brain. FIG. 3B is a 400× magnification showing the interface of tumor and normal brain. FIG. 4A is a 100× magnification showing the interface of normal brain, tumor, and stellate micro-invasion of neoplastic tissue. FIG. 4B is a 400× magnification showing *C. novyi*-NT germination in a stellate micro-invasive lesion.

FIG. 5 is a table of summary data for samples sequenced.

FIG. 6 is a table of copy number alterations in canine sarcomas.

FIGS. 7A-F are photographic and CT images from dog 11-R01 showing a partial response to *C. novyi*-NT therapy. Images span pre-treatment to day 70 after first IT dose of *C. novyi*-NT spores. FIG. 7A shows a pre-treatment image of the peripheral nerve sheath tumor. FIG. 7B shows abscess formation on day 3 of the study, with extent confined to tumor. FIG. 7C shows medical debridement following spontaneous abscess rupture and discharge of necrotic and purulent material, which allowed healing by second intention. FIG. 7D shows that the wound has healed completely by day 70 of the study and 77.6% reduction in tumor longest diameter was noted. FIG. 7E is a pre-treatment CT image, taken 4 days before first treatment, which shows extent of tumor (circle) at the intersection of pinna and cranium. FIG. 7F is a post-treatment CT image on day 10 of the study showing almost complete de-bulking of tumor.

FIGS. 8A-D are photographic and CT images from dog 04-R03 showing a complete response to *C. novyi*-NT therapy. Images span pre-treatment to day 60 after first IT dose of *C. novyi*-NT spores. FIG. 8A shows a pre-treatment image of the soft tissue sarcoma. FIG. 8B shows a tumor localized abscess formed on day 15 of the study, 1 day after a third dose of *C. novyi*-NT spores. FIG. 8C shows that tumor de-bulking was complete by day 27 of the study and healthy granulation tissue had formed. FIG. 8D shows that the wound had healed completely by day 60 of the study, and no residual tumor was noted (complete response). FIG. 8E is a pre-treatment CT image, taken 5 days before first treatment, showing extent of tumor (circle) on antebrachium. FIG. 8F is a post-treatment CT image on day 62 of the study showing complete loss of tumor mass.

FIG. 9 shows the size of dog 11-R01's tumor from initial IT dosing of *C. novyi* NT spores to completion of the clinical course.

FIG. 10A shows photographic (upper panels) and CT images (lower panels) of a canine soft tissue sarcoma on test subject "Drake" (04-R01) after IT dosing of *C. novyi* NT spores. Circled regions of the CT images indicate tumor location. FIG. 10B shows the size of Drake's tumor from initial IT dosing of *C. novyi* NT, through three subsequent doses, to completion of the clinical course.

FIG. 11 shows the size of dog 04-R03's tumor from initial IT dosing of *C. novyi* NT spores, through two subsequent cycles, to completion of the clinical course.

FIG. 12A shows tumor size in eight test subjects (11-R02, 04-R02, 26-R01, 16-R02, 04-R05, 16-R03, 11-R04, and 04-R06) over the clinical course in which four cycles of IT *C. novyi* NT spores were administered. FIG. 12B shows tumor size in three test subjects (04-R08, 01-R02, and 10-R02) for which data from a complete clinical course was not available due to necessary amputation or data cutoff.

FIG. 13 shows an injection scheme for tumors treated in the IT study disclosed in Examples 6 and 7.

FIGS. 14A-D show CT and MRI images from a human patient. FIG. 14A shows a post-treatment CT with contrast on day 3 demonstrating evidence of intra- and extra-medullary air collection. FIG. 14B shows a pre-treatment MRI (T1 with gadolinium contrast) of the right upper humerus showing a contrast enhancing mass involving the soft tissue and possibly adjacent bone. FIG. 14C shows a post-treatment MRI on day 4 demonstrating diminished contrast enhancement in the tumor mass compared to baseline. FIG. 14D shows a post-treatment MRI on day 29 showing homogenous non-enhancing mass consistent with ongoing necrosis. Tumor is highlighted with arrowheads.

FIGS. 15A-D show extensive tumor necrosis in the human patient treated with *C. novyi*-NT spores. FIGS. 15A and 15B show a pre-treatment tumor biopsy showing viable tumor (leiomyosarcoma) cells, 40× (A) and 100× (B) magnification, respectively. FIGS. 15C and 15D show a post-treatment tumor biopsy, 4 days after IT injection of *C. novyi*-NT spores, showing extensive necrosis of tumor cells, 40× (A) and 100× (B) magnification, respectively.

FIGS. 16A-D show various aspects of the IT injection procedure using a three-tined needle. FIG. 16A shows a photograph of the three-tined needle. FIGS. 16B and 16C show computed tomography (CT) images of the target injection area before and after insertion of the needle. FIG. 16D shows a magnified image of the three tines of the needle. FIG. 16E shows a CT image with overlaying measurements for determining insertion points of the needle.

DETAILED DESCRIPTION OF THE INVENTION

One embodiment of the present invention is a method for treating or ameliorating an effect of a solid tumor present in a human. This method comprises administering intratumorally to the human a unit dose of *C. novyi* colony forming units (CFUs) comprising about $1\times10^3$-$1\times10^7$ CFUs suspended in a pharmaceutically acceptable carrier or solution.

As used herein, the terms "treat," "treating," "treatment" and grammatical variations thereof mean subjecting an individual subject (e.g., a human patient) to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, a "solid tumor" means an abnormal mass of cell growth. Solid tumors may occur anywhere in the body. Solid tumors may be cancerous (malignant) or non-cancerous (benign). Examples of solid tumors according to the present invention include adrenocortical carcinoma, anal tumor/cancer, bladder tumor/cancer, bone tumor/cancer (such as osteosarcoma), brain tumor, breast tumor/cancer, carcinoid tumor, carcinoma, cervical tumor/cancer, colon tumor/cancer, endometrial tumor/cancer, esophageal tumor/cancer, extrahepatic bile duct tumor/cancer, Ewing family of tumors, extracranial germ cell tumor, eye tumor/cancer, gallbladder tumor/cancer, gastric tumor/cancer, germ cell tumor, gestational trophoblastic tumor, head and neck tumor/cancer, hypopharyngeal tumor/cancer, islet cell carcinoma, kidney tumor/cancer, laryngeal tumor/cancer, leiomyosarcoma, leukemia, lip and oral cavity tumor/cancer, liver tumor/cancer (such as hepatocellular carcinoma), lung tumor/cancer, lymphoma, malignant mesothelioma, Merkel cell carcinoma, mycosis fungoides, myelodysplastic syndrome, myeloproliferative disorders, nasopharyngeal tumor/cancer, neuroblastoma, oral tumor/cancer, oropharyngeal tumor/cancer, osteosarcoma, ovarian epithelial tumor/cancer, ovarian germ cell tumor, pancreatic tumor/cancer, paranasal sinus and nasal cavity tumor/cancer, parathyroid tumor/cancer, penile tumor/cancer, pituitary tumor/cancer, plasma cell neoplasm, prostate tumor/cancer, rhabdomyosarcoma, rectal tumor/cancer, renal cell tumor/cancer, transitional cell tumor/cancer of the renal pelvis and ureter, salivary gland tumor/cancer, Sezary syndrome, skin tumors (such as cutaneous t-cell lymphoma, Kaposi's sarcoma, mast cell tumor, and melanoma), small intestine tumor/cancer, soft tissue sarcoma, stomach tumor/cancer, testicular tumor/cancer, thymoma, thyroid tumor/cancer, urethral tumor/cancer, uterine tumor/cancer, vaginal tumor/cancer, vulvar tumor/cancer, and Wilms' tumor. Preferably, the solid tumor is selected from the group consisting of soft tissue sarcoma, hepatocellular carcinoma, breast cancer, pancreatic cancer, and melanoma. More preferably, the solid tumor is a leiomyosarcoma, such as a retroperitoneal leiomyosarcoma.

As used herein, a "unit dose" means the amount of a medication administered to a subject, e.g., a human, in a single dose.

As used herein, "C. novyi" means a bacteria belonging to species of Clostridium novyi or a bacteria derived therefrom. Clostridium novyi, which may be obtained commercially from, e.g., the ATCC (#19402), is a gram-positive anaerobic bacterium. A bacterium derived from Clostridium novyi may be made by, e.g., screening native Clostridium novyi for clones that possess specific characteristics. Preferred C. novyi bacteria are those which are non-toxic or minimally toxic to a subject such as a mammal, e.g., a human. For example, a preferred C. novyi, C. novyi NT, is a bacteria derived from native Clostridium novyi that has lost its single systemic toxin ($\alpha$-toxin) gene by, e.g., a genetic engineering process or through a selection procedure. C. novyi NT may be made, for example, using the procedure disclosed in Dang et al., 2001 and U.S. Pat. No. 7,344,710. Thus, the present invention includes C. novyi as well as C. novyi NT bacteria.

Pharmacokinetic studies indicate that C. novyi NT spores, if injected intravenously, are rapidly cleared from the circulation (greater than 99% spores are cleared within 1 hour) and sequestered within the reticulo-endothelial system. Long-term distribution studies reveal that these spores are eventually eliminated from all tissues within one year. Delivered in spore form (dormant stage), C. novyi NT germinates (transitions from the spore to the vegetative state) when exposed to the hypoxic regions of tumors. Thus, the toxicities of C. novyi NT are expected to be greater in tumor-bearing than in healthy patients.

Healthy mice and rabbits showed no apparent clinical signs (morbidity, mortality, or clinical appearance) of toxicity regardless of treatment dose when injected with C. novyi NT intravenously. However, examination of tissues at necropsy revealed both gross and microscopic inflammatory changes that appeared to be treatment-dose dependent. These findings, primarily in the liver, spleen and adrenals, were noted at doses of $5\times10^8$ spores/kg or greater. Healthy animals receiving lower doses showed no gross or microscopic abnormalities at necropsy. In animals that received high doses, resolution of inflammation was already evident on day 28 and all signs of inflammation were absent in all animals by one year following administration. To determine if C. novyi NT spores would germinate in non-tumor hypoxic tissue, studies in elderly mice with atherosclerotic plaques and experimental myocardial infarctions were treated with C. novyi NT. There was no evidence of spore localization or germination within these vascular lesions. At the conclusion of the study, no clinical or pathologic abnormalities (other than the pre-existing cardiovascular lesions) were noted in these mice. These studies demonstrated that C. novyi NT caused no apparent clinical and minimal pathological toxicity in healthy animals.

Intravenous (IV) injection of spores into immune-competent tumor-bearing mice leads to lysis of the tumor and an intense inflammatory response. In mice, one of three outcomes is typically observed: One subset (25-35%) of mice are cured (no tumor recurrence after one year of observation) and develop long-term immunity to the original tumor (Agrawal et al., 2004). Another subset (65-75%) experience complete clinical responses, but undergo a recurrence with re-growth of the original tumor. Finally, the remaining subset (0 to 20%, depending on the experiment) undergoes tumor destruction, but develop significant clinical toxicity 2-5 days after the initiation of therapy. Relatively simple measures, such as hydration, are adequate to reduce this toxicity, often entirely eliminating these signs. Studies in larger animals (rabbits) show the same cure and recurrence rates with C. novyi NT therapy, but do not show the life-threatening clinical toxicity observed in a subset of mice. Treatment-related death was observed in tumor-bearing mice, but not in rabbits, treated with C. novyi NT spores (Diaz et al., 2005). In these studies toxicity was related to both spore dose and tumor size. In moribund mice, no specific clinical laboratory or pathologic end-organ damage was noted and the only significant finding was hepatosplenomegaly. Cured mice had rare remnant inflammatory changes in the liver and spleen, but were otherwise no different than untreated animals. These studies show that toxicity in tumor-bearing animals can be pronounced (death)

in mice with large tumors, but was minimal in larger animals (rabbits), and was manageable in mice with hydration or antibiotics.

Previous work using *C. novyi* NT spores injected intravenously ($1 \times 10^9$ spores/m$^2$) as a single agent in tumor bearing dogs produced no life threatening toxicities. The dogs were maintained on fluid therapy (2-4 ml/kg/hr) for several days post treatment which may have decreased the toxicity. Unfortunately, there were no measurable tumor responses to the treatment.

As used herein, "colony forming units" ("CFUs") mean viable forms of the bacteria which will give rise to an aggregate of cells (or colonies). Such viable forms include vegetative and spore forms, and the present invention includes both forms used separately and in combination. Colony forming unit assays are known in the art. See, e.g., Breed et al., 1916. Media for supporting the growth of *C. novyi* are commercially available, such as Reinforced Clostridial Medium (RCM) from Difco (BD, Franklin Lakes, N.J.). As set forth above, the unit dose comprises from about $1\times10^3$-$1\times10^7$, such as about $1\times10^3$-$1\times10^4$, about $1\times10^4$-$1\times10^5$, about $1\times10^5$-$1\times10^6$, or about $1\times10^6$-$1\times10^7$, *C. novyi* CFUs.

In one aspect of this embodiment, the unit dose comprises from about $1\times10^6$-$1\times10^7$ *C. novyi* CFUs. In another aspect of this embodiment, the unit dose comprises about $1\times10^4$ *C. novyi* CFUs. Surprisingly, the doses disclosed herein for human treatment are unexpectedly lower than would be expected from simply extrapolating from our non-rodent models using ⅙ of the non-rodent highest non-severely toxic does (HNSTD), as is typical for a starting dose therapeutic for oncology indications. See, e.g., Senderowicz, A. M., "Information needed to conduct first-in human oncology trials in the United States: a view from a former FDA medical reviewer." Clin. Canc. Res., 2010, 16:1719-25.

Preferably, in the present invention the *C. novyi* is *C. novyi* NT.

In another aspect of this embodiment, the unit dose comprises about $1\times10^6$-$1\times10^7$ *C. novyi* NT spores. In a further aspect of this embodiment, the unit dose comprises about $1\times10^4$ *C. novyi* NT spores.

In an additional aspect of this embodiment, the administering step comprises injecting the unit dose at a single location into the tumor. In another aspect of this embodiment, the administering step comprises injecting the unit dose at multiple unique locations, such as 2, 3, 4, 5, 6, 7, 8, 9, 10 or more than 10 unique locations, into the tumor. Preferably, the administering step comprises injecting the unit dose at 1-5 unique locations into the tumor, such as in the configurations shown in FIG. 13. In another preferred embodiment, the administering step comprises injecting the unit dose at 5 or more unique locations into the tumor. Multi-site injections may be carried out as disclosed herein, preferably with a multi-tined needle such as Quadra-Fuse® (Rex-Medical, Conshohocken, Pa.). In the present invention, the administering step, as noted above, includes injections directly into the tumor, but other methods for administering an active agent, such as *C. novyi* or *C. novyi* NT, to a tumor are also contemplated. Such methods include implantation, transdermal delivery, and transmucosal delivery.

In another aspect of this embodiment, the method further comprises administering a plurality of treatment cycles, such as 1, 2, 3, 4, 5, 6, 7, 8, 9, 10, 11, 12, 13, 14, 15, 20, 25, 30, or more than 30 cycles, to the human, each treatment cycle comprising injecting one unit dose of the *C. novyi* CFUs, such as one unit dose of the *C. novyi* NT spores, into the solid tumor. Preferably, 1-10 treatment cycles are administered. More preferably, 2-4 treatment cycles are administered. The interval between each treatment cycle may be variable. In one preferred embodiment, the interval between each treatment cycle is about 5-100 days. In another preferred embodiment, the interval between each treatment cycle is about 7 days.

In an additional aspect of this embodiment, the method further comprises administering intravenous (IV) fluids to the human before, during, and/or after each administration of the *C. novyi* CFUs, such as the *C. novyi* NT spores. IV fluids for hydrating the patients are disclosed herein and are well known in the art. Such fluids may be fluids that are isotonic with blood, such as, e.g., a 0.9% sodium chloride solution, or Lactated Ringer's solution.

In another aspect of this embodiment, the method further comprises providing the human with a first course of antibiotics for a period of time and at a dosage that is effective to treat or alleviate an adverse side effect caused by the *C. novyi* CFUs, such as the *C. novyi* NT spores. In the present invention an adverse side effect (or adverse event, which is used interchangeably with adverse side effect) may include but is not limited to infections (such as those caused by open wounds), vomiting, hematochezia, and fever.

In one preferred embodiment, the antibiotics are administered for two weeks post *C. novyi* administration. Non-limiting examples of such antibiotics include amoxicillin, clavulanate, metronidazole, and combinations thereof.

In another preferred embodiment, the method further comprises providing the human with a second course of antibiotics for a period of time and at a dosage that is effective to treat or alleviate an adverse side effect caused by the *C. novyi*. The second course of antibiotics may be initiated after completion of the first course of antibiotics and is carried out for 1-6 months, such as 3 months. Preferably, the antibiotic used in the second course is doxycycline, but any antibiotic approved by a medical professional may be used.

In a further aspect of this embodiment, the method further comprises, using a co-treatment protocol by, e.g., administering to the human a therapy selected from the group consisting of chemotherapy, radiation therapy, immunotherapy, and combinations thereof.

The *C. novyi*, e.g., the *C. novyi* NT spores, and the anti-cancer agent(s) used in the co-treatment therapy may be administered to the human, either simultaneously or at different times, as deemed most appropriate by a physician. If the *C. novyi*, e.g., the *C. novyi* NT spores, and the other anti-cancer agent(s) are administered at different times, for example, by serial administration, then the *C. novyi*, e.g., the *C. novyi* NT spores, may be administered to the human before the other anti-cancer agent. Alternatively, the other anti-cancer agent(s) may be administered to the human before the *C. novyi*, e.g., the *C. novyi* NT spores.

As used herein, "chemotherapy" means any therapeutic regimen that is compatible with the *C. novyi*, e.g., *C. novyi* NT, treatment of the present invention and that uses cytotoxic and/or cytostatic agents against cancer cells or cells that are associated with or support cancer cells. In a preferred embodiment, the chemotherapy comprises administering to the human an agent selected from the group consisting of an anti-metabolite, a microtubule inhibitor, a DNA damaging agent, an antibiotic, an anti-angiogenesis agent, a vascular disrupting agent, a molecularly targeted agent, and combinations thereof.

As used herein, an "anti-metabolite" is a substance that reduces or inhibits a cell's use of a chemical that is part of normal metabolism. Non-limiting examples of anti-metabolite agents or analogs thereof according to the present invention include antifolates, purine inhibitors, pyrimidine inhibitors, and combinations thereof.

As used herein, an "antifolate" is a substance that alters, reduces, or inhibits the use of folic acid (vitamin $B_9$) by cells. Non-limiting examples of antifolates include methotrexate (DuraMed Pharmaceuticals, Inc.), pemetrexed (Eli Lilly), pralatrexate (Spectrum Pharmaceuticals), aminopterin (Sigma Aldrich), pharmaceutically acceptable salts thereof, and combinations thereof.

As used herein, a "purine" is a compound that contains a fused six-membered and a five-membered nitrogen-containing ring. Non-limiting examples of purines that are important for cellular metabolism include adenine, guanine, hypoxanthine, and xanthine. A "purine inhibitor" is a substance that alters, reduces or suppresses the production of a purine or the use of a purine by a cell. Non-limiting examples of purine inhibitors include methotrexate (DuraMed Pharmaceuticals, Inc.), pemetrexed (Eli Lilly), hydroxyurea (Bristol-Myers Squibb), 2-mercaptopurine (Sigma-Aldrich), 6-mercaptopurine (Sigma-Aldrich), fludarabine (Ben Venue Laboratories), clofarabine (Genzyme Corp.), nelarabine (GlaxoSmithKline), pralatrexate (Spectrum Pharmaceuticals), 6-thioguanine (Gate Pharmaceuticals), forodesine (BioCryst Pharmaceuticals), pentostatin (Bedford Laboratories), sapacitabine (Cyclacel Pharmaceuticals, Inc.), aminopterin (Sigma Aldrich), azathioprine (GlaxoSmithKline), pharmaceutically acceptable salts thereof, and combinations thereof.

As used herein, a "pyrimidine" is a compound that contains a six-membered nitrogen-containing ring. Non-limiting examples of pyrimidines that are important for cellular metabolism include uracil, thymine, cytosine, and orotic acid. A "pyrimidine inhibitor" is a substance that alters, reduces, or suppresses the production of a pyrimidine or the use of a pyrimidine by the a cell. Non-limiting examples of pyrimidine inhibitors include 5-fluorouracil (Tocris Bioscience), tegafur (LGM Pharma), capecitabine (Xeloda) (Roche), cladribine (LGM Pharma), gemcitabine (Eli Lilly), cytarabine (Bedford Laboratories), decitabine (Eisai Inc.), floxuridine (Bedford Laboratories), 5-azacytidine (Pharmion Pharmaceuticals), doxifluridine (Cayman Chemicals), thiarabine (Access Pharmaceuticals), troxacitabine (SGX Pharmaceuticals), raltitrexed (AstraZeneca), carmofur (Santa Cruz Biotechnology, Inc.), 6-azauracil (MP Biomedicals, LLC), pharmaceutically acceptable salts thereof, and combinations thereof.

In a preferred aspect of the present invention, the antimetabolite agent is selected from the group consisting of 5-fluorouracil (Tocris Bioscience), tegafur (LGM Pharma), capecitabine (Xeloda) (Roche), cladribine (LGM Pharma), methotrexate (DuraMed Pharmaceuticals, Inc.), pemetrexed (Eli Lilly), hydroxyurea (Bristol-Myers Squibb), 2-mercaptopurine (Sigma-Aldrich), 6-mercaptopurine (Sigma-Aldrich), fludarabine (Ben Venue Laboratories), gemcitabine (Eli Lilly), clofarabine (Genzyme Corp.), cytarabine (Bedford Laboratories), decitabine (Eisai Inc.), floxuridine (Bedford Laboratories), nelarabine (GlaxoSmithKline), pralatrexate (Spectrum Pharmaceuticals), 6-thioguanine (Gate Pharmaceuticals), 5-azacytidine (Pharmion Pharmaceuticals), doxifluridine (Cayman Chemicals), forodesine (BioCryst Pharmaceuticals), pentostatin (Bedford Laboratories), sapacitabine (Cyclacel Pharmaceuticals, Inc.), thiarabine (Access Pharmaceuticals), troxacitabine (SGX Pharmaceuticals), raltitrexed (AstraZeneca), aminopterin (Sigma Aldrich), carmofur (Santa Cruz Biotechnology, Inc.), azathioprine (GlaxoSmithKline), 6-azauracil (MP Biomedicals, LLC), pharmaceutically acceptable salts thereof, and combinations thereof.

As used herein, a "microtubule inhibitor" is a substance that disrupts the functioning of a microtubule, such as the polymerization or the depolymerization of individual microtubule units. In one aspect of the present invention, the microtubule inhibitor may be selected from the group consisting of a microtubule-destabilizing agent, a microtubule-stabilizing agent, and combinations thereof. A microtubule inhibitor of the present invention may also be selected from the group consisting of a taxane, a vinca alkaloid, an epothilone, and combinations thereof. Non-limiting examples of microtubule inhibitors according to the present invention include BT-062 (Biotest), HMN-214 (D. Western Therapeutics), eribulin mesylate (Eisai), vindesine (Eli Lilly), EC-1069 (Endocyte), EC-1456 (Endocyte), EC-531 (Endocyte), vintafolide (Endocyte), 2-methoxyestradiol (EntreMed), GTx-230 (GTx), trastuzumab emtansine (Hoffmann-La Roche), crolibulin (Immune Pharmaceuticals), D1302A-maytansinoid conjugates (ImmunoGen), IMGN-529 (ImmunoGen), lorvotuzumab mertansine (ImmunoGen), SAR-3419 (ImmunoGen), SAR-566658 (ImmunoGen), IMP-03138 (Impact Therapeutics), topotecan/vincristine combinations (LipoCure), BPH-8 (Molecular Discovery Systems), fosbretabulin tromethamine (OXiGENE), estramustine phosphate sodium (Pfizer), vincristine (Pierre Fabre), vinflunine (Pierre Fabre), vinorelbine (Pierre Fabre), RX-21101 (Rexahn), cabazitaxel (Sanofi), STA-9584 (Synta Pharmaceuticals), vinblastine, epothilone A, patupilone (Novartis), ixabepilone (Bristol-Myers Squibb), Epothilone D (Kosan Biosciences), paclitaxel (Bristol-Myers Squibb), docetaxel (Sanofi-Aventis), HAI abraxane, DJ-927 (Daiichi Sankyo), discodermolide (CAS No: 127943-53-7), eleutherobin (CAS No.: 174545-76-7), pharmaceutically acceptable salts thereof, and combinations thereof.

DNA damaging agents of the present invention include, but are not limited to, alkylating agents, platinum-based agents, intercalating agents, and inhibitors of DNA replication.

As used herein, an "alkylating agent" is a substance that adds one or more alkyl groups ($C_nH_m$, where n and m are integers) to a nucleic acid. In the present invention, an alkylating agent is selected from the group consisting of nitrogen mustards, nitrosoureas, alkyl sulfonates, triazines, ethylenimines, and combinations thereof. Non-limiting examples of nitrogen mustards include mechlorethamine (Lundbeck), chlorambucil (GlaxoSmithKline), cyclophosphamide (Mead Johnson Co.), bendamustine (Astellas), ifosfamide (Baxter International), melphalan (Ligand), melphalan flufenamide (Oncopeptides), and pharmaceutically acceptable salts thereof. Non-limiting examples of nitrosoureas include streptozocin (Teva), carmustine (Eisai), lomustine (Sanofi), and pharmaceutically acceptable salts thereof. Non-limiting examples of alkyl sulfonates include busulfan (Jazz Pharmaceuticals) and pharmaceutically acceptable salts thereof. Non-limiting examples of triazines include dacarbazine (Bayer), temozolomide (Cancer Research Technology), and pharmaceutically acceptable salts thereof. Non-limiting examples of ethylenimines include thiotepa (Bedford Laboratories), altretamine (MGI Pharma), and pharmaceutically acceptable salts thereof. Other alkylating agents include ProLindac (Access), Ac-225 BC-8 (Actinium Pharmaceuticals), ALF-2111 (Alfact Innovation), trofosfamide (Baxter International), MDX-1203 (Bristol-Myers Squibb), thioureidobutyronitrile (Cell- Ceutix), mitobronitol (Chinoin), mitolactol (Chinoin), nimustine (Daiichi Sankyo), glufosfamide (Eleison Pharmaceuticals), HuMax-TAC and PBD ADC combinations (Genmab), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1G cells and ifosfamide combinations (Nuvilex), estramustine phosphate (Pfizer), prednimustine (Pfizer), lurbinectedin (PharmaMar), trabectedin (PharmaMar), altreatamine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), and pharmaceutically acceptable salts thereof.

As used herein, a "platinum-based agent" is an anti-cancer substance that contains the metal platinum and analogs of such substances. The platinum may be in any oxidation state. Platinum-based agents of the present invention include, but are not limited to, 1,2-diaminocyclohexane (DACH) derivatives, phenanthroimidazole Pt(II) complexes, platiunum IV compounds, bi- and tri-nuclear platinum compounds, demethylcantharidin-integrated platinum complexes, platinum-conjugated compounds, cisplatin nanoparticles and polymer micelles, sterically hindered platinum complexes, oxaliplatin (Debiopharm), satraplatin (Johnson Matthey), BBR3464 (Novuspharma S.p.A.), ZD0473 (Astra Zeneca), cisplatin (Nippon Kayaku), JM-11 (Johnson Matthey), PAD (cis-dichlorobiscyclopentylamine platinum (II)), MBA ((trans-1, 2-diaminocyclohexane) bisbromoacetato platinum (II)), PHM ((1,2-Cyclohexanediamine) malonato platinum (II)), SHP ((1,2-Cyclohexanediamine) sulphato platinum (II)), neo-PHM ((trans-R,R-1,2-Cyclohexanediamine) malonato platinum (II)), neo-SHP ((trans-R,R-1,2-Cyclohexanediamine)sulphato platinum (II)), JM-82 (Johnson Matthey), PYP ((1,2-Cyclohexanediamine) bispyruvato platinum (II)), PHIC ((1,2-Cyclohexanediamine) isocitrato platinum (II)), TRK-710 ((trans-R,R-1,2-cyclohexanediamine) [3-Acetyl-5-methyl-2,4(3H,5H)-furandionato] platinum (II)), BOP ((1, 2-Cyclooctanediamine) bisbromoacetato platinum (II)), JM-40 (Johnson Matthey), enloplatin (UnionPharma), zeniplatin (LGM Pharma), CI-973 (Parke-Davis), lobaplatin (Zentaris AG/Hainan Tianwang International Pharmaceutical), cycloplatam (LGM Pharma), WA2114R (miboplatin/lobaplatin) (Chembest Research Laboratories, Ltd.), heptaplatin (SK12053R) (SK Chemicals), TNO-6 (spiroplatin) (Haihang Industry Co., Ltd.), ormaplatin (tetraplatin) (LGM Pharma), JM-9 (iproplatin) (Johnson Matthey), BBR3610 (Novuspharma S.p.A.), BBR3005 (Novuspharma S.p.A.), BBR3571 (Novuspharma S.p.A.), BBR3537 (Novuspharma S.p.A.), aroplatin (L-NDDP) (BOC Sciences), Pt-ACRAMTU ({[Pt(en) CI(ACRAMTU-S)](NO$_3$)$_2$(en=ethane-1, 2-diamine, ACRAMTU=1-[2-(acridin-9-ylamino)ethyl]-1, 3-dimethylthiourea)}), cisplatin-loaded liposomes (LiPlasomes), SPI-077 (Alza), lipoplatin (Regulon), lipoxal (Regulon), carboplatin (Johnson Matthey), nedaplatin (Shionogi Seiyaku), miriplatin hydrate (Dainippon Sumitomo Pharma), ormaplatin (LGM Pharma), enloplatin (Lederle Laboratories), C1973 (Parke-Davis), PEGylated cisplatin, PEGylated carboplatin, PEGylated oxaliplatin, transplatin (trans-diamminedichloroplatinum(II); mixedZ: trans-[PtCl$_2${Z—HN═C(OMe)Me}(NH$_3$)]), CD-37 (estradiol-platinum(II) hybrid molecule), picoplatin (Poniard Pharmaceuticals),

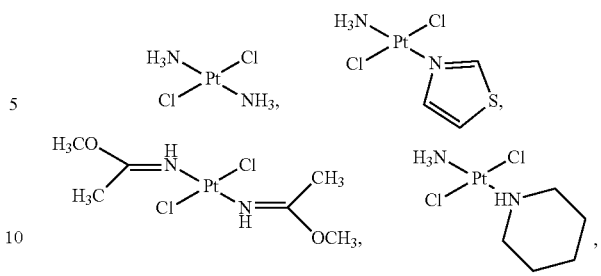

AH44 (Komeda et al., 2006; Harris et al., 2005; Qu et al., 2004), triplatinNC (Harris et al., 2005; Qu et al., 2004), ProLindac (Access), pharmaceutically acceptable salts thereof, and combinations thereof.

As used herein, an "intercalating agent" includes, but is not limited to, doxorubicin (Adriamycin), daunorubicin, idarubicin, mitoxantrone, pharmaceutically acceptable salts thereof, prodrugs, and combinations thereof.

Non-limiting examples of inhibitors of DNA replication include, but are not limited to topoisomerase inhibitors. As used herein, a "topoisomerase inhibitor" is a substance that decreases the expression or the activity of a topoisomerase. The topoisomerase inhibitors according to the present invention may inhibit topoisomerase I, topoisomerase II, or both topoisomerase I and topoisomerase II. Non-limiting examples of topoisomerase I inhibitors according to the present invention include irinotecan (Alchemia), APH-0804 (Aphios), camptothecin (Aphios), cositecan (BioNumerik), topotecan (GlaxoSmithKline), belotecan hydrochloride (Chon Kun Dang), firtecan pegol (Enzon), HN-30181A (Hanmi), hRS7-SN-38 (Immunomedics), labetuzumab-SN-38 (Immunomedics), etirinotecan pegol (Nektar Therapeutics), NK-012 (Nippon Kayaku), SER-203 (Serina Therapeutics), simmitecan hydrochloride prodrug (Shanghai HaiHe Pharmaceuticals), gimatecan (Sigma-Tau), namitecan (Sigma-Tau), SN-38 (Supratek Pharma), TLC-388 hydrochloride (Taiwan Liposome Company), lamellarin D (PharmaMar), pharmaceutically acceptable salts thereof, and combinations thereof. Non-limiting examples of inhibitors of topoisomerase type II according to the present invention include Adva-27a (Advanomics), zoptarelin doxorubicin (Aeterna Zentaris), valrubicin (Anthra Pharmaceuticals), razoxane (AstraZeneca), doxorubicin (Avena Therapeutics), amsacrine (Bristol-Myers Squibb), etoposide phosphate (Bristol-Myers Squibb), etoposide (Novartis), dexrazoxane (Cancer Research Technology), cytarabine/daunorubicin combination (Celator Pharmaceuticals), CAP7.1 (CellAct Pharma), aldoxorubicin (CytRx), amrubicin hydrochloride (Dainippon Sumitomo Pharma), vosaroxin (Dainippon Sumitomo Pharma), daunorubicin (Gilead Sciences), milatuzumab/doxorubicin combination (Immunomedics), aclarubicin (Kyowa Hakko Kirin), mitoxantrone (Meda), pirarubicin (Meiji), epirubicin (Pfizer), teniposide (Novartis), F-14512 (Pierre Fabre), ellriptinium acetate (Sanofi), zorubicin (Sanofi), dexrazoxane (TopoTarget), sobuzoxane (Zenyaku Kogyo), idarubicin (Pfizer), HU-331 (Cayman Chemical), aurintricarboxylic acid (Sigma Aldrich), pharmaceutically acceptable salts thereof, and combinations thereof.

Chemotherapeutic antibiotics according to the present invention include, but are not limited to, actinomycin, anthracyclines, valrubicin, epirubicin, bleomycin, plicamycin, mitomycin, pharmaceutically acceptable salts thereof, prodrugs, and combinations thereof.

As used herein, the term "anti-angiogenesis agent" means any compound that prevents or delays nascent blood vessel formation from existing vessels. In the present invention, examples of anti-angiogenesis agents include, but are not limited to, pegaptanib, ranibizumab, bevacizumab (avastin), carboxyamidotriazole, TNP-470, CM101, IFN-α, IL-12, platelet factor 4, suramin, SU5416, thrombospondin, VEGFR antagonists, angiostatic steroids and heparin, cartilage-derived angiogenesis inhibitory factor, matrix metalloproteinase inhibitors, angiostatin, endostatin, 2-methoxyestradiol, tecogalan, prolactin, $\alpha_v\beta_3$ inhibitors, linomide, VEGF-Trap, aminosterols, cortisone, tyrosine kinase inhibitors, anti-angiogenic siRNA, inhibitors of the complement system, vascular disrupting agents, and combinations thereof. Preferably, the anti-angiogenesis agent is bevacizumab.

VEGFR antagonists of the present invention include, but are not limited to, pazopanib, regorafenib, lenvatinib, sorafenib, sunitinib, axitinib, vandetanib, cabozantinib, vatalanib, semaxanib, ZD6474, SU6668, AG-013736, AZD2171, AEE788, MF1/MC-18F1, DC101/IMC-1C11, ramucirumab, and motesanib. VEGFR antagonists may also include, VEGF inhibitors such as bevacizumab, aflibercept, 2C3, r84, VEGF-Trap, and ranibizumab.

Angiostatic steroids of the present invention include any steroid that inhibits, attenuates, prevents angiogenesis or neovascularization, or causes regression of pathological vascularization. Angiostatic steroids of the present invention include those disclosed in European Patent Application Serial No. EP1236471 A2, as well as those 20-substituted steroids disclosed in U.S. Pat. No. 4,599,331, those 21-hydroxy steroids disclosed in U.S. Pat. No. 4,771,042, those $C_{11}$-functionalized steroids disclosed in International Application Serial No. WO 1987/02672, 6α-fluoro17α,21-dihydroxy-16α-methylpregna-4,9(11)-diene-3,20-dione 21-acetate, 6α-fluoro-17α,21-dihydroxy-16β-methylpregna-4,9 (11)-diene-3,20-dione, 6α-fluoro-17α,21-dihydroxy-16β-methylpregna-4,9(11)-diene-3,20-dione 21-phosphonooxy and pharmaceutically acceptable salts thereof, hydrocortisone, tetrahydrocortisol, 17α-hydroxy-progesterone, 11α-epihydrocortisone, cortexolone, corticosterone, desoxycorticosterone, dexamethasone, cortisone 21-acetate, hydrocortisone 21-phosphate, 17α-hydroxy-6α-methylpregn-4-ene-3,20-dione 17-acetate, 6α-fluoro-17α,21-dihydroxy-16α-methylpregna-4,9(11)-diene-3,20-dione, and Δ9(11)-etianic esters, all disclosed in International Application Serial No. WO 1990/015816 A1.

Cartilage-derived angiogenesis inhibitor factors include, but are not limited to, peptide troponin and chondromodulin I.

Matrix metalloproteinase inhibitors of the present invention include, but are not limited to, succinyl hydroxamates such as marimastat and SC903, sulphonamide hydroxamates such as CGS27023A, phosphinamide hydroxamates, carboxylate inhibitors such as BAY12-9566, thiol inhibitors such as Compound B, aminomethyl benzimidazole analogues, peptides such as regasepin, and tetracyclines such as minocycline.

$\alpha_v\beta_3$ inhibitors include, but are not limited to, IS20I, P11 peptide, EMD 85189, and 66203, RGD peptide, RGD mimetics such as S 36578-2, echistatin, antibodies or antibody fragments against $\alpha_v\beta_3$ integrin such as Vitaxin, which targets the extracellular domain of the dimer, cilengitide, and peptidomimetics such as S247.

Anti-angiogenic siRNAs include, but are not limited to, siRNAs targeting mRNAs that are upregulated during angiogenesis, optionally PEGylated siRNAs targeting VEGF or VEGFR mRNAs, and siRNAs targeting UPR (unfolded protein response)-IRE1α, XBP-1, and ATF6 mRNAs. Additionally, it has been shown that siRNAs that are, at minimum, 21 nucleotides in length, regardless of targeting sequence, suppress neovascularization (Kleinman, et al., 2008) and may be included in the anti-angiogenic siRNAs of the present invention.

Inhibitors of the complement system include, but are not limited to, modified native complement components such as soluble complement receptor type 1, soluble complement receptor type 1 lacking long homologous repeat-A, soluble Complement Receptor Type 1-Sialyl Lewis$^x$, complement receptor type 2, soluble decay accelerating factor, soluble membrane cofactor protein, soluble CD59, decay accelerating factor-CD59 hybrid, membrane cofactor protein-decay accelerating factor hybrid, C1 inhibitor, and C1q receptor, complement-inhibitory antibodies such as anti-C5 monoclonal antibody and anti-C5 single chain Fv, synthetic inhibitors of complement activation such as antagonistic peptides and analogs targeting C5a receptor, and naturally occurring compounds that block complement activation such as heparin and related glycosaminoglycan compounds. Additional inhibitors of the complement system are disclosed by Makrides (Makrides, 1998).

As used herein, the term "vascular disrupting agent" means any compound that targets existing vasculature, e.g. tumor vasculature, damages or destroys said vasculature, and/or causes central tumor necrosis. In the present invention, examples of vascular disrupting agents include, but are not limited to, ABT-751 (Abbott), AVE8062 (Aventis), BCN105 (Bionomics), BMXAA (Antisoma), CA-4-P (OxiGene), CA-1-P (OxiGene), CYT997 (Cytopia), MPC-6827 (Myriad Pharmaceuticals), MN-029 (MediciNova), NPI-2358 (Nereus), Oxi4503 (Oxigene), TZT-1027 (Daichi Pharmaceuticals), ZD6126 (AstraZeneca and Angiogene), pharmaceutically acceptable salts thereof, and combinations thereof.

As used herein, a "molecularly targeted agent" is a substance that interferes with the function of a single molecule or group of molecules, preferably those that are involved in tumor growth and progression, when administered to a subject. Non-limiting examples of molecularly targeted agents of the present invention include signal transduction inhibitors, modulators of gene expression and other cellular functions, immune system modulators, antibody-drug conjugates (ADCs), and combinations thereof.

As used herein, a "signal transduction inhibitor" is a substance that disrupts communication between cells, such as when an extracellular signaling molecule activates a cell surface receptor. Non-limiting examples of signal transduction inhibitors of the present invention include anaplastic lymphoma kinase (ALK) inhibitors, B-Raf inhibitors, epidermal growth factor inhibitors (EGFRi), ERK inhibitors, Janus kinase inhibitors, MEK inhibitors, mammalian target of rapamycin (mTor) inhibitors, phosphoinositide 3-kinase inhibitors (PI3Ki), and Ras inhibitors.

As used herein, an "anaplastic lymphoma kinase (ALK) inhibitor" is a substance that (i) directly interacts with ALK, e.g., by binding to ALK and (ii) decreases the expression or the activity of ALK. Non-limiting examples of anaplastic lymphoma kinase (ALK) inhibitors of the present invention include crizotinib (Pfizer, New York, N.Y.), CH5424802 (Chugai Pharmaceutical Co., Tokyo, Japan), GSK1838705 (GlaxoSmithKline, United Kingdom), Chugai 13d (Chugai Pharmaceutical Co., Tokyo, Japan), CEP28122 (Teva Pharmaceutical Industries, Ltd., Israel), AP26113 (Ariad Pharmaceuticals, Cambridge, Mass.), Cephalon 30 (Teva Pharmaceutical Industries, Ltd., Israel), X-396 (Xcovery, Inc., West Palm Beach, Fla.), Amgen 36 (Amgen Pharmaceuticals, Thousand Oaks, Calif.), ASP3026 (Astellas Pharma US, Inc., Northbrook, Ill.), and Amgen 49 (Amgen Pharmaceuticals, Thousand Oaks, Calif.), pharmaceutically acceptable salts thereof, and combinations thereof.

As used herein, a "B-Raf inhibitor" of the present invention is a substance that (i) directly interacts with B-Raf, e.g., by binding to B-Raf and (ii) decreases the expression or the activity of B-Raf. B-Raf inhibitors may be classified into two types by their respective binding modes. As used herein, "Type 1" B-Raf inhibitors are those inhibitors that target the ATP binding sites of the kinase in its active conformation. "Type 2" B-Raf inhibitors are those inhibitors that preferentially bind to an inactive conformation of the kinase. Non-limiting examples of Type 1 B-Raf inhibitors of the present invention include:

Compound 7

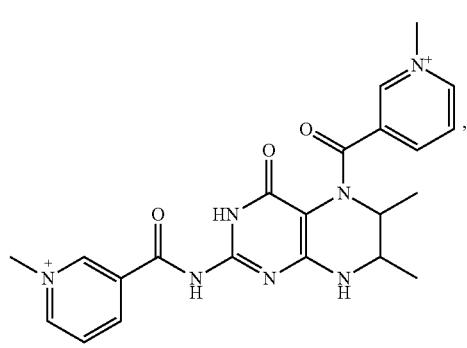

(Li et al., 2010)

Compound 9

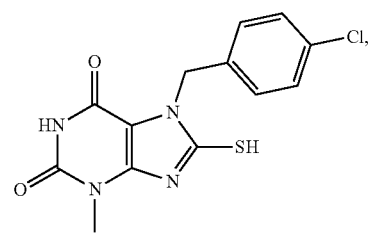

(Id.)

Compound 10

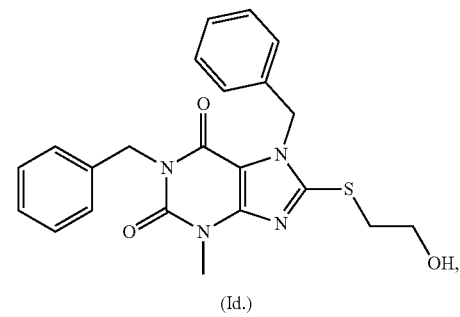

(Id.)

Compound 13

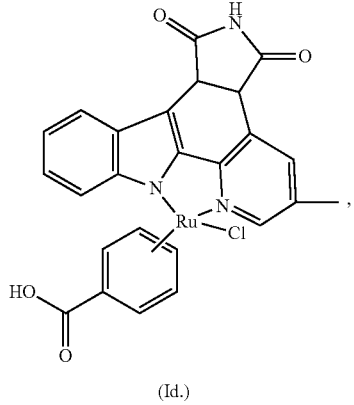

(Id.)

Compound 14

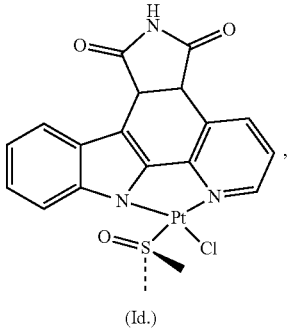

(Id.)

dabrafenib (GlaxoSmithKline), GDC-0879 (Genentech), L-779450 B-Raf (Merck), PLX3202 (Plexxikon), PLX4720 (Plexxikon), SB-590885 (GlaxoSmithKline), SB-699393 (GlaxoSmithKline), vemurafenib (Plexxikon), pharmaceutically acceptable salts thereof, and combinations thereof. Preferably, the type 1 RAF inhibitor is dabrafenib or a pharmaceutically acceptable salt thereof.

Non-limiting examples of Type 2 B-Raf inhibitors of the present invention include:

Compound 15

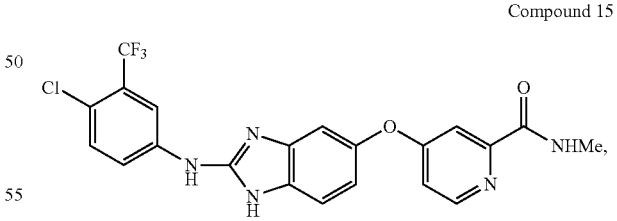

(Li et al., 2010)

Compound 16

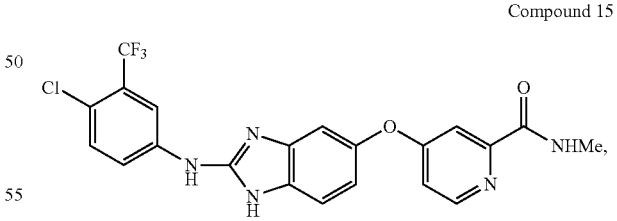

(Id.)

Compound 18
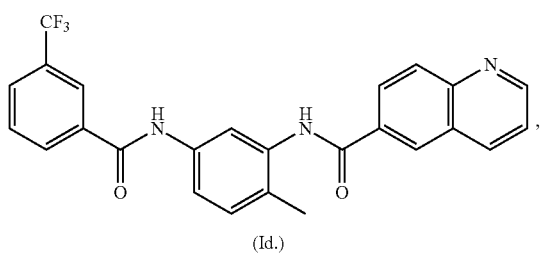
Compound 19
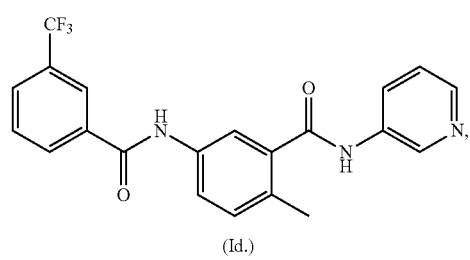
Compound 20
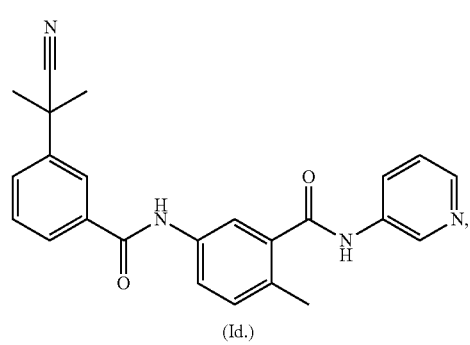
Compound 21
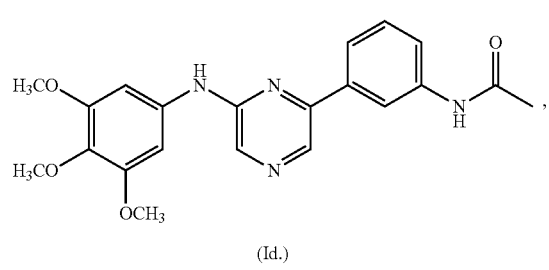
Compound 22
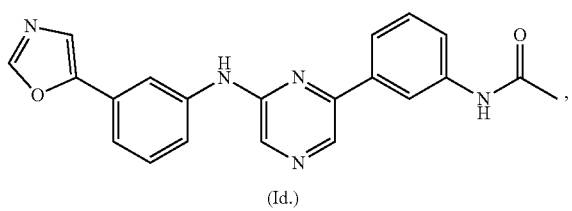
Compound 23
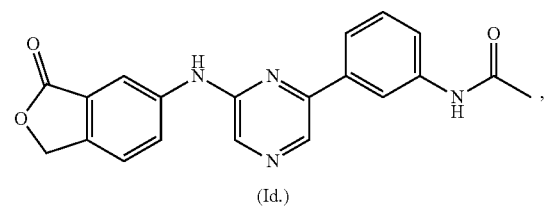
Compound 24
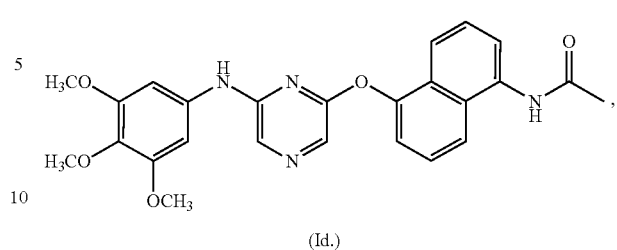
Compound 25
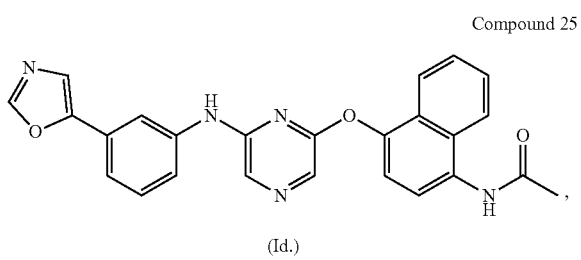
Compound 26
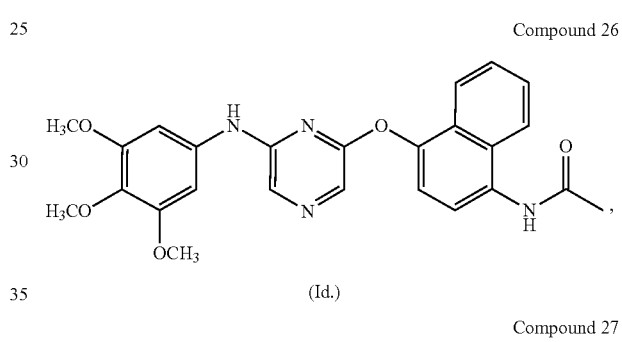
Compound 27
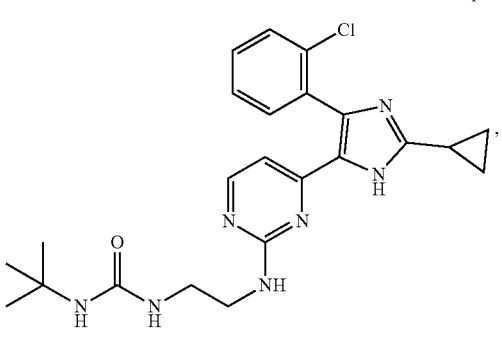
Compound 28
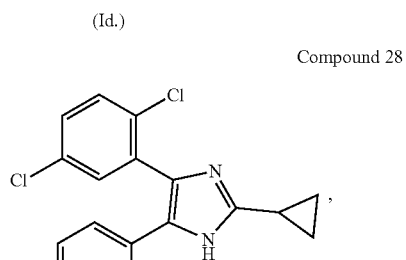

Compound 30
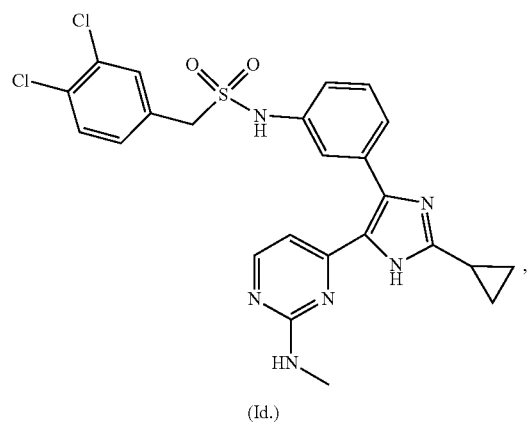
(Id.)
Compound 31
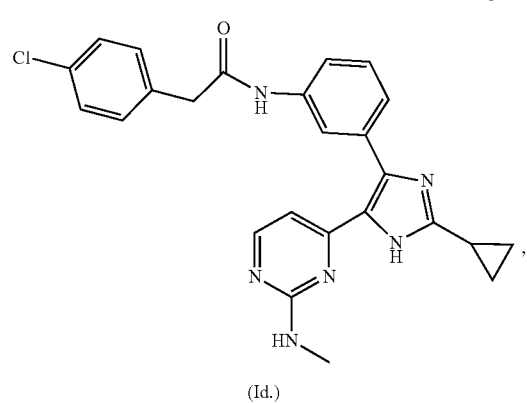
(Id.)
Compound 32
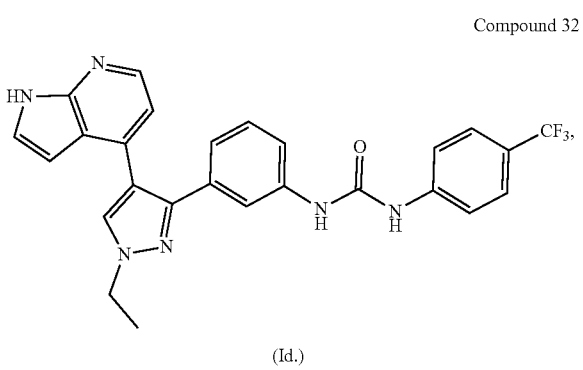
(Id.)
Compound 33
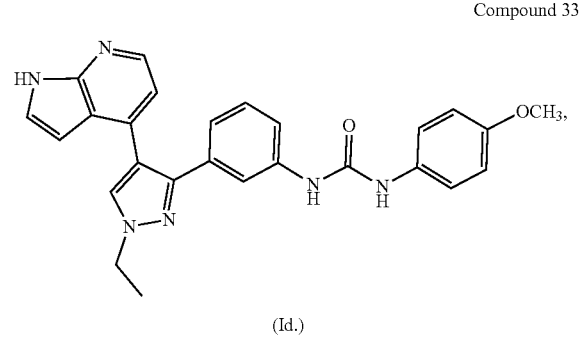
(Id.)
Compound 34
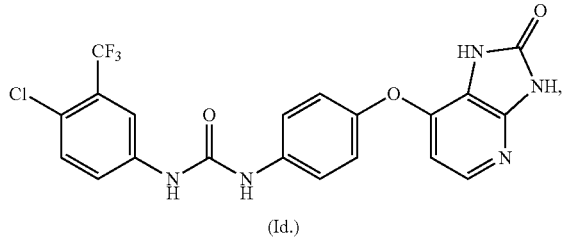
(Id.)
Compound 35
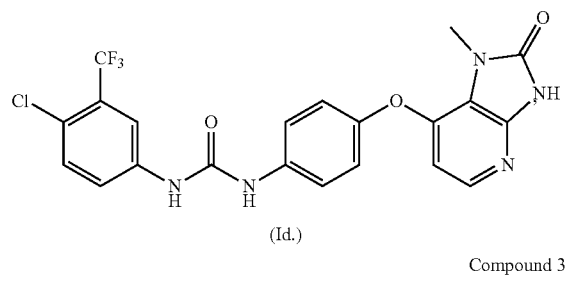
(Id.)
Compound 36
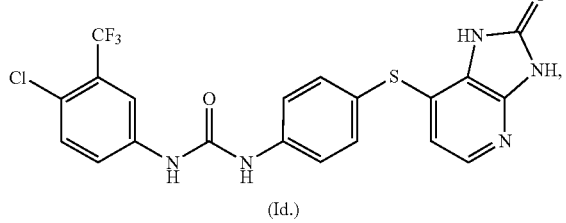
(Id.)
Compound 37
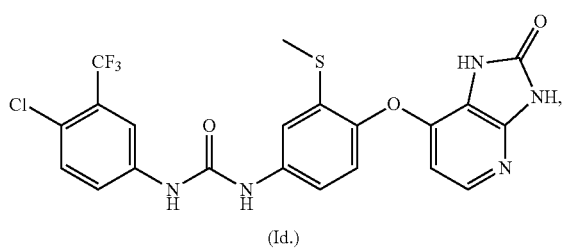
(Id.)
Compound 38
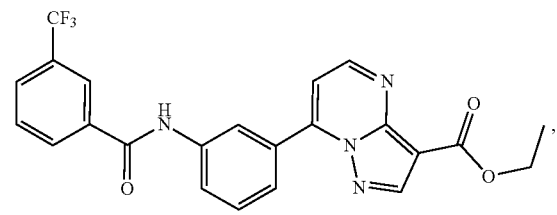
(Id.)
Compound 39
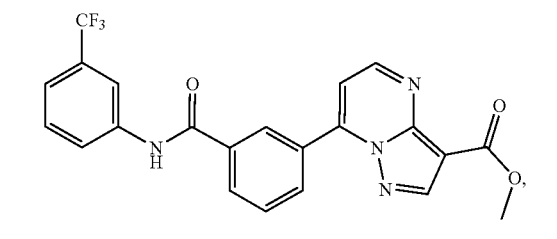
(Id.)

Compound 40

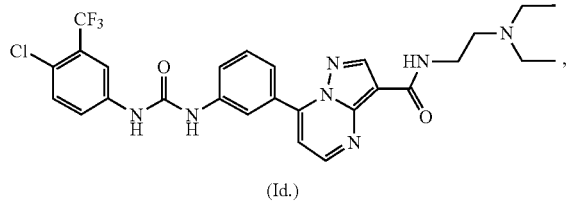

(Id.)

Sorafenib (Onyx Pharmaceuticals), ZM-336372 (AstraZeneca), pharmaceutically acceptable salts thereof, and combinations thereof Other B-Raf inhibitors include, without limitation, AAL881 (Novartis); AB-024 (Ambit Biosciences), ARQ-736 (ArQule), ARQ-761 (ArQule), AZ628 (Axon Medchem BV), BeiGene-283 (BeiGene), BIIB-024 (MLN 2480) (Sunesis & Takeda), b raf inhibitor (Sareum), BRAF kinase inhibitor (Selexagen Therapeutics), BRAF siRNA 313 (tacaccagcaagctagatgca) and 253 (cctatcgttagagtcttcctg) (Liu et al., 2007), CTT239065 (Institute of Cancer Research), DP-4978 (Deciphera Pharmaceuticals), HM-95573 (Hanmi), GW 5074 (Sigma Aldrich), ISIS 5132 (Novartis), LErafAON (NeoPharm, Inc.), LBT613 (Novartis), LGX 818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof.

As used herein, an "EGFR inhibitor" is a substance that (i) directly interacts with EGFR, e.g. by binding to EGFR and (ii) decreases the expression or the activity of EGFR. Non-limiting examples of EGFR inhibitors according to the present invention include (+)-Aeroplysinin-1 (CAS #28656-91-9), 3-(4-Isopropylbenzylidenyl)-indolin-2-one, ABT-806 (Life Science Pharmaceuticals), AC-480 (Bristol-Myers Squibb), afatinib (Boehringer Ingelheim), AG 1478 (CAS #153436-53-4), AG 494 (CAS #133550-35-3), AG 555 (CAS #133550-34-2), AG 556 (CAS #133550-41-1), AG 825 (CAS #149092-50-2), AG-490 (CAS #134036-52-5), antroquinonol (Golden Biotechnology), AP-26113 (Ariad), ARRY334543 (CAS #845272-21-1), AST 1306 (CAS #897383-62-9), AVL-301 (Celgene), AZD8931 (CAS #848942-61-0), BIBU 1361 (CAS #793726-84-8), BIBX 1382 (CAS #196612-93-8), BMS-690514 (Bristol-Myers Squibb), BPIQ-I (CAS #174709-30-9), Canertinib (Pfizer), cetuximab (Actavis), cipatinib (Jiangsu Hengrui Medicine), CL-387,785 (Santa Cruz Biotech), compound 56 (CAS #171745-13-4), CTX-023 (CytomX Therapeutics), CUDC-101 (Curis), dacomitinib (Pfizer), DAPH (CAS #145915-58-8), daphnetin (Santa Cruz Biotech), dovitinib lactate (Novartis), EGFR Inhibitor (CAS #879127-07-8), epitinib (Hutchison China MediTech), erbstatin Analog (CAS #63177-57-1), erlotinib (Astellas), gefitinib (AstraZeneca), GT-MAB 5.2-GEX (Glycotope), GW 583340 (CAS #388082-81-3), GW2974 (CAS #202272-68-2), HDS 029 (CAS #881001-19-0), Hypericin (Santa Cruz Biotech), icotinib hydrochloride (Betapharma), JNJ-26483327 (Johnson & Johnson), JNJ-28871063 (Johnson & Johnson), KD-020 (Kadmon Pharmaceuticals), lapatinib ditosylate (GlaxoSmithKline), Lavendustin A (Sigma), Lavendustin C (Sigma), LY-3016859 (Eli Lilly), MEHD-7945A (Hoffmann-La Roche), MM-151 (Merrimack), MT-062 (Medisyn Technologies), necitumumab (Eli Lilly), neratinib (Pfizer), nimotuzumab (Center of Molecular Immunology), NT-004 (NewGen Therapeutics), pantiumumab (Amgen), PD 153035 (CAS #153436-54-5), PD 161570 (CAS #192705-80-9), PD 168393, PD 174265 (CAS #216163-53-0), pirotinib (Sihuan Pharmaceutical), poziotinib (Hanmi), PP 3 (CAS #5334-30-5), PR-610 (Proacta), pyrotinib (Jiangsu Hengrui Medicine), RG-13022 (CAS #136831-48-6), rindopepimut (Celldex Therapeutics), RPI-1 (CAS #269730-03-2), S-222611 (Shionogi), TAK 285 (CAS #871026-44-7), TAS-2913 (Taiho), theliatinib (Hutchison China MediTech), Tyrphostin 47 (RG-50864, AG-213) (CAS #118409-60-2), Tyrphostin 51 (CAS #122520-90-5), Tyrphostin AG 1478 (CAS #175178-82-2), Tyrphostin AG 183 (CAS #126433-07-6), Tyrphostin AG 528 (CAS #133550-49-9), Tyrphostin AG 99 (CAS #118409-59-9), Tyrphostin B42 (Santa Cruz Biotech), Tyrphostin B44 (Santa Cruz Biotech), Tyrphostin RG 14620 (CAS #136831-49-7), vandetanib (AstraZeneca), varlitinib (Array BioPharma), vatalanib (Novartis), WZ 3146 (CAS #1214265-56-1), WZ 4002 (CAS #1213269-23-8), WZ8040 (CAS #1214265-57-2), XL-647 (Exelixis), Z-650 (HEC Pharm), ZM 323881 (CAS #324077-30-7), pharmaceutically acceptable salts thereof, and combinations thereof. Preferably, the EGFR inhibitor is selected from the group consisting of panitumumab, erlotinib, pharmaceutically acceptable salts thereof, and combinations thereof.

As used herein, an "ERK inhibitor" is a substance that (i) directly interacts with ERK, including ERK1 and ERK2, e.g., by binding to ERK and (ii) decreases the expression or the activity of an ERK protein kinase. Therefore, inhibitors that act upstream of ERK, such as MEK inhibitors and RAF inhibitors, are not ERK inhibitors according to the present invention. Non-limiting examples of ERK inhibitors of the present invention include AEZS-131 (Aeterna Zentaris), AEZS-136 (Aeterna Zentaris), SCH-722984 (Merck & Co.), SCH-772984 (Merck & Co.), SCH-900353 (MK-8353) (Merck & Co.), pharmaceutically acceptable salts thereof, and combinations thereof.

As used herein, a "Janus kinase inhibitor" is a substance that (i) directly interacts with a Janus kinase, e.g., by binding to a Janus kinase and (ii) decreases the expression or the activity of a Janus kinase. Janus kinases of the present invention include Tyk2, Jak1, Jak2, and Jak3. Non-limiting examples of Janus kinase inhibitors of the present invention include ruxolitinib (Incyte Corporation, Wilmington, Del.), baricitinib (Incyte Corporation, Wilmington, Del.), tofacitinib (Pfizer, New York, N.Y.), VX-509 (Vertex Pharmaceuticals, Inc., Boston, Mass.), GLPG0634 (Galapagos NV, Belgium), CEP-33779 (Teva Pharmaceuticals, Israel), pharmaceutically acceptable salts thereof, and combinations thereof As used herein, a "MEK inhibitor" is a substance that (i) directly interacts with MEK, e.g., by binding to MEK and (ii) decreases the expression or the activity of MEK. Therefore, inhibitors that act upstream of MEK, such as RAS inhibitors and RAF inhibitors, are not MEK inhibitors according to the present invention. MEK inhibitors may be classified into two types depending on whether the inhibitor competes with ATP. As used herein, a "Type 1" MEK inhibitor is an inhibitor that competes with ATP for binding to MEK. A "Type 2" MEK inhibitor is an inhibitor that does not compete with ATP for binding to MEK. Non-limiting examples of type 1 MEK inhibitors according to the present invention include bentamapimod (Merck KGaA), L783277 (Merck), RO092210 (Roche), pharmaceutically acceptable salts thereof, and combinations thereof. Preferably, the type 1 MEK inhibitor is RO092210 (Roche) or a pharmaceutically acceptable salt thereof. Non-limiting examples of type 2 MEK inhibitors according to the present invention include anthrax toxin, lethal factor portion of anthrax toxin, ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), MEK162 (Array BioPharma), PD 098059 (2-(2'-amino-3'-methoxyphenyl)-oxanaphthalen-4-one), PD 184352 (CI-1040), PD-0325901 (Pfizer), pimasertib (Santhera Pharmaceuticals), refametinib (AstraZeneca), selumetinib (AZD6244) (AstraZeneca), TAK-733 (Takeda), trametinib (Japan Tobacco), U0126 (1,4-diamino-2,3-dicyano-1,4-bis(2-aminophenylthio)butadiene) (Sigma), RDEA119 (Ardea Biosciences/Bayer), pharmaceutically acceptable salts thereof, and combinations thereof. Preferably, the type 2 MEK inhibitor is trametinib or a pharmaceutically acceptable salt thereof. Other MEK inhibitors include, without limitation, antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof.

As used herein, an "mTOR inhibitor" is a substance that (i) directly interacts with mTOR, e.g. by binding to mTOR and (ii) decreases the expression or the activity of mTOR. Non-limiting examples of mTOR inhibitors according to the present invention include zotarolimus (AbbVie), umirolimus (Biosensors), temsirolimus (Pfizer), sirolimus (Pfizer), sirolimus NanoCrystal (Elan Pharmaceutical Technologies), sirolimus TransDerm (TransDerm), sirolimus-PNP (Samyang), everolimus (Novartis), biolimus A9 (Biosensors), ridaforolimus (Ariad), rapamycin, TCD-10023 (Terumo), DE-109 (MacuSight), MS-R001 (MacuSight), MS-R002 (MacuSight), MS-R003 (MacuSight), Perceiva (MacuSight), XL-765 (Exelixis), quinacrine (Cleveland BioLabs), PKI-587 (Pfizer), PF-04691502 (Pfizer), GDC-0980 (Genentech and Piramed), dactolisib (Novartis), CC-223 (Celgene), PWT-33597 (Pathway Therapeutics), P-7170 (Piramal Life Sciences), LY-3023414 (Eli Lilly), INK-128 (Takeda), GDC-0084 (Genentech), DS-7423 (Daiichi Sankyo), DS-3078 (Daiichi Sankyo), CC-115 (Celgene), CBLC-137 (Cleveland BioLabs), AZD-2014 (AstraZeneca), X-480 (Xcovery), X-414 (Xcovery), EC-0371 (Endocyte), VS-5584 (Verastem), PQR-401 (Piqur), PQR-316 (Piqur), PQR-311 (Piqur), PQR-309 (Piqur), PF-06465603 (Pfizer), NV-128 (Novogen), nPT-MTOR (Biotica Technology), BC-210 (Biotica Technology), WAY-600 (Biotica Technology), WYE-354 (Biotica Technology), WYE-687 (Biotica Technology), LOR-220 (Lorus Therapeutics), HMPL-518 (Hutchison China MediTech), GNE-317 (Genentech), EC-0565 (Endocyte), CC-214 (Celgene), and ABTL-0812 (Ability Pharmaceuticals).

As used herein, a "PI3K inhibitor" is a substance that decreases the expression or the activity of phosphatidylinositol-3 kinases (PI3Ks) or downstream proteins, such as Akt. PI3Ks, when activated, phosphorylate the inositol ring 3'-OH group in inositol phospholipids to generate the second messenger phosphatidylinositol-3,4,5-trisphosphate (PI-3,4,5-P(3)). Akt interacts with a phospholipid, causing it to translocate to the inner membrane, where it is phosphorylated and activated. Activated Akt modulates the function of numerous substrates involved in the regulation of cell survival, cell cycle progression and cellular growth.

Non-limiting examples of PI3K inhibitors according to the present invention include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (GDC-0941) (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof. Preferably, the inhibitor of the PI3K/Akt pathway is pictilisib (GDC-0941) or a pharmaceutically acceptable salt thereof.

As used herein, a "RAS inhibitor" is a substance that (i) directly interacts with RAS, e.g., by binding to RAS and (ii) decreases the expression or the activity of RAS. Non-limiting examples of RAS inhibitors according to the present invention include farnesyl transferase inhibitors (such as, e.g., tipifarnib and lonafarnib), farnesyl group-containing small molecules (such as, e.g., salirasib and TLN-4601), DCAI, as described by Maurer (Maurer, et al., 2012), Kobe0065 and Kobe2602, as described by Shima (Shima, et al., 2013), and HBS 3 (Patgiri, et al., 2011), and AIK-4 (Allinky), pharmaceutically acceptable salts thereof, and combinations thereof.

As used herein, "gene expression" is a process by which the information from DNA is used in the formation of a polypeptide. A "modulator of gene expression and other cellular functions" is a substance that affects gene expression and other works of a cell. Non-limiting examples of such modulators include hormones, histone deacetylase inhibitors (HDACi), and cyclin-dependent kinase inhibitors (CDKi), and poly ADP ribose polymerase (PARP) inhibitors.

In the present invention, a "hormone" is a substance released by cells in one part of a body that affects cells in another part of the body. Non-limiting examples of hormones according to the present invention include prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. Non-limiting examples of hormone-interfering compounds according to the present invention include tamoxifen (Nolvadex®), anastrozole (Arimidex®), letrozole (Femara®), and fulvestrant (Faslodex®). Such compounds are also within the meaning of hormone in the present invention.

As used herein, an "HDAC inhibitor" is a substance that (i) directly interacts with HDAC, e.g., by binding to HDAC and (ii) decreases the expression or the activity of HDAC. Non-limiting examples of HDAC inhibitors according to the present invention include 4SC-201 (4SC AG), 4SC-202 (Takeda), abexinostat (Celera), AN-1 (Titan Pharmaceuticals, Inc.), Apicidine (Merck & Co., Inc.), AR-42 (Arno Therapeutics), ARQ-700RP (ArQule), Avugane (TopoTarget AS), azelaic-1-hydroxamate-9-anilide (AAHA), belinostat (TopoTarget), butyrate (Enzo Life Sciences, Inc.), CG-1255 (Errant Gene Therapeutics, LLC), CG-1521 (Errant Gene Therapeutics, LLC), CG-200745 (CrystalGenomics, Inc.), chidamide (Shenzhen Chipscreen Biosciences), CHR-3996 (Chroma Therapeutics), CRA-024781 (Pharmacyclics), CS-3158 (Shenzhen Chipscreen Biosciences), CU-903 (Curis), DAC-60 (Genextra), entinostat (Bayer), hyaluronic acid butyric acid ester (HA-But), IKH-02 (IkerChem), IKH-35 (IkerChem), ITF-2357 (Italfarmaco), ITF-A (Italfarmaco), JNJ-16241199 (Johnson & Johnson), KA-001 (Karus Therapeutics), KAR-3000 (Karus Therapeutics), KD-5150 (Kalypsys), KD-5170 (Kalypsys), KLYP-278 (Kalypsys), KLYP-298 (Kalypsys), KLYP-319 (Kalypsys), KLYP-722 (Kalypsys), m-carboxycinnamic acid bis-hydroxamide (CBHA), MG-2856 (MethylGene), MG-3290 (MethylGene), MG-4230 (MethylGene), MG-4915 (MethylGene), MG-5026 (MethylGene), MGCD-0103 (MethylGene Inc.), mocetinostat (MethylGene), MS-27-275 (Schering AG), NBM-HD-1 (NatureWise), NVP-LAQ824 (Novartis), OCID-4681-S-01 (Orchid Pharmaceuticals), oxamflatin ((2E)-5-[3-[(phenylsufonyl) aminol phenyl]-pent-2-en-4-ynohydroxamic acid), panobinostat (Novartis), PCI-34051 (Pharmacyclics), phenylbutyrate (Enzo Life Sciences, Inc.), pivaloyloxymethyl butyrate (AN-9, Titan Pharmaceuticals, Inc.), pivanex (Titan Pharmaceuticals, Inc.), pracinostat (SBIO), PX-117794 (TopoTarget AS), PXD-118490 (LEO-80140) (TopoTarget AS), pyroxamide (suberoyl-3-amino-pyridineamide hydroxamic acid), resminostat (Takeda), RG-2833 (RepliGen), ricolinostat (Acetylon), romidepsin (Astellas), SB-1304 (S*BIO), SB-1354 (S*BIO), SB-623 (Merrion Research I Limited), SB-624 (Merrion Research I Limited), SB-639 (Merrion Research I Limited), SB-939 (S*BIO), Scriptaid (N-Hydroxy-1,3-dioxo-1H-benz[de]isoquinoline-2(3H)-hexan amide), SK-7041 (In2Gen/SK Chemical Co.), SK-7068 (In2Gen/SK Chemical Co.), suberoylanilide hydroxamic acid (SAHA), sulfonamide hydroxamic acid, tributyrin (Sigma Aldrich), trichostatin A (TSA) (Sigma Aldrich), valporic acid (VPA) (Sigma Aldrich), vorinostat (Zolinza), WF-27082B (Fujisawa Pharmaceutical Company, Ltd.), pharmaceutically acceptable salts thereof, and combinations thereof. Preferably, the HDAC inhibitor is romidepsin, pharmaceutically acceptable salts thereof, and combinations thereof.

As used herein, "CDK" is a family of protein kinases that regulate the cell cycle. Known CDKs include cdk1, cdk2, ckd3, ckd4, cdk5, cdk6, cdk7, cdk8, cdk9, cdk10, and cdk11. A "CDK inhibitor" is a substance that (i) directly interacts with CDK, e.g. by binding to CDK and (ii) decreases the expression or the activity of CDK. Non-limiting examples of CDK inhibitors according to the present invention include 2-Hydroxybohemine, 3-ATA, 5-Iodo-Indirubin-3'-monoxime, 9-Cyanopaullone, Aloisine A, Alsterpaullone 2-Cyanoethyl, alvocidib (Sanofi), AM-5992 (Amgen), Aminopurvalanol A, Arcyriaflavin A, AT-7519 (Astex Pharmaceuticals), AZD 5438 (CAS #602306-29-6), BMS-265246 (CAS #582315-72-8), BS-181 (CAS #1092443-52-1), Butyrolactone I (CAS #87414-49-1), Cdk/Crk Inhibitor (CAS #784211-09-2), Cdk1/5 Inhibitor (CAS #40254-90-8), Cdk2 Inhibitor II (CAS #222035-13-4), Cdk2 Inhibitor IV, NU6140 (CAS #444723-13-1), Cdk4 Inhibitor (CAS #546102-60-7), Cdk4 Inhibitor III (CAS #265312-55-8), Cdk4/6 Inhibitor IV (CAS #359886-84-3), Cdk9 Inhibitor II (CAS #140651-18-9), CGP 74514A, CR8, CYC-065 (Cyclacel), dinaciclib (Ligand), (R)-DRF053 dihydrochloride (CAS #1056016-06-8), Fascaplysin, Flavopiridol, Hygrolidin, Indirubin, LEE-011 (Astex Pharmaceuticals), LY-2835219 (Eli Lilly), milciclib maleate (Nerviano Medical Sciences), MM-D37K (Maxwell Biotech), N9-Isopropyl-olomoucine, NSC 625987 (CAS #141992-47-4), NU2058 (CAS #161058-83-9), NU6102 (CAS #444722-95-6), Olomoucine, ON-108600 (Onconova), ON-123300 (Onconova), Oxindole I, P-1446-05 (Piramal), P-276-00 (Piramal), palbociclib (Pfizer), PHA-767491 (CAS #845714-00-3), PHA-793887 (CAS #718630-59-2), PHA-848125 (CAS #802539-81-7), Purvalanol A, Purvalanol B, R547 (CAS #741713-40-6), RO-3306 (CAS #872573-93-8), Roscovitine, SB-1317 (SBIO), SCH 900776 (CAS #891494-63-6), SEL-120 (Selvita), seliciclib (Cyclacel), SNS-032 (CAS #345627-80-7), SU9516 (CAS #377090-84-1), WHI-P180 (CAS #211555-08-7), pharmaceutically acceptable salts thereof, and combinations thereof. Preferably, the CDK inhibitor is selected from the group consisting of dinaciclib, palbociclib, pharmaceutically acceptable salts thereof, and combinations thereof.

As used herein, a "poly ADP ribose polymerase (PARP) inhibitor" is a substance that decreases the expression or activity of poly ADP ribose polymerases (PARPs) or downstream proteins. Non-limiting examples of poly ADP ribose polymerase (PARP) inhibitors of the present invention include PF01367338 (Pfizer, New York, N.Y.), olaparib (AstraZeneca, United Kingdom), iniparib (Sanofi-Aventis, Paris, France), veliparib (Abbott Laboratories, Abbott Park, Ill.), MK 4827 (Merck, White House Station, N.J.), CEP 9722 (Teva Pharmaceuticals, Israel), LT-673 (Biomarin, San Rafael, Calif.), and BSI 401 (Sanofi-Aventis, Paris, France), pharmaceutically acceptable salts thereof, and combinations thereof.

In a preferred embodiment, the chemotherapy comprises administering to the human an agent selected from the group consisting of gemcitabine, taxol, adriamycin, ifosfamide, trabectedin, pazopanib, abraxane, avastin, everolimus, and combinations thereof.

As used herein, "radiotherapy" means any therapeutic regimen, that is compatible with the *C. novyi*, e.g., *C. novyi* NT, treatment of the present invention and in which radiation is delivered to a subject, e.g., a human, for the treatment of cancer. Radiotherapy can be delivered to, e.g., a human subject, by, for example, a machine outside the body (external-beam radiation therapy) or a radioactive material inside the body (brachytherapy, systemic radiation therapy).

External-beam radiation therapy includes, but is not limited to, 3-dimensional conformal radiation therapy, intensity-modulated radiation therapy, image-guided radiation therapy, tomotherapy, stereotactic radiosurgery, stereotactic body radiation therapy, proton therapy, and other charged particle beam therapies, such as electron beam therapy. External-beam radiation therapies are widely used in cancer treatment and are well known to those of skill in the art.

Brachytherapy means radiotherapy delivered by being implanted in, or placed on, a subject's body. Brachytherapy includes, but is not limited to, interstitial brachytherapy, intracavitary brachytherapy, and episcleral brachytherapy. Brachytherapy techniques are also widely used in cancer treatment and are well known to those of skill in the art.

Systemic radiation therapy means radiotherapy delivered by injection to or ingestion by a subject. One example of systemic radiation therapy is radioiodine therapy. Radioiodine is a radiolabeled iodine molecule that is safe and effective for use in a subject, such as, e.g., a human. Non-limiting examples of radioiodine according to the present invention may be selected from the group consisting of $^{123}I$, $^{124}I$, $^{125}I$, $^{131}I$, and combinations thereof. Preferably, the radioiodine is $^{131}I$.

As used herein, "immunotherapy" means any anti-cancer therapeutic regimen that is compatible with the *C. novyi*, e.g., *C. novyi* NT, treatment of the present invention and that uses a substance that alters the immune response by augmenting or reducing the ability of the immune system to produce antibodies or sensitized cells that recognize and react with the antigen that initiated their production. Immunotherapies may be recombinant, synthetic, or natural preparations and include cytokines, corticosteroids, cytotoxic agents, thymosin, and immunoglobulins. Some immunotherapies are naturally present in the body, and certain of these are available in pharmacologic preparations. Examples of immunotherapies include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In one preferred embodiment, the immunotherapy comprises administering to the human an immune checkpoint inhibitor. As used herein, an "immune checkpoint inhibitor" means a substance that blocks the activity of molecules involved in attenuating the immune response. Such molecules include, for example, cytotoxic T-lymphocyte-associated antigen 4 (CTLA-4) and programmed cell death protein 1 (PD-1). Immune checkpoint inhibitors of the present invention include, but are not limited to, ipilimumab (Bristol-Myers Squibb), tremelimumab (Pfizer), MDX-1106 (Medarex, Inc.), MK3475 (Merck), CT-011 (CureTech, Ltd.), AMP-224 (Ampmmune), MDX-1105 (Medarex, Inc.), IMP321 (Immutep S.A.), and MGA271 (Macrogenics).

In an additional aspect of this embodiment, the *C. novyi*, e.g., *C. novyi* NT, therapy of the present invention is effective against, e.g., solid tumors that are resistant to a therapy selected from the group consisting of chemotherapy, radiation therapy, immunotherapy, and combinations thereof.

In another aspect of this embodiment, the solid tumor is refractory to standard therapy or the solid tumor is without an available standard therapy, yet the *C. novyi*, e.g., *C. novyi* NT, therapy of the present invention is effective against such a tumor.

As used herein, "resistant" and "refractory" are used interchangeably. Being "refractory" to a therapy means that the prior therapy or therapies has/have reduced efficacy in, e.g., treating cancer or killing cancer cells, compared to the same subject prior to becoming resistant to the therapy.

As used herein, the term "standard therapy" means those therapies generally accepted by medical professionals as appropriate for treatment of a particular cancer, preferably a particular solid tumor. Standard therapies may be the same or different for different tumor types. Standard therapies are typically approved by various regulatory agencies, such as, for example, the U.S. Food and Drug Administration.

In a further aspect of this embodiment, the method induces a potent localized inflammatory response and an adaptive immune response in the human.

As used herein, an "inflammatory response" is a local response to cellular damage, pathogens, or irritants that may include, but is not limited to, capillary dilation, leukocytic infiltration, swelling, redness, heat, itching, pain, loss of function, and combinations thereof.

As used herein, an "adaptive immune response" involves B and T cells of a subject's immune system. Upon exposure to a pathogenic substance, for example, a cancer cell, B cells may produce antibodies against pathogenic antigens on the pathogenic substance, and T cells may become able to target pathogens for eventual destruction. Certain populations of B and T cells, specific for a given antigen, are retained by the immune system and are called upon in the event of subsequent exposure to the pathogenic antigen. An adaptive immune response is thus durable, and provides a host subject's immune system with the continual ability to recognize and destroy a given pathogenic antigen-presenting pathogen.

Another embodiment of the present invention is a method for debulking a solid tumor present in a human. This method comprises administering intratumorally to the human a unit dose of *C. novyi*, preferably *C. novyi* NT, CFUs comprising about $1\times10^3$-$1\times10^7$ CFUs suspended in a pharmaceutically acceptable carrier or solution.

As used herein, "debulking" a solid tumor means to reduce the size of or the number of cancer in a solid tumor. Such a procedure is palliative and may be used to enhance the effectiveness of the treatments, including radiation therapy, chemotherapy, or amputation. In this embodiment, solid tumors are as set forth above. Preferably, the solid tumor is selected from the group consisting of soft tissue sarcoma, hepatocellular carcinoma, breast cancer, pancreatic cancer, and melanoma. More preferably, the solid tumor is a leiomyosarcoma, such as a retroperitoneal leiomyosarcoma.

An additional embodiment of the present invention is a method for debulking a solid tumor present in a human. This method comprises administering intratumorally to the human one to four cycles of a unit dose of C. novyi NT spores comprising about $1 \times 10^4$ spores per cycle, each unit dose of C. novyi NT being suspended in a pharmaceutically acceptable carrier or solution. In this embodiment, the types of solid tumors are as set forth above. Preferably, the solid tumor is selected from the group consisting of soft tissue sarcoma, hepatocellular carcinoma, breast cancer, pancreatic cancer, and melanoma.

A further embodiment of the present invention is a method for treating or ameliorating an effect of a solid tumor present in a human. This method comprises administering intratumorally to the human one to four cycles of a unit dose of C. novyi NT spores comprising about $1 \times 10^4$ spores per cycle, each unit dose of C. novyi NT spores being suspended in a pharmaceutically acceptable carrier or solution. Various types of solid tumors are as set forth above. Preferably, the solid tumor is selected from the group consisting of soft tissue sarcoma, hepatocellular carcinoma, breast cancer, pancreatic cancer, and melanoma.

Another embodiment of the present invention is method for ablating a solid tumor present in a human. This method comprises administering intratumorally to the human a unit dose of C. novyi, preferably C. novyi NT, CFUs comprising about $1 \times 10^3$-$1 \times 10^7$ CFUs suspended in a pharmaceutically acceptable carrier or solution, wherein the tumor is ablated leaving a margin of normal tissue.

As used herein, "ablating" a solid tumor means that the process removes all of the solid tumor. In this process, after carrying out the treatment, a margin of normal tissue is left surrounding the area where the tumor once resided. In this embodiment, the types of solid tumors are as set forth above. Preferably, the solid tumor is a sarcoma. More preferably, the solid tumor is a leiomyosarcoma, such as a retroperitoneal leiomyosarcoma.

A further embodiment of the present invention is a unit dose of C. novyi CFUs. This unit dose comprises about $1 \times 10^3$-$1 \times 10^7$ CFUs in a pharmaceutically acceptable carrier or solution, which is effective for treating or ameliorating an effect of a solid tumor present in a human. As set forth above, the C. novyi CFUs may be in vegetative and spore forms.

In one aspect of this embodiment, the C. novyi is C. novyi NT. Preferably, the unit dose comprises about $1 \times 10^4$-$1 \times 10^7$ C. novyi NT spores, such as about $1 \times 10^6$-$1 \times 10^7$ C. novyi NT spores, in a pharmaceutically acceptable carrier or solution. Preferably, the unit dose comprises about $1 \times 10^4$ C. novyi NT spores in a pharmaceutically acceptable carrier or solution.

An additional embodiment of the present invention is a kit for treating or ameliorating an effect of a solid tumor present in a human. This kit comprises a unit dose of C. novyi CFUs comprising about $1 \times 10^3$-$1 \times 10^7$ CFUs in a pharmaceutically acceptable carrier or solution and instructions for use of the kit. The kit may be divided into one or more compartments and may have one or more containers for the various reagents. The kit may be further adapted to support storage and shipment of each component.

In one aspect of this embodiment, the kit further comprises one or more antibiotics, which are effective to treat or alleviate an adverse side effect caused by the C. novyi CFUs. The CFUs may be in vegetative or spore forms. Suitable antibiotics are as set forth above. Preferably, the kit further comprises 1-4 unit doses of the C. novyi for carrying out 1-4 treatment cycles.

In another aspect of this embodiment, the C. novyi is C. novyi NT. Preferably, the unit dose comprises about $1 \times 10^4$-$1 \times 10^7$ C. novyi NT spores, such as about $1 \times 10^6$-$1 \times 10^7$ C. novyi NT spores, or about $1 \times 10^4$ C. novyi NT spores, in a pharmaceutically acceptable carrier or solution. Also preferably, the kit further comprises 1-4 unit doses of the C. novyi NT spores for carrying out 1-4 treatment cycles.

Another embodiment of the present invention is a method for microscopically precise excision of tumor cells in a human. This method comprises administering intratumorally to the human a unit dose of C. novyi NT colony forming units (CFUs) comprising about $1 \times 10^3$-$1 \times 10^7$ CFUs suspended in a pharmaceutically acceptable carrier or solution.

As used herein, "microscopically precise excision" means elimination of a target tissue in a subject, for example, a pathogenic tissue, said elimination being essentially specific, at the cellular level, for the pathogenic tissue while causing minimal or no harm to nearby "healthy" tissue. Elimination of a target tissue may be, but is not limited to, apoptosis, necrosis, and cell lysis. This embodiment may be accomplished by precision delivery of, e.g., the C. novyi NT spores of the invention via CT-guided intratumoral injection using, e.g., a multi-pronged delivery device, such as a multi-pronged needle.

In the present invention, the C. novyi spores, such as the C. novyi NT spores, are delivered to the subject, e.g., human patient, intratumorally in any medically appropriate manner. For example, C. novyi NT spores may be delivered via a single needle used at one or more sites on a tumor. Alternatively, a multi-tined delivery vehicle, such as a multi-tined needle, may be used to deliver, e.g., C. novyi NT spores, to a tumor. Delivery of, e.g., the spores may be to the same or multiple depths at one or more sites of the tumor. The selected delivery vehicles may be operated manually or controlled electronically. The delivery vehicles may be positioned and/or repositioned on or within a tumor manually or via a remote controlled device and visualization of the injection site may be augmented using various imaging techniques known in the art, such as CT imaging. Multi-tined delivery vehicles that may be used in the present invention include those disclosed in, e.g., McGuckin, Jr. et al., U.S. Pat. Nos. 6,905,480 and 7,331,947, which are incorporated herein by reference.

A further embodiment of the present invention is a method for treating or ameliorating an effect of a solid tumor that has metastasized to one or more sites in a human. This method comprises administering intratumorally to the human a unit dose of C. novyi NT colony forming units (CFUs) comprising at least about $1 \times 10^3$-$1 \times 10^7$ CFUs suspended in a pharmaceutically acceptable carrier or solution. Preferably, at least one site of metastasis is distal to the original solid tumor.

As used herein, "metastasis" and grammatical variations thereof mean the spread of pathogenic cells, i.e. tumor cells, from an original, primary region of the body, to a secondary region of the body. Metastasis may be regional or distal, depending on the distance from the original primary tumor site. Whether a metastasis is regional or distal may be determined by a physician. For example, a breast cancer that has spread to the brain is distal, whereas the spread of breast cancer cells to under arm lymph nodes is regional.

In the present invention, an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts are as disclosed herein or as modified by a medical professional. It is understood by those skilled in the art that the dosage amount will vary with the route of administration, the rate of excretion, the duration of the treatment, the identity of any other drugs being administered, the age and size of the patient, and like factors well known in the arts of medicine. In general, a suitable dose of a composition according to the invention will be that amount of the composition, which is the lowest dose effective to produce the desired effect. The effective dose of a composition of the present invention is described above. Further, a composition of the present invention may be administered in conjunction with other treatments.

The compositions of the invention comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable unit dosage forms by conventional methods known to those of skill in the art. See, e.g., Remington, The Science and Practice of Pharmacy ($21^{st}$ Edition, Lippincott Williams and Wilkins, Philadelphia, Pa.).

Pharmaceutically acceptable carriers or solutions are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier or solution used in a unit dose according to the present invention must be "acceptable" in the sense of being compatible with the other ingredients of the formulation and not injurious to the subject. Carriers or solutions suitable for a selected dosage form and intended route of administration, e.g., IT, are well known in the art, and acceptable carriers or solutions for a chosen dosage form and method of administration can be determined using ordinary skill in the art.

The unit doses of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22) solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Liquid dosage forms include pharmaceutically-acceptable emulsions, microemulsions, liquids, and suspensions. The liquid dosage forms may contain suitable inert diluents commonly used in the art. Besides inert diluents, the oral compositions may also include adjuvants, such as wetting agents, emulsifying and suspending agents, coloring, and preservative agents. Suspensions may contain suspending agents.

Dosage forms for the intratumoral administration include solutions, dispersions, suspensions or emulsions, or sterile powders. The active agent(s)/compound(s) may be mixed under sterile conditions with a suitable pharmaceutically-acceptable carrier.

Unit doses of the present invention may alternatively comprise one or more active agents, e.g., *C. novyi* CFUs or C. novyi NT spores in combination with sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

Intratumorally injectable depot forms may be made by forming microencapsulated matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the active agent in liposomes or microemulsions which are compatible with body tissue.

As noted above, the formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods of the present invention. These examples are illustrative only and are not intended to limit the scope of the invention in any way.

EXAMPLES

Example 1

Combined Intravenous (IV) Dosing of C. novyi NT with Radiation

A study of a single IV dose of C. novyi NT spores in dogs with spontaneous tumors following treatment with external beam radiation was performed.

The manufacturing and final formulation of C. novyi NT spores was performed by the Johns Hopkins Development laboratory according to the following process. C. novyi NT spores generated according to Dang et al., 2001. were inoculated into a rich sporulation medium and incubated in an anaerobic chamber for 17-19 days at 37° C. Spores were purified by sequential continuous Percoll gradient centrifugation followed by extensive phosphate buffered saline washing. Spores were stored at 2-8° C. Spores were prepared prior to shipment, suspended in sterile phosphate buffered saline and diluted in 50 ml of 0.9% sodium chloride.

C. novyi NT spores were reconstituted in a 50 ml saline bag and delivered overnight to the test site. The radiation dose was approximately 54 gy delivered over 20 fractions: 11 before C. novyi NT IV injection and 9 after injection. C. novyi NT spores were administered as a single injection at a dose of $1\times10^9$ spores/m$^2$, based on body surface area. The transfer of the spores to a syringe occurred on an absorbent pad with an impervious backing. A 22 gauge needle with a 3-way stopcock attached was inserted into the bag. A male portion of a closed chemotherapy system (ONGUARD™, TEVA Medical Ltd.) was attached to a port on the stopcock. The complete contents were withdrawn from the bag into a 60 cubic centimeter (cc) syringe to which was attached a female portion of the closed system. The spores were injected into each subject over 15 minutes through an IV catheter to which was attached the male end of the chemotherapy closed system. The infusion was followed by a 10 cc saline flush. The subject was monitored closely for 6 hours post-infusion as follows: vital signs, blood pressure, and oxygen saturation monitoring every 15 minutes for the first 60 minutes, followed by monitoring every 30 minutes for the next 60 minutes, then every 60 minutes for the next 120 minutes. Subsequent checks were performed every 60 minutes for a total of 6 hours.

Test subjects were hospitalized for the initial 3 weeks of treatment: 2 weeks for radiation treatments and 1 week following C. novyi NT IV treatment. Subsequent follow-up visits occurred up to 6 months post-treatment at month 1, 2, 3, and 6. See Tables 1 and 2 for sample treatment schedules.

TABLE 1

| | Screen (Prior to starting radiation therapy) | Day 1 In-Patient Monitoring for 6 Hours Post Infusion | Day 2 | Day 3 | Day 4 | Day 5 | Day 8 ± 2 days | Day 15 ± 2 days | Month 1 ± 3 days | Month 2 ± 3 days | Month 3 ± 14 days | Month 6 ± 14 days |
|---|---|---|---|---|---|---|---|---|---|---|---|---|
| Informed Consent | X | | | | | | | | | | | |
| Medical History | X | | | | | | | | | | | |
| Physical Exam | X | X | X | X | X | X | X | X | X | X | X | X |
| Vital Signs | X | X | X | X | X | X | X | X | X | X | X | X |
| Chest x-Ray | X | | | | | | X [1] | X [1] | X [1] | X [1] | X [1] | X [1] |
| Tumor fine needle aspiration (FNA) for culture | | | X | X | X | X | X | | | | | |
| Abdominal Ultrasound | X | | | | | | X [1] | X [1] | X [1] | X [1] | X [1] | X [1] |
| Extremity x-Ray (if indicated) | X | | | | | | X [1] | X [1] | X [1] | X [1] | X [1] | X [1] |

TABLE 1-continued

Schedule of spore events

| | Screen (Prior to starting radiation therapy) | Day 1 In-Patient Monitoring for 6 Hours Post Infusion | Day 2 | Day 3 | Day 4 | Day 5 | Day 8 ± 2 days | Day 15 ± 2 days | Month 1 ± 3 days | Month 2 ± 3 days | Month 3 ± 14 days | Month 6 ± 14 days |
|---|---|---|---|---|---|---|---|---|---|---|---|---|
| Complete blood count (CBC), Prothrombin time/Partial thromboplastin time (PT/PTT), Chem, Urinalysis | X | X | | X | | X | X | X | X | X | X | X |
| Research bloodwork[2] | X | X | X | X | X | X | X | X | X | X | X | X |
| Tumor measurements and photographs | | X | | X | | X | X | X | X | X | X | X |
| Infuse C. novyi NT spores | | X | | | | | | | | | | |
| Response | | | | | | | X | X | X | X | X | X |
| Adverse Events (AEs) | | X | | X | | X | X | X | X | X | X | X |
| Con Meds | X | X | | X | | X | X | X | X | X | X | X |

[1] Chest x-ray and additional imaging as clinically indicated
[2] Research lab work includes plasma, serum, whole blood pellet, and peripheral blood mononuclear cell collection (cells from plasma collection)

TABLE 2

Calendar of treatments for combined radiation and C. novyi NT (Days)

| Monday | Tuesday | Wednesday | Thursday | Friday | Saturday | Sunday |
|---|---|---|---|---|---|---|
| Radiation Day 1 | Rad Day 2 | Rad Day 3 | Rad Day 4 | Rad Day 5 | | |
| Rad Day 6 | Rad Day 7 | Rad Day 8 | Rad Day 9 | Rad Day 10 | | |
| Spore day 1 X Infusion X | Rad Day 11 Spore Day 2 A Y | Rad Day 12 Spore Day 3 X | Rad Day 13 Spore Day 4 Y | Rad Day 14 Spore Day 5 X | Spore Day 6 | Spore Day 7 |
| Rad Day 15 Spore Day 8 X, Y Spore Day 15 X, Y | Rad Day 16 Spore Day 9 | Rad Day 18 B Spore Day 10 Spore Day 30 X, Y | Rad Day 19 B Spore Day 11 | Rad Day 20 B Spore Day 12 Via CT tumor Re-evaluation 60 days post rad | Spore Day 13 | Spore Day 14 Spore Day 90 X, Y |
| Spore Day 180 X, Z | | | | | | |

A Radiation may be interrupted more than one day but will be radiation Day 11 when re-started
B Radiation will be completed one of these days.
X = CBC, Chem Profile, AST, PT/PTT, Research Blood Samples, Adverse Events (AEs), Concomitant Medications, Tumor Measurements, Photos
Y = Research blood samples
Z = Thoracic metastasis Check and additional Imaging as Indicated Including Abdominal Ultrasound As of Sep. 10, 2012, five dogs were treated in this manner. Of the five, 2 developed an abscess, 1 maintained stable disease, and 2 died or were euthanized. The two test subjects that developed an abscess were photographed throughout treatment as shown in FIGS. 1A and 1B.

FIG. 1A depicts a canine osteosarcoma located on the right distal radius/ulna over the course of treatment. The test subject, Sasha, exhibited fever and swelling on day 3 and a burst abscess on day 6. Antibiotics were started on day 8 due to the open wound and later, necrotic bone and tissue were removed. Sasha completed 12 of the 19 radiation treatments and, as of Sep. 10, 2012, was healing with stable disease.

Figure 1B:
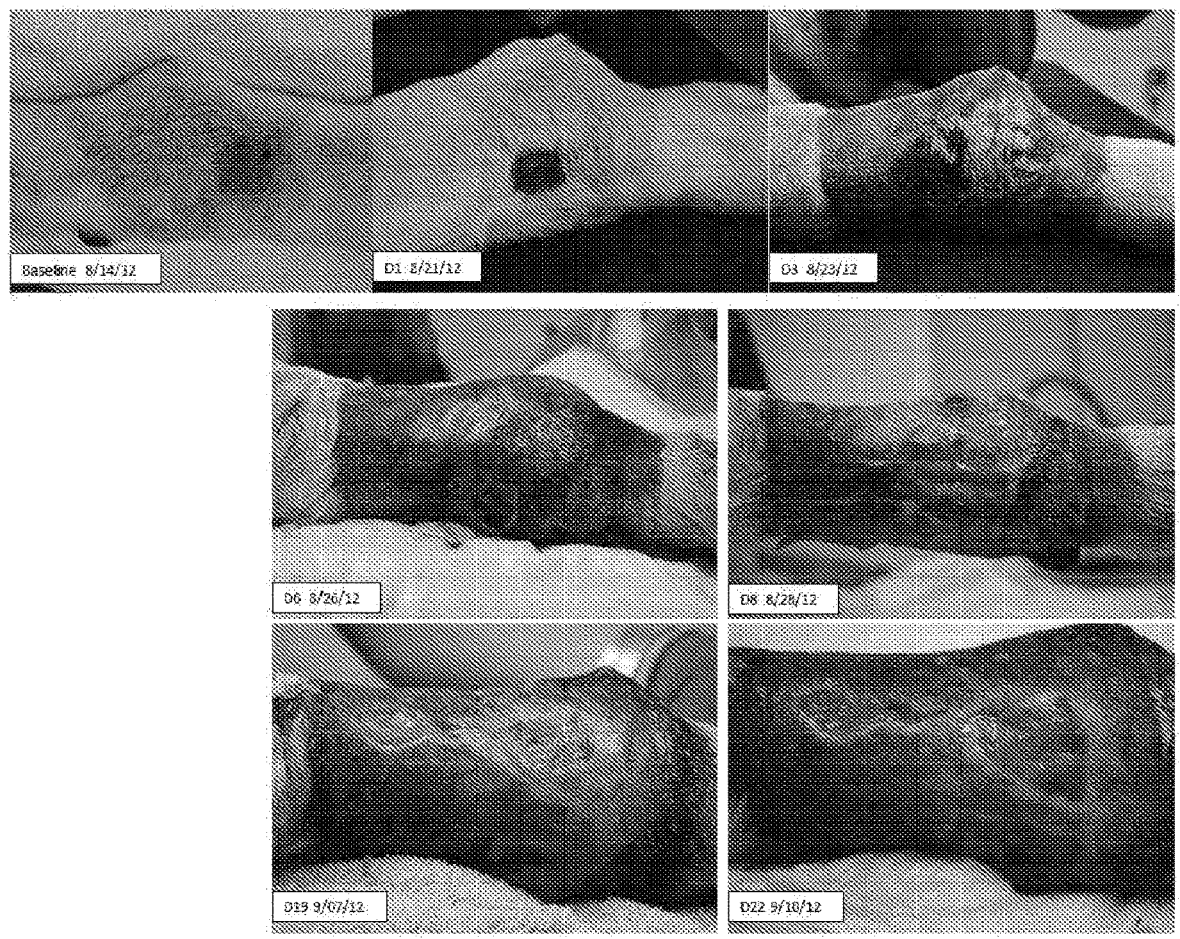

FIG. 1B also depicts a canine osteosarcoma located on the right distal radius/ulna over the course of treatment. The test subject, Sampson, exhibited fever and swelling on day 5. On day 6, the abscess was lanced and antibiotics were started. Sampson completed 14 of the 20 radiation treatments and, as of Sep. 10, 2012, was healing with stable disease.

The other subjects, Chipper, Bailey, and Ruskin, exhibited varying results. Chipper presented with a squamous cell carcinoma of the left mandible. Over the course of treatment, Chipper had swelling at the tumor site and received 20 of 20 radiation treatments. As of Sep. 10, 2012, Chipper had stable disease.

Another subject, Bailey, presented with a soft tissue sarcoma of the left axillary region. During treatment, Bailey died, having experienced sepsis, acute renal failure, potential disseminated intravascular coagulation, and cardiac arrest. However, necropsy showed all dead tissue inside the tumor, with no tumor cells.

The remaining subject, Ruskin, presented with an osteosarcoma of the right proximal humerus. During treatment, Ruskin had swelling of the tumor site and completed 20/20 radiation treatments. However, on day 30, the tumor site was producing large amounts of purulent material and Ruskin was experiencing renal failure. The owner decided to euthanize when renal status did not improve. As of Sep. 10, 2012, necropsy results were still pending.

Example 2

**IT-Injected *C. novyi*-NT Spores Specifically Target Tumor Tissue and Prolong Survival in Rats—Methods**

Cell Lines and Tissue Culture

A rat F98 glioma cell line transfected with a luciferase construct via lentivirus was maintained in Dulbecco's Modified Eagle Medium (DMEM) supplemented with 10% fetal bovine serum (FBS) and 1% penicillin and streptomycin.

Rat Experiments 6 week old female F344 Fisher rats (weight 100-150 grams) were purchased from the National Cancer Institute. For the implantation procedure, female F344 Fisher rats were anesthetized via intraperitoneal (IP) injection of ketamine hydrochloride (75 mg/kg; 100 mg/mL ketamine HCl; Abbot Laboratories), xylazine (7.5 mg/kg; 100 mg/mL Xylaject; Phoenix Pharmaceutical, Burlingame, Calif.), and ethanol (14.25%) in a sterile NaCl (0.9%) solution. F98 glioma cells ($2 \times 10^4$) were stereotactically implanted through a burr hole into the right frontal lobe located 3 mm lateral and 2 mm anterior to the bregma, as described before (Bai, et al., 2011). Tumor size was assessed via a Xenogen instrument with IP injection of 8 mg/rat D-luciferin potassium salt at day 12 after implantation of the tumor cells. Subsequently, 3 million *C. novyi*-NT spores, produced as previously described (Dang, et al., 2001, Bettegowda, et al., 2006), were stereotactically injected into the intracranial tumor using the same coordinates as described above and the rats were treated with 10 mg/kg/day of IP dexamethasone for the first 2 days. Animals were observed daily for any signs of deterioration, lethargy, neurotoxicity, or pain in accordance with the Johns Hopkins Animal Care and Use Guidelines. If symptoms of distress were present, supportive therapy with hydration and doxycycline (loading dose of 15 mg/kg IP followed by 10 mg/kg every 12 hours as maintenance) was initiated and continued for a 7 day period. If symptoms persisted and/or resulted in debilitation, moribund animals were euthanized. The effectiveness of IT injected *C. novyi*-NT spores was evaluated by Kaplan-Meyer survival curves, as well as remaining tumor burden on brain sections. For the latter, brains were collected postmortem, placed in formaldehyde, and embedded in paraffin for additional pathological studies. Gram-stained slides, counter-stained with safranin, and H&E-slides were obtained according to standard procedure guidelines.

Statistical Analyses

Kaplan-Meier survival curves were created and analyzed with a Mantel-Cox test using GraphPad Prism v.5.00 (GraphPad Software, San Diego, Calif.).

Example 3

**IT-Injected *C. novyi*-NT Spores Specifically Target Tumor Tissue and Prolong Survival in Rats—Results**

Figure 2A:
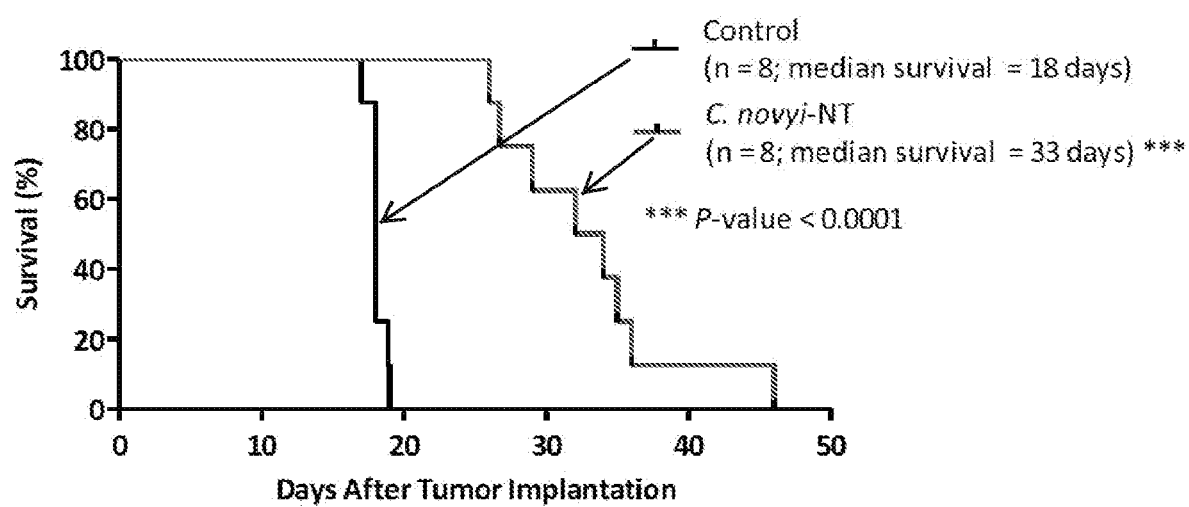
Figure 2B:
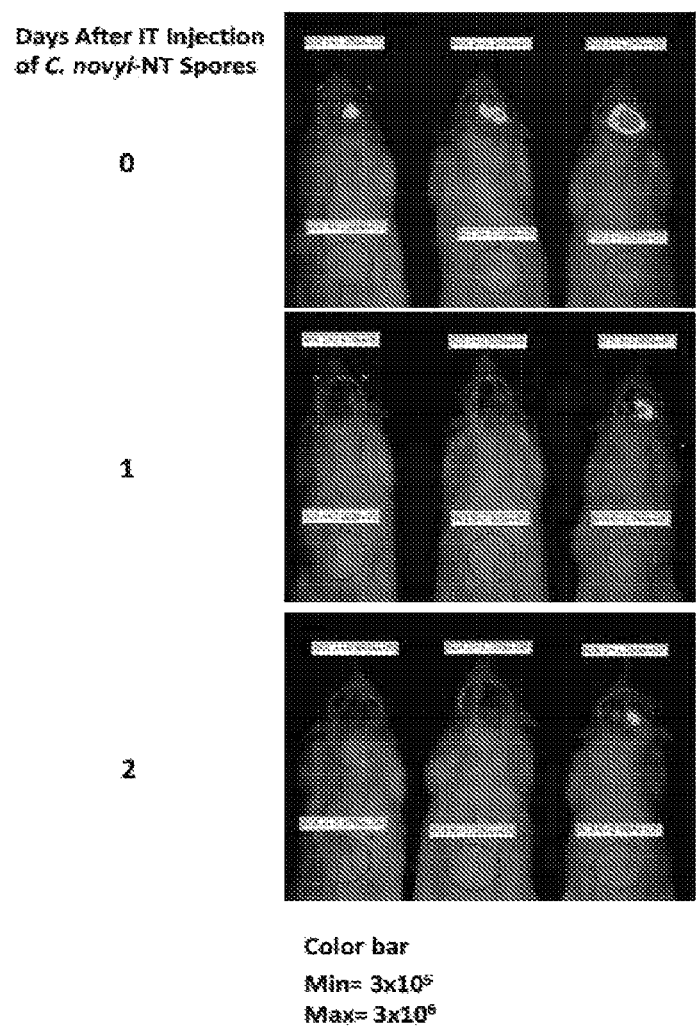
Figure 2C:
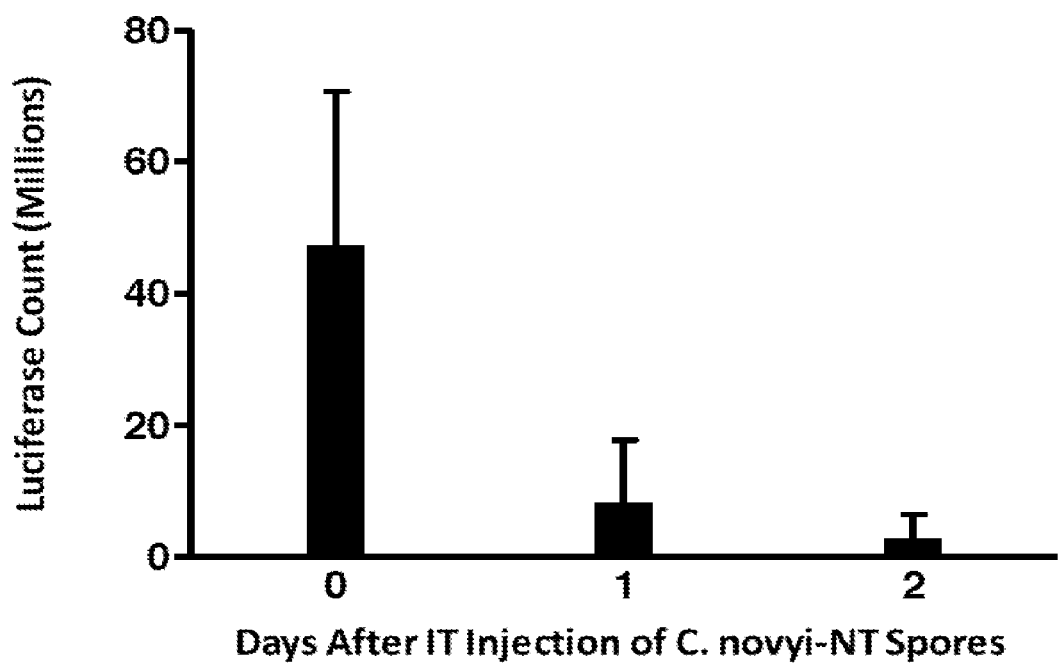
Figure 3A:
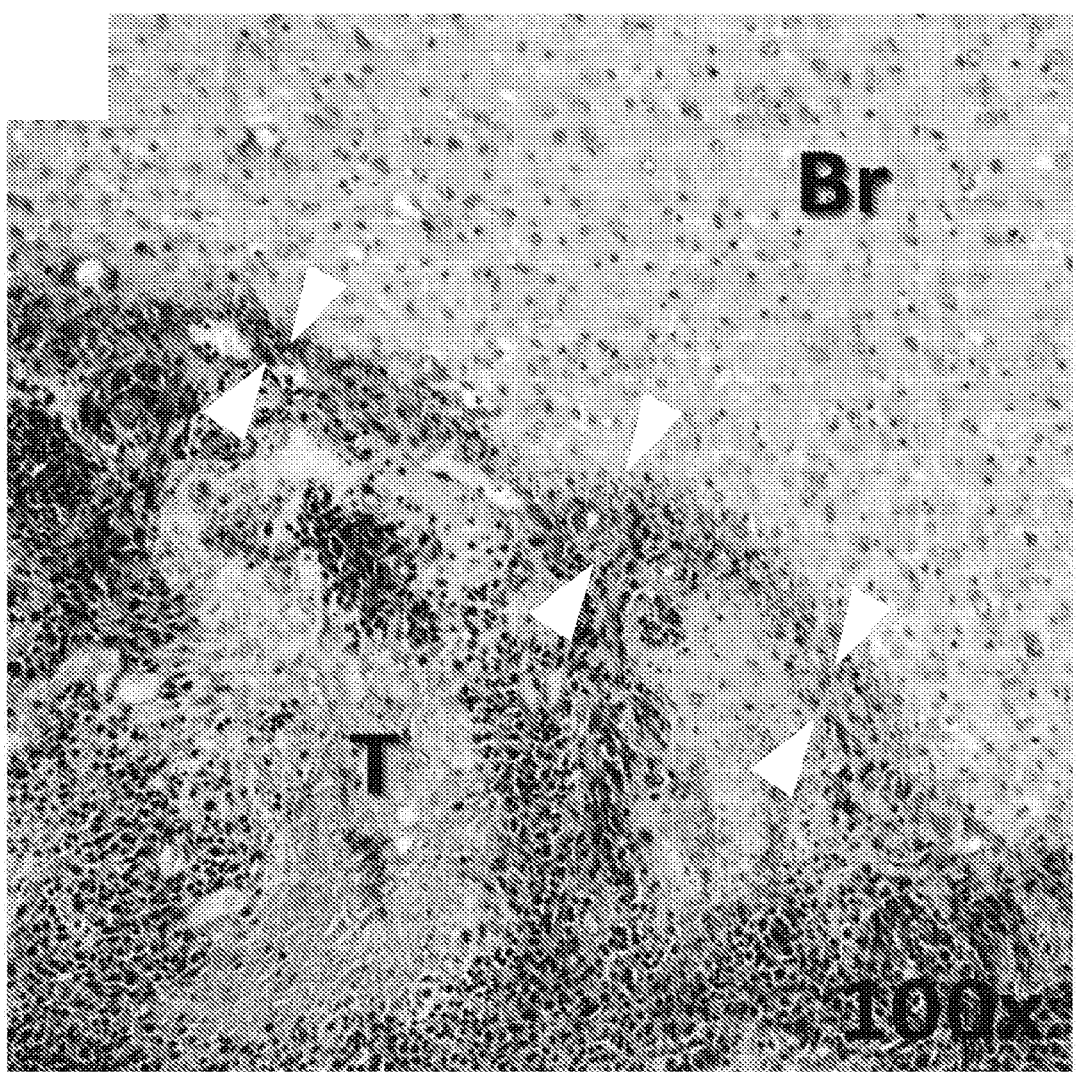
Figure 3B:
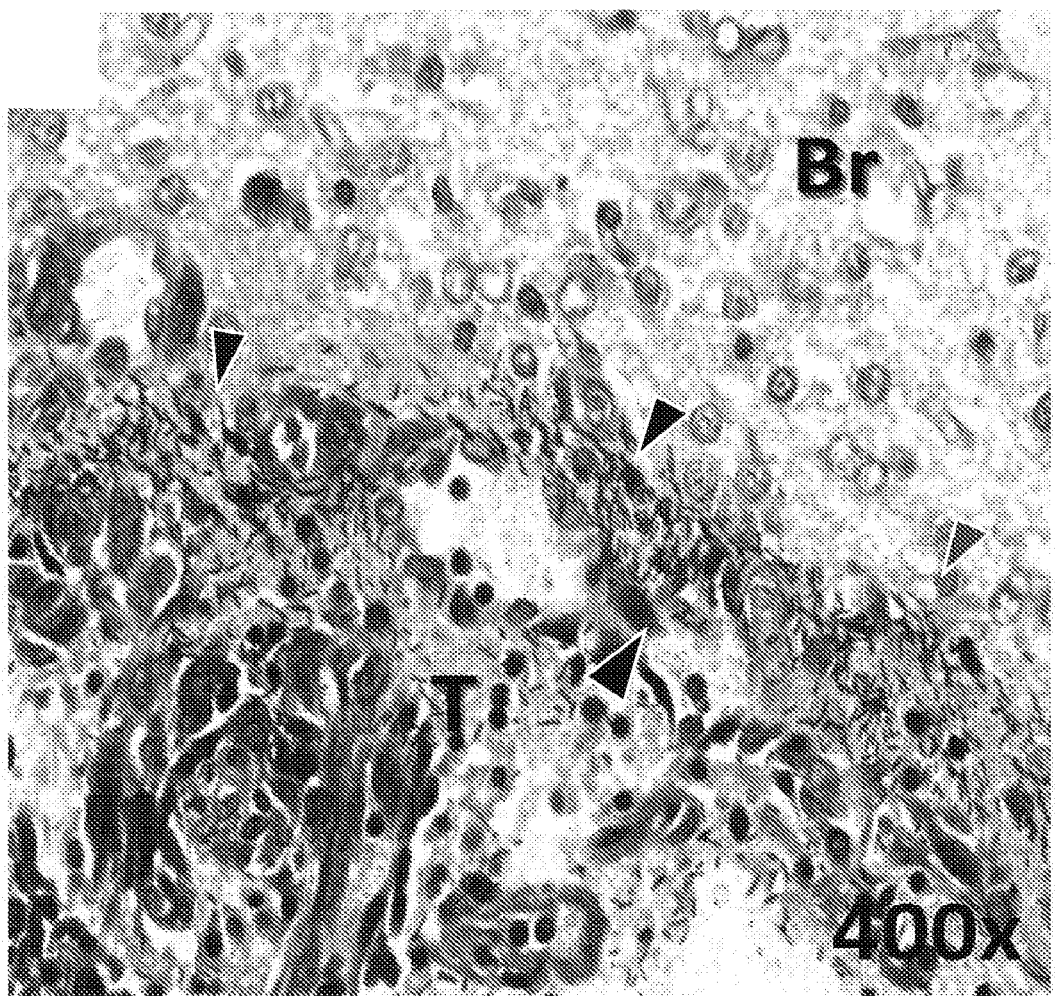
Figure 4A:
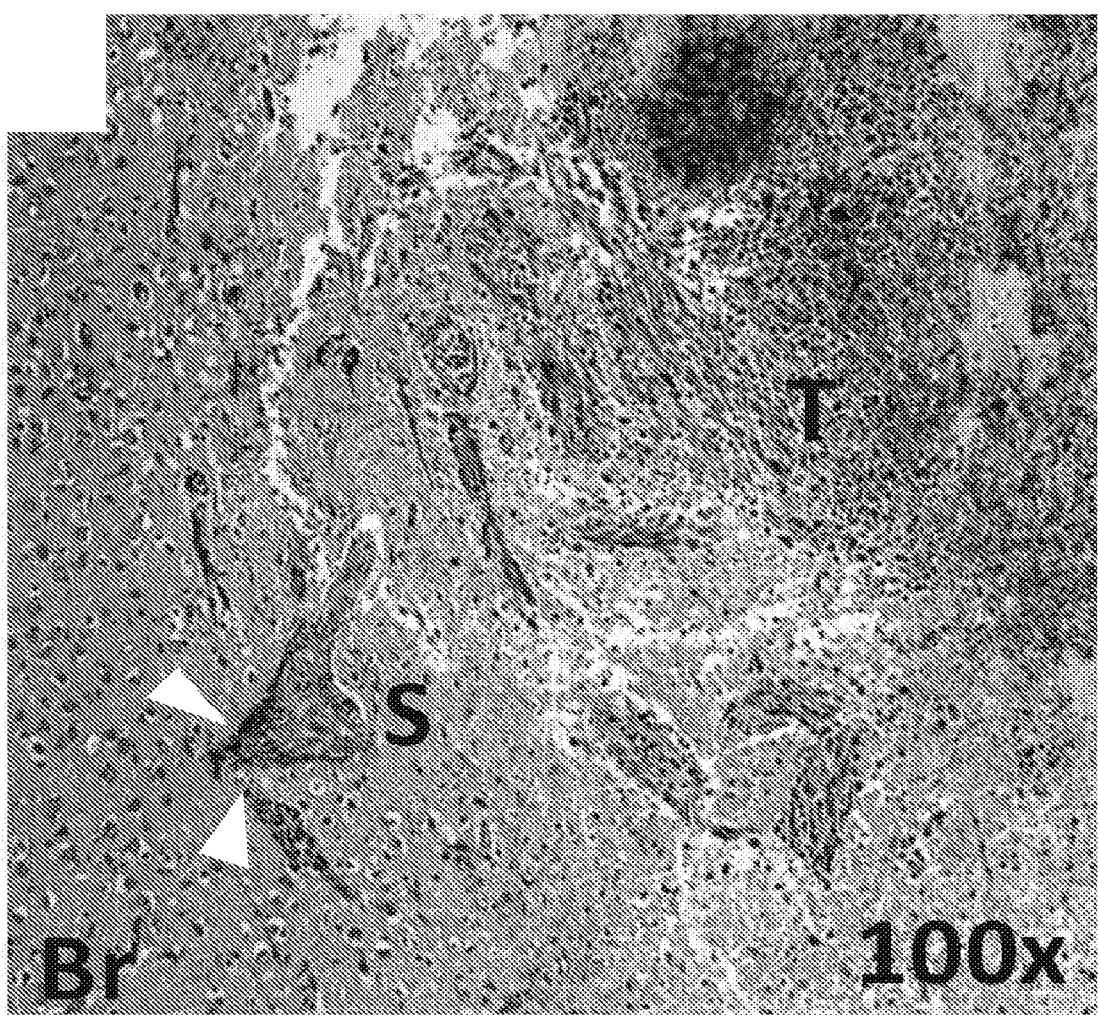
Figure 4B:
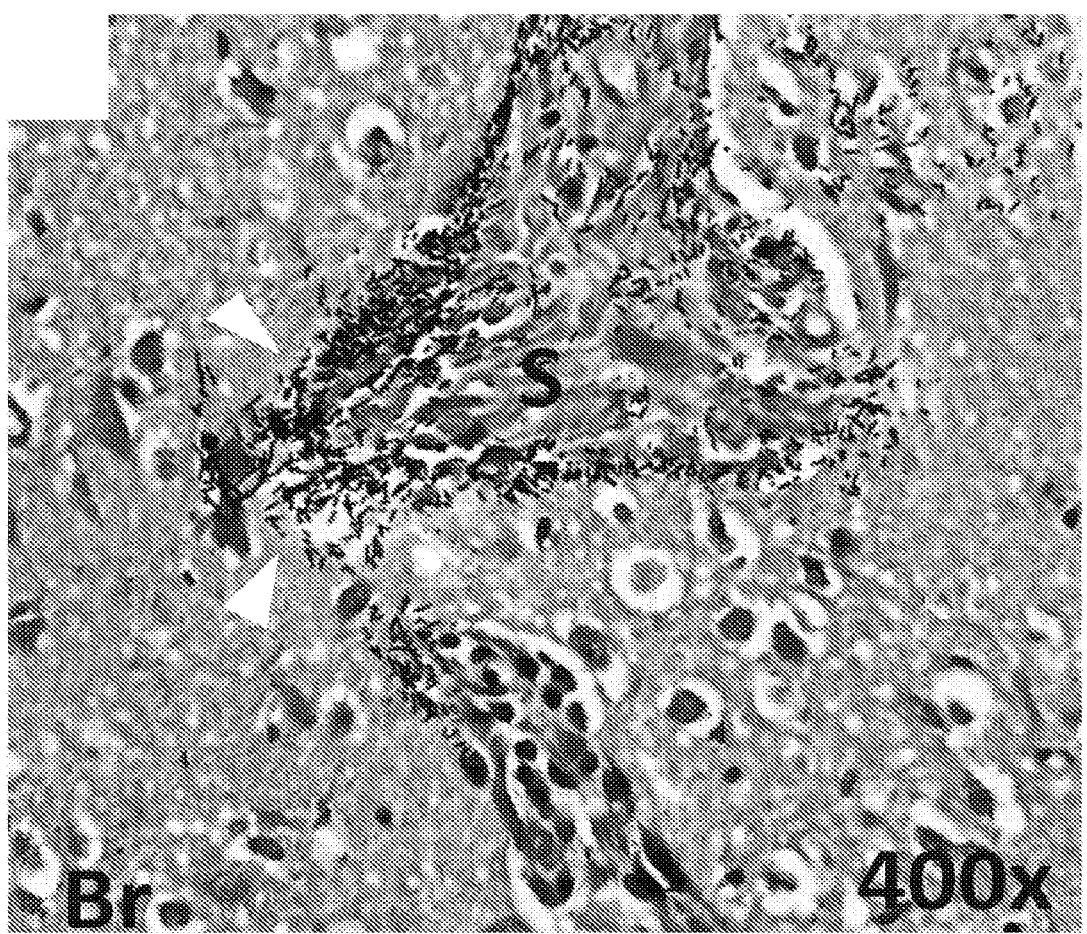
Figure 7A:
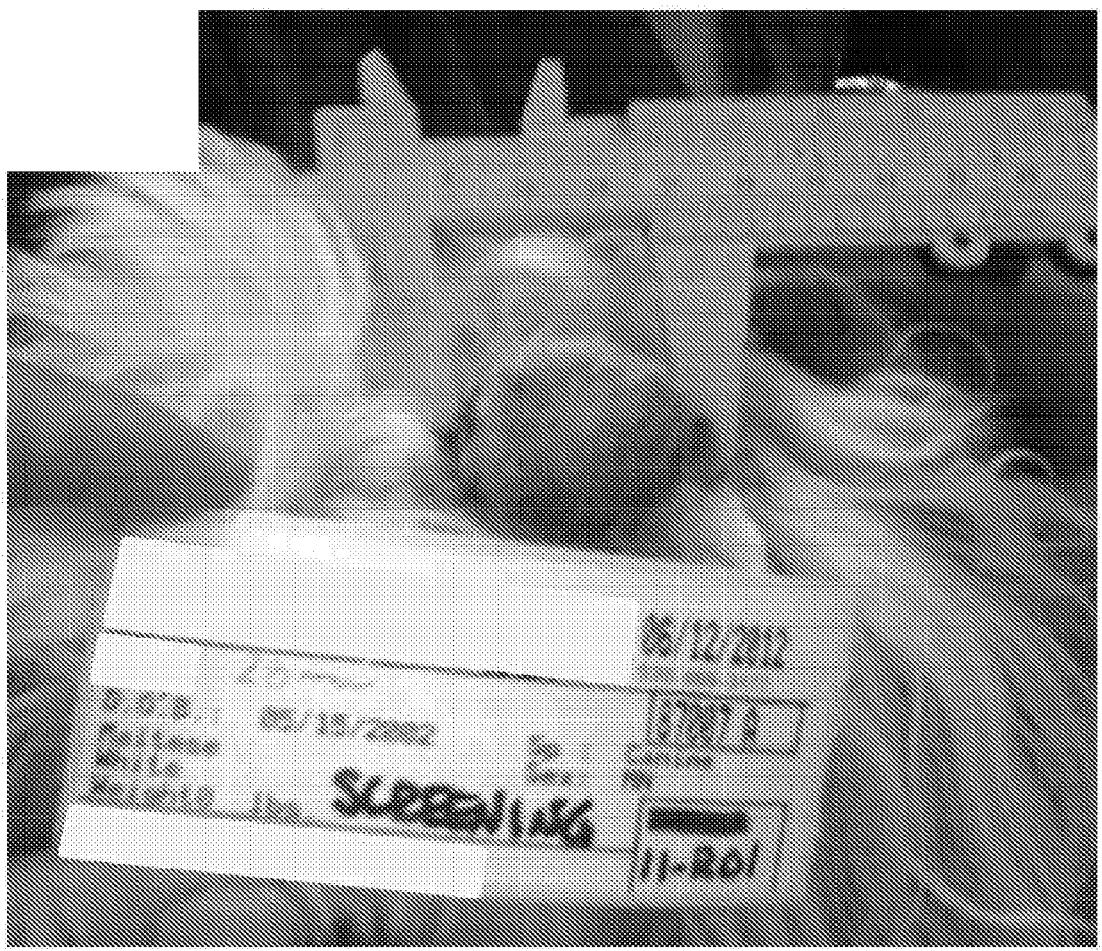
Figure 7B:
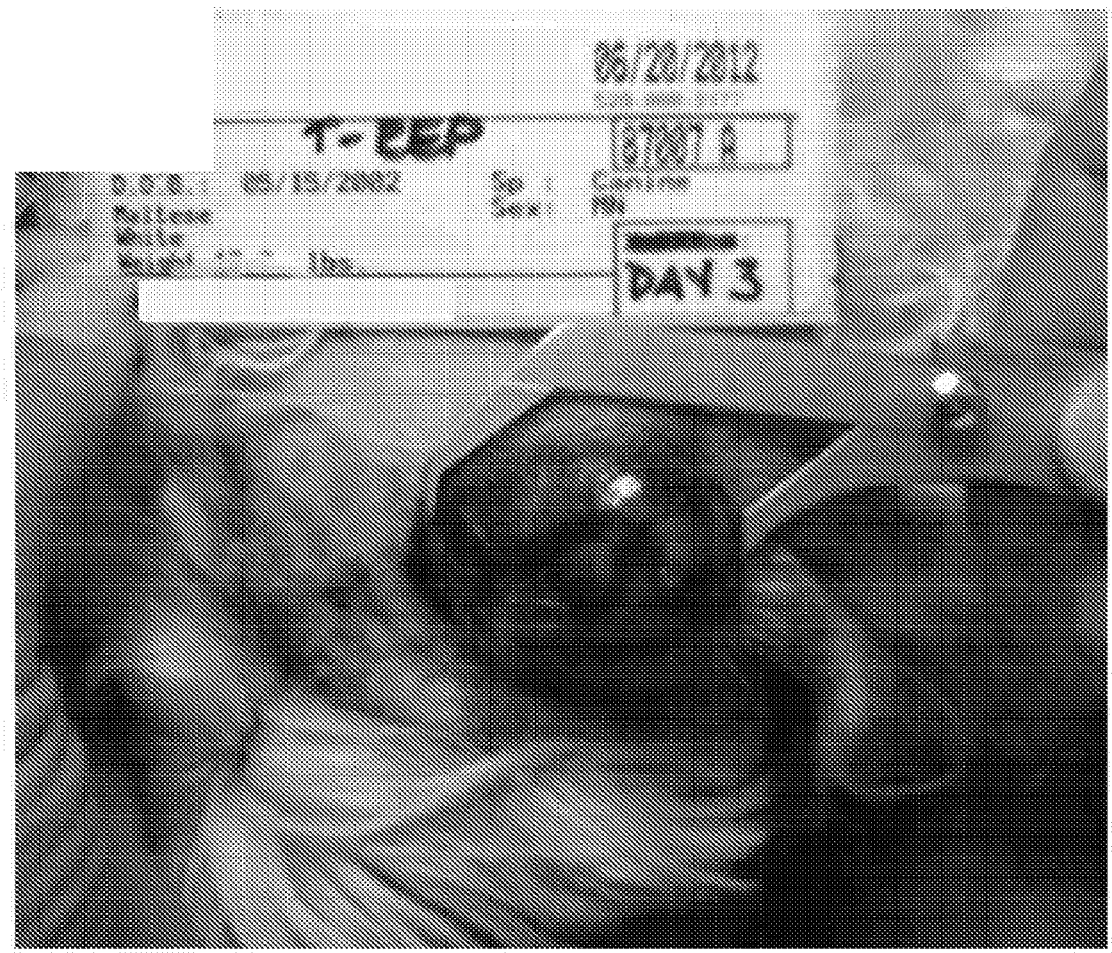
Figure 7C:
Figure 7D:
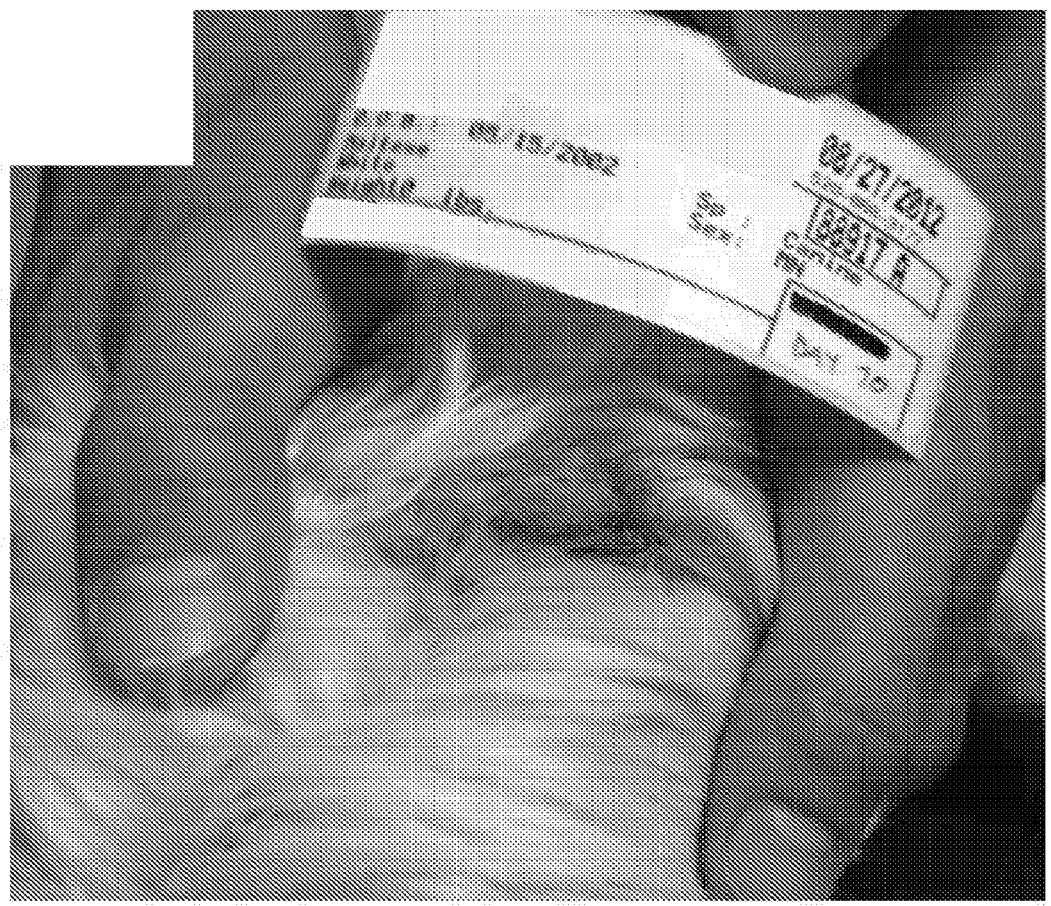
Figure 7E:
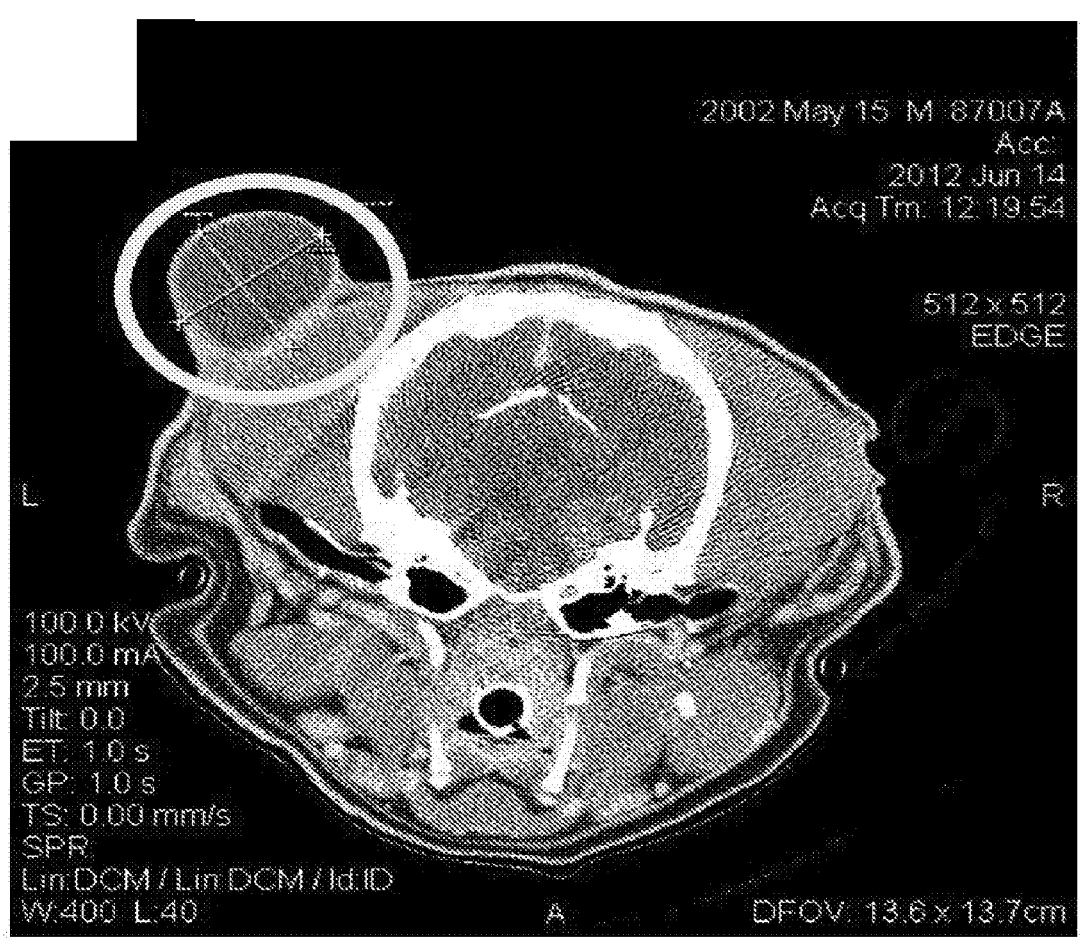
Figure 7F:
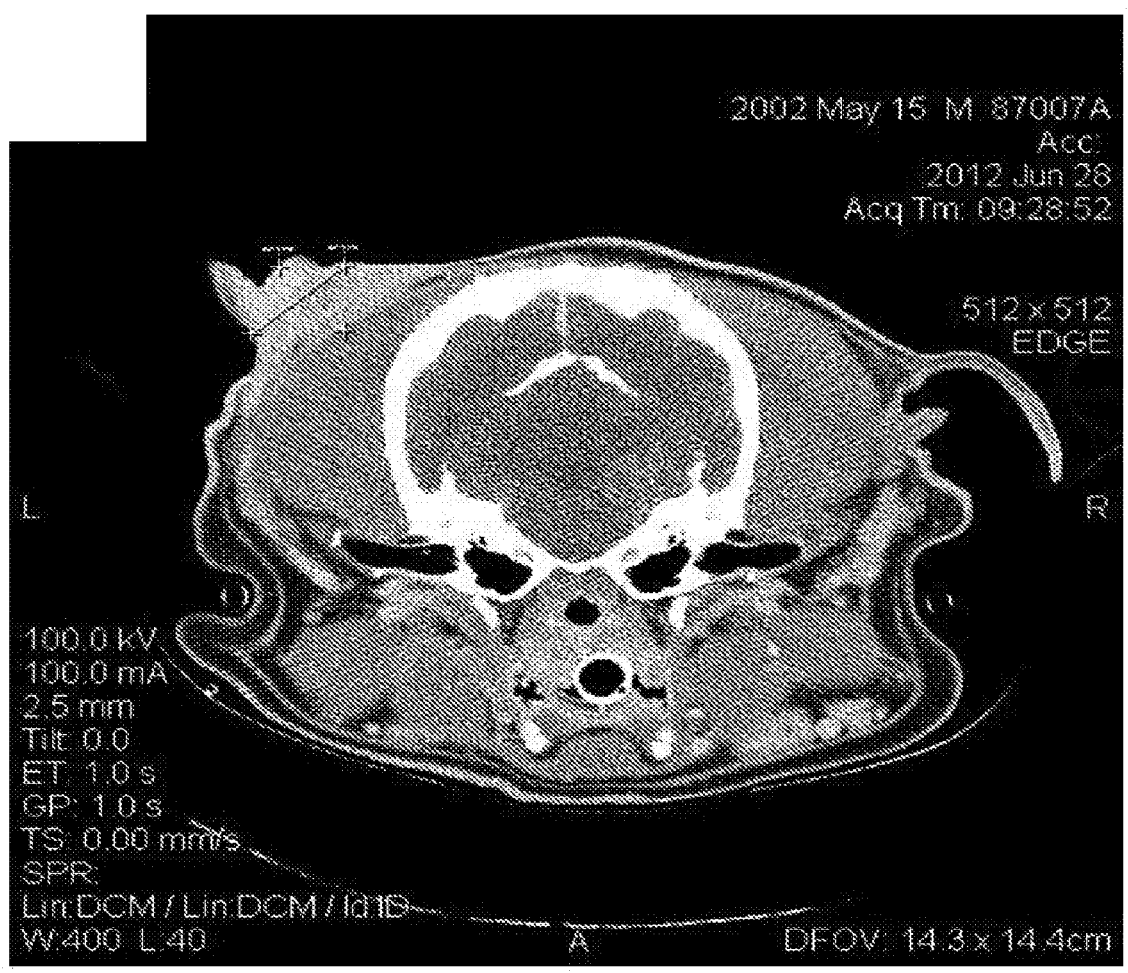
Figure 8A:
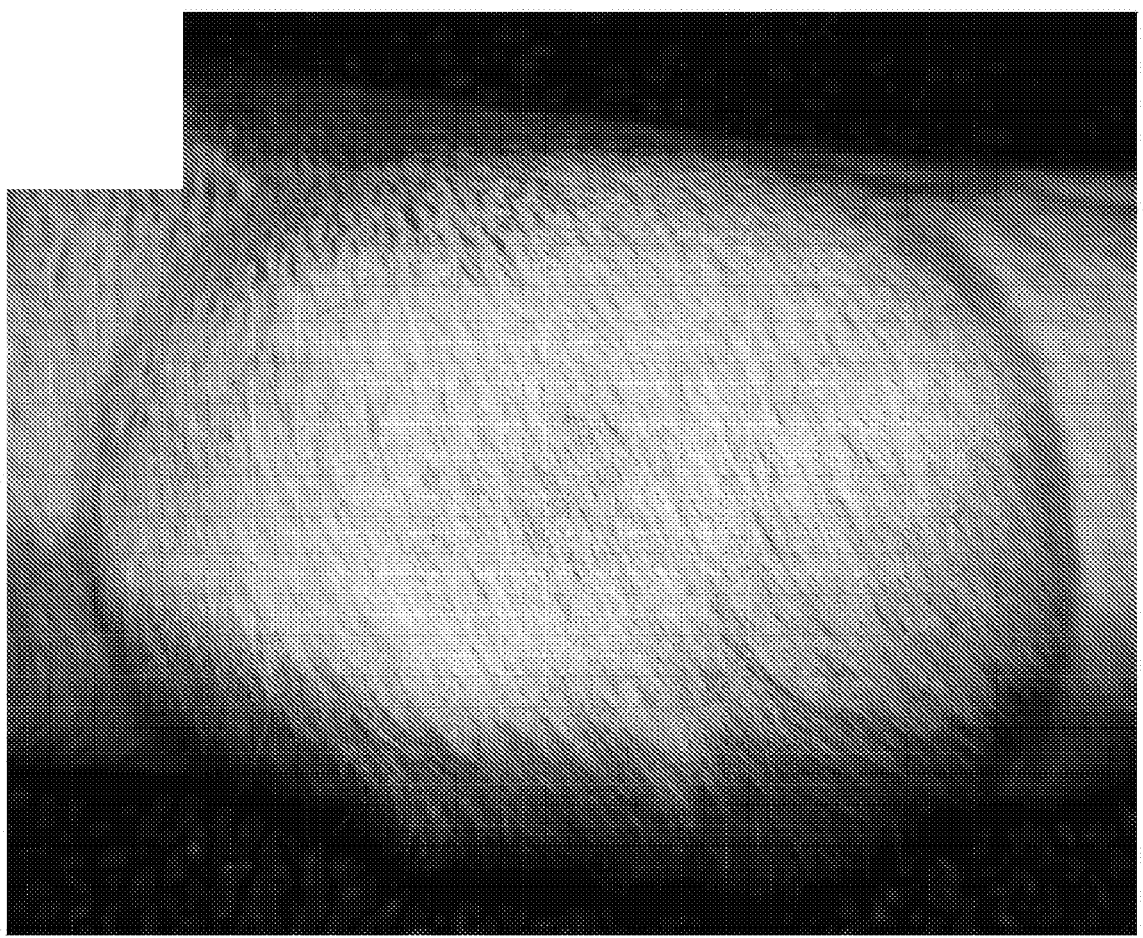
Figure 8B:
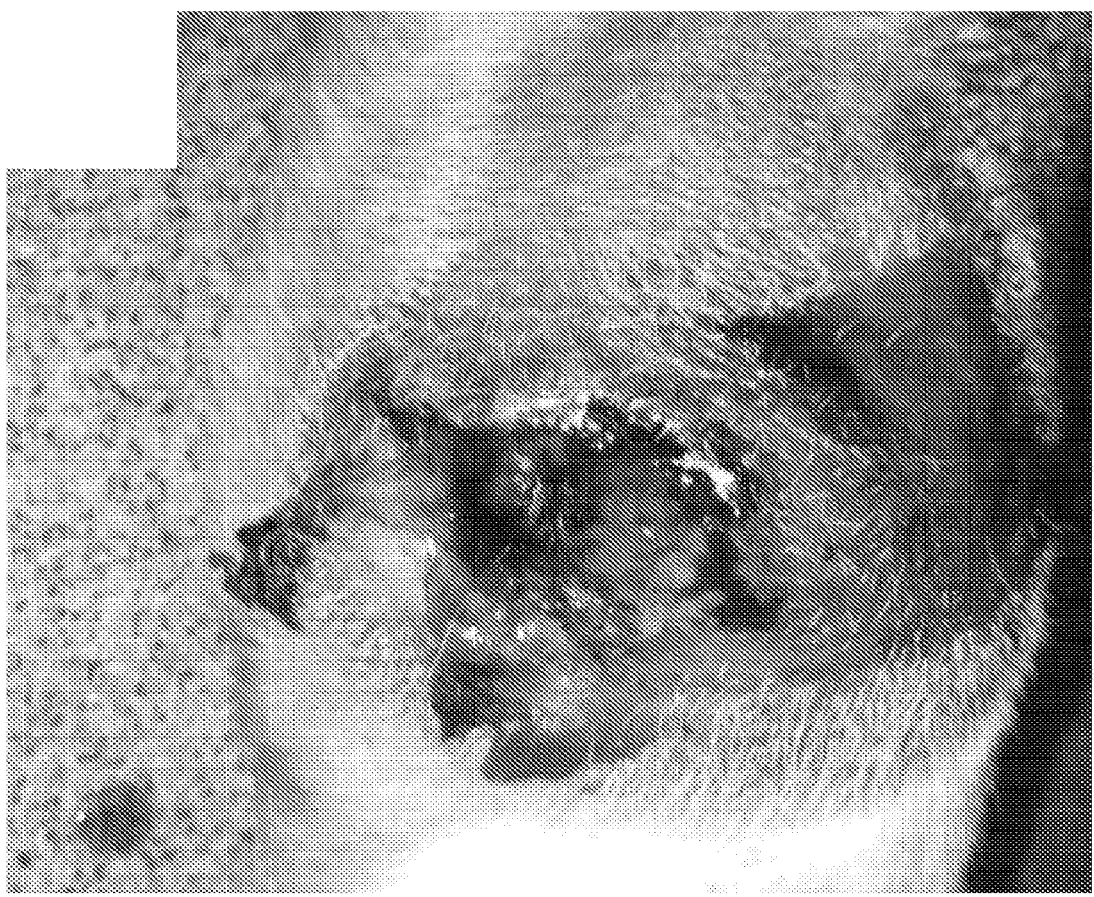
Figure 8C:
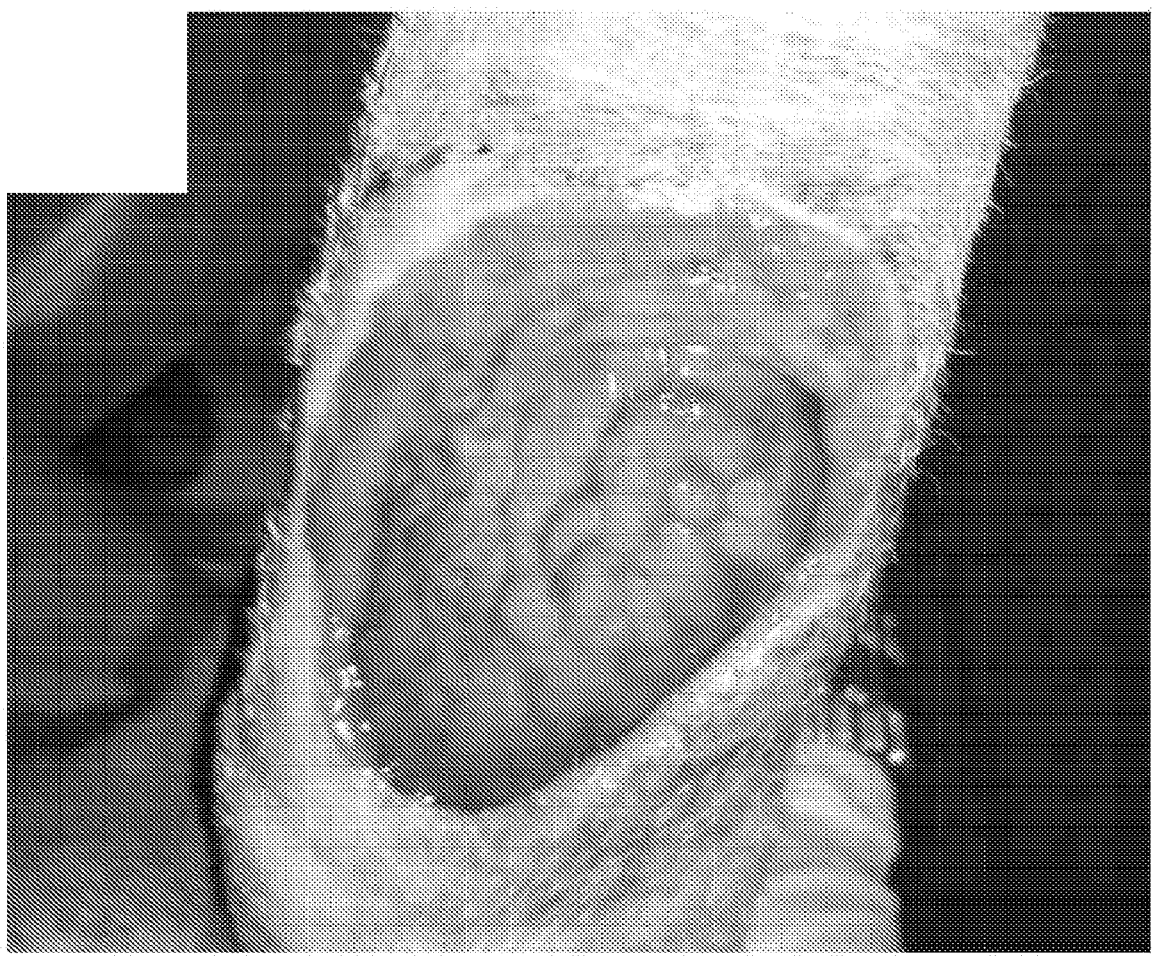
Figure 8D:
Figure 8E:
Figure 8F:
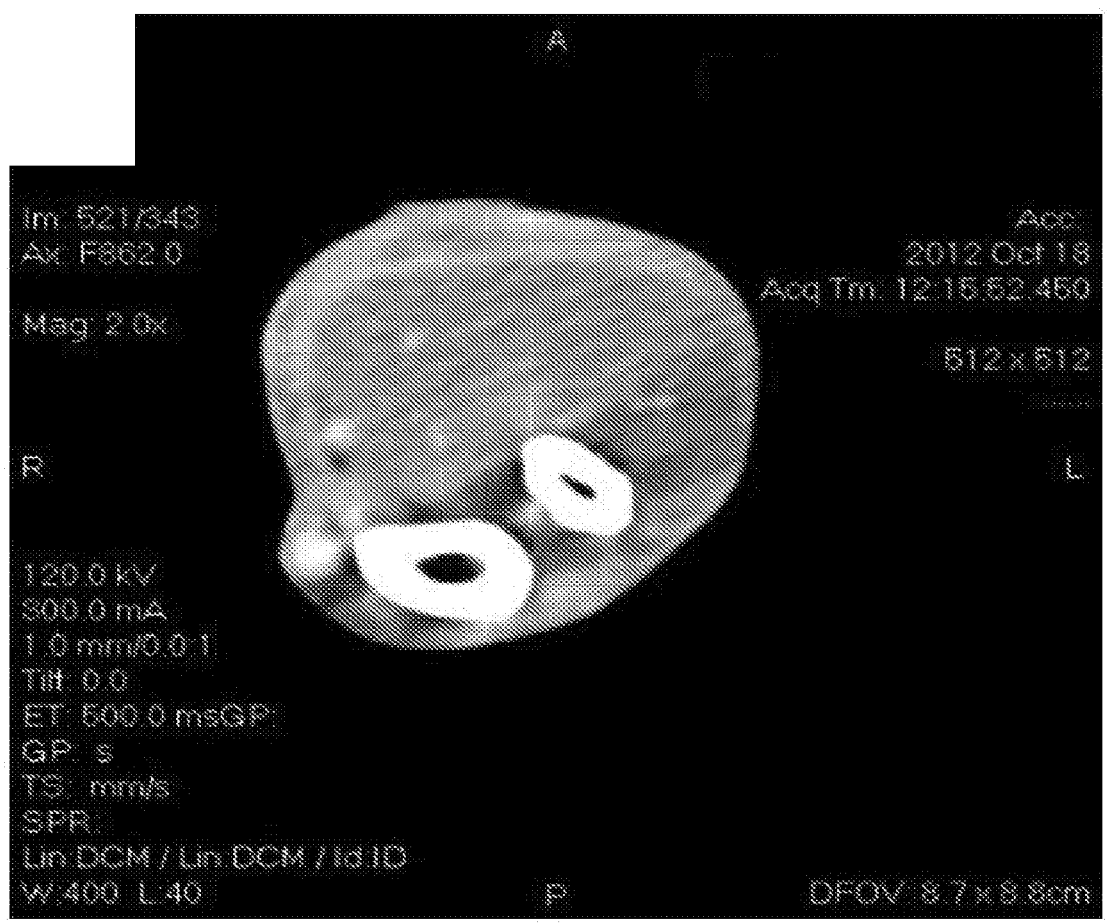

Complete surgical excision of advanced gliomas is nearly always impossible and these tumors inexorably recur. Though this tumor type generally does not metastasize, there are no highly effective medical therapies available to treat it. Gliomas therefore seemed to represent a tumor type for which local injection of *C. novyi*-NT spores could be therapeutically useful. To evaluate this possibility, F98 rat glioma cells were orthotopically implanted into 6-week old F433 Fisher rats, resulting in locally invasive tumors that were rapidly fatal (FIG. 2A). IT injection of *C. novyi*-NT spores into the tumors of these rats resulted in their germination within 24 hours and a rapid fall in luciferase activity, an indicator of tumor burden, over 24-48 hours (FIGS. 2B and 2C). *C. novyi*-NT germination was evidenced by the appearance of vegetative forms of the bacteria. Strikingly, *C. novyi*-NT precisely localized to the tumor, sparing adjacent normal cells only a few microns away (FIGS. 3A and 3B). Moreover, these vegetative bacteria could be seen to specifically grow within and concomitantly destroy islands of micro-invasive tumor cells buried within the normal brain parenchyma (FIGS. 4A and 4B). This bacterial biosurgery led to a significant survival advantage in this extremely aggressive murine model (FIG. 2A, P-value<0.0001).

Example 4

Canine Soft Tissue Sarcomas Resemble Human Tumors—Methods

Genomic DNA Isolation for Sequencing

Genomic DNA from dogs participating in the comparative study of IT *C. novyi*-NT spores was extracted from peripheral blood lymphocytes (PBLs) and formalin-fixed, paraffin-embedded tumor tissue using the QIAamp DNA mini kit (QIAGEN, Valencia, Calif.) according to the manufacturer's protocol.

Sequencing and Bioinformatic Analysis

Genomic purification, library construction, exome capture, next generation sequencing, and bioinformatics analyses of tumor and normal samples were performed at Personal Genome Diagnostics (PGDx, Baltimore, Md.). In brief, genomic DNA from tumor and normal samples were fragmented and used for Illumina TruSeq library construction (Illumina, San Diego, Calif.). The exonic regions were captured in solution using the Agilent Canine All Exon kit according to the manufacturer's instructions (Agilent, Santa Clara, Calif.). Paired-end sequencing, resulting in 100 bases from each end of the fragments, was performed using a HiSeq 2000 Genome Analyzer (Illumina, San Diego, Calif.). The tags were aligned to the canine reference sequence (CanFam2.0) using the Eland algorithm of CASAVA 1.7 software (Illumina, San Diego, Calif.). The chastity filter of the BaseCall software of Illumina was used to select sequence reads for subsequent analysis. The ELAND algorithm of CASAVA 1.7 software (Illumina, San Diego, Calif.) was then applied to identify point mutations and small insertions and deletions. Known polymorphisms recorded in dbSNP131 (CanFam2.0) were removed from the analysis. Potential somatic mutations were filtered and visually inspected as described previously (Jones, et al., 2010).

Example 5

Canine Soft Tissue Sarcomas Resemble Human Tumors—Results

Preclinical animal studies of anticancer agents often do not recapitulate the observed effects in people. In dogs, however, clinically used therapeutic agents induce similar toxicities and effects to people (Paoloni, et al., 2008). Studies of investigational therapies in dogs can represent a crucial bridge between preclinical animal studies and human clinical studies. In particular, canine soft tissue sarcomas are an excellent model as they are common in many breeds of dogs and have clinical and histopathologic features remarkably close to those of human soft tissue sarcomas (Paoloni, et al., 2008, Vail, et al., 2000). However, while recent advances in genomics have significantly expanded our knowledge of cancer genetics in people, comparatively little is known about the genetic landscape of canine cancers. Therefore, to determine whether canine tumors were genetically similar to those of humans, the exome of tumor and matched normal DNA from 11 dogs participating in the comparative study was sequenced (FIG. 5). This analysis involved the interrogation of 30,194 nominal genes comprising 32.9 megabases (Mb) of DNA. Ten of the dogs had soft tissue sarcomas (six peripheral nerve sheath tumors) and one had a chondroblastic osteosarcoma. On average, 15.7 gigabases (Gb) (range: 8.1-23.3 Gb) of generated sequence were mapped to the genome, and 92.1% of bases in the targeted regions were covered by at least 10 unique reads in the tumor DNA. Similarly, an average of 16.3 Gb (range: 14.6-19.7 Gb) of sequence were mapped to the genome in normal DNA, with 93.6% of targeted bases covered by at least ten unique reads. Average coverage for each targeted base in the tumor was 153-fold (range: 73-227-fold) and was 152-fold in the matched normal samples (range: 130-178-fold).

Using stringent analysis criteria, 156 somatic mutations and 28 somatic copy number alterations among the 10 soft tissue sarcomas were identified (Table 3 and FIG. 6). The range of somatic mutations was 0 to 95 with a mean of 14 per tumor. Mutation prevalence in the soft tissue sarcomas was low, averaging 0.47 per Mb (range: 0.00-2.89 per Mb). Excluding one sample outlier, with 95 somatic alterations, there was a mean prevalence of 0.21 mutations per Mb (range: 0.00-0.61 per Mb) (FIG. 5), similar to estimates of the mutation rate in human pediatric rhabdoid tumors (Lee, et al., 2012) and other soft tissue sarcomas (Joseph, et al., 2013). The most common type of somatic alteration was a missense mutation, with a preponderance of C to T (45.5%) and G to A transitions (34.0%; Tables 4a and 4b).

TABLE 3

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| 04-R03 | STS | CCDC61 | coiled-coil domain containing 61 | ENSCAFT00000006986 | chr1_112524782-112524782_C_T | NA | Substitution | Splice site donor | CCCTANCTGGG (SEQ ID NO: 1) | 0.41 |
| | | FAM83B | family with sequence similarity 83, member B | ENSCAFT00000003643 | chr12_25277449-25277449_G_T | 68V > F | Substitution | Nonsynonymous coding | AAAACNTCCAG (SEQ ID NO: 2) | 0.39 |
| | | Novel Gene | uncharacterized protein | ENSCAFT00000006899 | chr23_3005035-3005035_T_A | 32N > I | Substitution | Nonsynonymous coding | GGTCANTATTA (SEQ ID NO: 3) | 0.34 |
| | | Novel Gene | uncharacterized protein | ENSCAFT00000028936 | chr20_55267898-55267898_C_ | 323R > X | Substitution | Nonsense | AGGAGNGACGC (SEQ ID NO: 4) | 0.17 |
| | | NUP210 | nucleoporin 210kDa | ENSCAFT00000007053 | chr20_6644043-6644043_G_T | 1627P > T | Substitution | Nonsynonymous coding | GCCCGNGATGG (SEQ ID NO: 5) | 0.38 |
| | | PLMN | Plasminogen Plasmin heavy chain A Plasmin light chain B | ENSCAFT00000001179 | chr1_52549843-52549843_C_T | 598G > E | Substitution | Nonsynonymous coding | CGCACNCACCT (SEQ ID NO: 6) | 0.28 |
| | | UFSP2 | UFM1-specific peptidase 2 | ENSCAFT00000012105 | chr16_48180970-48180970_T_G | 271L > R | Substitution | Nonsynonymous coding | TTACCNCAATC (SEQ ID NO: 7) | 0.61 |
| | | ZNFX1 | zinc finger, NFX1-type containing 1 | ENSCAFT00000018115 | chr24_38909185-38909185_T_G | 1195I > L | Substitution | Nonsynonymous coding | AACAANGTCAT (SEQ ID NO: 8) | 0.34 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| 16-R03 | STS | ANKRD11 | ankyrin repeat domain 11 | ENSCAFT00000031567 | chr5_67220009-67220009_G_A | NA | Substitution | Splice site donor | CCGTGNT GAGT (SEQ ID NO: 9) | 0.19 |
| | | TMEM132B | transmembrane protein 132B | ENSCAFT00000011029 | chr26_74467030-7467030_C_T | 198G > D | Substitution | Nonsynonymous coding | ACAAGNC GGCC (SEQ ID NO: 10) | 0.18 |
| 16-R02 | STS | CAPN6 | calpain 6 | ENSCAFT00000028872 | chrX_87423838-87423838_C_T | 433R > H | Substitution | Nonsynonymous coding | ATCTGCG GTTC (SEQ ID NO: 11) | 0.45 |
| | | CNGB3 | cyclic nucleotide-gated cation channel beta-3 | ENSCAFT00000014134 | chr29_35801978-35801978_G_A | 451R > X | Substitution | Nonsense | GATTCGG AAGT (SEQ ID NO: 12) | 0.22 |
| | | Novel gene | uncharacterized protein | ENSCAFT00000035928 | chr4_69847894-69847894_C_G | 352Y > X | Substitution | Nonsense | ACCTACT TTGA (SEQ ID NO: 13) | 0.11 |
| | | PLAC8L1 | PLAC8-like 1 | ENSCAFT00000010364 | chr2_43368179-43368179_C_T | 99C > Y | Substitution | Nonsynonymous coding | TGTCACA CTCA (SEQ ID NO: 14) | 0.2 |
| 11-R04 | STS | AIDA | axin interactor, dorsalization associated | ENSCAFT00000021486 | chr38_19939874-19939874_A_G | 258F > S | Substitution | Nonsynonymous coding | AAGCANA GCAC (SEQ ID NO: 15) | 0.25 |
| | | BRWD3 | bromodomain and WD repeat domain containing 3 | ENSCAFT00000027493 | chrX_65189965-65189965_A_C | 275S > A | Substitution | Nonsynonymous coding | AGTTGNT GGAC (SEQ ID NO: 16) | 0.7 |
| | | Novel gene | uncharacterized protein | ENSCAFT00000027037 | chrX_58551749-5851749_A_G | 104K > R | Substitution | Nonsynonymous coding | CCTGANG AATT (SEQ ID NO: 17) | 0.17 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| 11-R02 | STS-PNST | AFAP1L1 | actin filament associated protein 1-like 1 | ENSCAFT00000029078 | chr4_62838379-6288379_G_A | 4255 > F | Substitution | Nonsynonymous coding | TCTTGNAGAAG (SEQ ID NO: 18) | 0.25 |
| | | ATP7B | copper-transporting ATPase 2 | ENSCAFT00000006859 | chr22_3134952-3134952_A_C | 288K > Q | Substitution | Nonsynonymous coding | ACCCANAGATG (SEQ ID NO: 19) | 0.2 |
| | | C11orf63 | chromosome 11 open reading frame 63 | ENSCAFT00000018556 | chr5_14445155-14445155_A_G | 55S > P | Substitution | Nonsynonymous coding | CTGGGNCTTAC (SEQ ID NO: 20) | 0.18 |
| | | FIP1L1 | FIP1 like 1 (S. cerevisiae) | ENSCAFT00000003220 | chr13_48967897-48967897_C_ | NA | Deletion | Frameshift | AGGTANAGCAG (SEQ ID NO: 21) | 0.4 |
| | | KRT23 | keratin 23 (histone deacetylase inducible) | ENSCAFT00000025377 | chr9_25094298-25094298_A_T | 389K > M | Substitution | Nonsynonymous coding | ATCGANGTCAA (SEQ ID NO: 22) | 0.25 |
| | | MLL3 | myeloid/lymphoid or mixed-lineage leukemia 3 | ENSCAFT00000007959 | chr16_18937990-1893T992_TGC_ | 3177QQ > Q | Deletion | In-frame deletion | GCTGTNGCTGC (SEQ ID NO: 23) | 0.11 |
| | | MUC5AC | mucin 5B, oligomeric mucus/gel-forming | ENSCAFT00000015796 | chr18_48561759-485671759_G_A | 3305G > S | Substitution | Nonsynonymous coding | AGACANGCCCC (SEQ ID NO: 24) | 0.12 |
| | | Novel gene | uncharacterized protein | ENSCAFT00000036128 | chr14_61936959-61936959_T | NA | Insertion | Frameshift | CGGTCNCCCAG (SEQ ID NO: 25) | 0.16 |
| | | OR52N1 | olfactory receptor, family 52, subfamily N, member 1 | ENSCAFT00000010210 | chr21_32133356-32133356_C_T | 239A > T | Substitution | Nonsynonymous coding | GAAGGNCTTCT (SEQ ID NO: 26) | 0.28 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | PREX1 | phosphatidylinositol-3,4,5-trisphosphate-dependent Rac exchange factor 1 | ENSCAFT00000017540 | chr24_38467733-38467733_C_T | 96R > H | Substitution | Nonsynonymous coding | AGGCGN GCACA (SEQ ID NO: 27) | 0.29 |
| | | PRPF39 | PRP39 pre-mRNA processing factor 39 homolog | ENSCAFT00000022300 | chr8_25550886-25550886_T_ | NA | Deletion | Frameshift | GAAGANT TTGG (SEQ ID NO: 28) | 0.24 |
| | | Q6W651 | uncharacterized protein | ENSCAFT00000030697 | chr9_50634661-50634661_A_T | 3105 > T | Substitution | Nonsynonymous coding | TTTGGNT TTAT (SEQ ID NO: 29) | 0.27 |
| | | TENM2 | teneurin transmembrane protein 2 | ENSCAFT00000027184 | chr4_46714792-46714792_C_T | 364R > H | Substitution | Nonsynonymous coding | TTCGGNG GCGG (SEQ ID NO: 30) | 0.21 |
| | | ZNF641 | zinc finger protein 641 | ENSCAFT00000014313 | chr27_9390690-9390690_C_T | 363P > S | Substitution | Nonsynonymous coding | CCCCCNC AGTG (SEQ ID NO: 31) | 0.26 |
| 11-R01 | STS-PNST | ACTN2 | actinin, alpha 2 | ENSCAFT00000017321 | chr4_6385028-6385028_C_T | 90G > E | Substitution | Nonsynonymous coding | TTTTTNCT CGG (SEQ ID NO: 32) | 0.24 |
| | | GPR139 | G protein-coupled receptor 139 | ENSCAFT00000028634 | chr6_28316728-28316728_C_T | 132P > L | Substitution | Nonsynonymous coding | CCACCNG CTCA (SEQ ID NO: 33) | 0.27 |
| | | KCNJ16 | potassium inwardly-rectifying channel, subfamily J, member 16 | ENSCAFT00000017085 | chr9_19566120-19566120_G_T | 5G > C | Substitution | Nonsynonymous coding | ATTACNG CAGC (SEQ ID NO: 34) | 0.26 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | KCNJ5 | potassium inwardly-rectifying channel, subfamily J, member 5 | ENSCAFT000 00016271 | chr5_8746471-8746471_C_G | 116G > R | Substitution | Nonsynonymous coding | ATCACNC CGGA (SEQ ID NO: 35) | 0.32 |
| 04-R08 | STS-PNST | A1ILJ0 | serpin peptidase inhibitor, clade A (alpha-1 antiproteinase, antitrypsin), member 1 | ENSCAFT000 00036554 | chr8_66432888-66432888_C_T | 194D > N | Substitution | Nonsynonymous coding | GACATNC TCTA (SEQ ID NO: 36) | 0.42 |
| | | AASS | aminoadipate-semialdehyde synthase precursor | ENSCAFT000 00005673 | chr14_62956632-62956632_C_T | 66G > S | Substitution | Nonsynonymous coding | AATGCNA CCAG (SEQ ID NO: 37) | 0.62 |
| | | ABCB10 | ATP-binding cassette, sub-family B (MDR/TAP), member 10 | ENSCAFT000 00019279 | chr4_12734254-12734254_C_T | 495R > C | Substitution | Nonsynonymous coding | CAGCTNG CCCA (SEQ ID NO: 38) | 0.47 |
| | | ACTL9 | actin-like 9 | ENSCAFT000 00029470 | chr20_56179685-56179685_G_A | 363P > S | Substitution | Nonsynonymous coding | GGGGGN CAGGC (SEQ ID NO: 39) | 0.37 |
| | | ADAM7 | ADAM metallopeptidase domain 7 | ENSCAFT000 00014408 | chr25_35952270-35952270_C_T | 473E > K | Substitution | Nonsynonymous coding GGAA | CACTTNA (SEQ ID NO: 40) | 0.31 |
| | | ADCYAP1R1 | adenylate cyclase activating polypeptide 1 (pituitary) receptor type I | ENSCAFT000 00005018 | chr14_46708954-46708954_C_T | 4485 > F | Substitution | Nonsynonymous coding | GGGCTNC TTCC (SEQ ID NO: 41) | 0.63 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | ALDH7A1 | aldehyde dehydrogenase 7 family, member A1 | ENSCAFT00000000904 | chr11_18836811-18836811_G_A | 523T > I | Substitution | Nonsynonymous coding | TGATANTACTA (SEQ ID NO: 42) | 0.3 |
| | | ANKLE1 | ankyrin repeat and LEM domain containing 1 | ENSCAFT00000024464 | chr20_48444251-48444251_G_A | 74Q > X | Substitution | Nonsense | CTCCTNGTCTC (SEQ ID NO: 43) | 0.27 |
| | | ARMC9 | armadillo repeat containing 9 | ENSCAFT00000017508 | chr25_46161506-46161506_C_T | 296T > I | Substitution | Nonsynonymous coding | TTCAANCATGT (SEQ ID NO: 44) | 0.29 |
| | | ASPM | Abnormal spindle-like microcephaly-associated protein homolog | ENSCAFT00000018114 | chr7_8578487-8578487_C_T | 1156L > F | Substitution | Nonsynonymous coding | CATTTNTTTGC (SEQ ID NO: 45) | 0.2 |
| | | ATP13A1 | ATPase type 13A1 | ENSCAFT00000022481 | chr20_46627633-46627633_C_T | 6335 > F | Substitution | Nonsynonymous coding | AATGTNCGTGC (SEQ ID NO: 46) | 0.2 |
| | | ATP2B3 | ATPase, Ca++ transporting, plasma membrane 3 | ENSCAFT00000030531 | chrX_124404772-124404772_C_T | 22P > L | Substitution | Nonsynonymous coding | GGCCCNCCATG (SEQ ID NO: 47) | 0.19 |
| | | B6EY10 | tryptophan 5-hydroxylase 1 | ENSCAFT00000014485 | chr21_43753174-43753174_C_T | 98R > Q | Substitution | Nonsynonymous coding | ATTTTNGGGAC (SEQ ID NO: 48) | 0.47 |
| | | BCAR1 | breast cancer anti-estrogen resistance 1 | ENSCAFT00000031962 | chr5_78491554-78491554_C_T | 150P > S | Substitution | Nonsynonymous coding | AGATGNCCCAT (SEQ ID NO: 49) | 0.28 |
| | | BOD1L1 | biorientation of chromosomes in cell division 1-like 1 | ENSCAFT00000024431 | chr3_69317598-69317598_C_T | 2128P > S | Substitution | Nonsynonymous coding | AACTCNCTGCG (SEQ ID NO: 50) | 0.29 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | BRDT | bromodomain, testis-specific | ENSCAFT00000032118 | chr6_59977191-59977191_C_T | 874E > K | Substitution | Nonsynonymous coding | ATTTNTTGAA (SEQ ID NO: 51) | 0.5 |
| | | BRE | brain and reproductive organ-expressed (TNFRSF1A modulator) | ENSCAFT00000008397 | chr17_25386278-25386278_G_T | 372Q > H | Substitution | Nonsynonymous coding | AACCANCCTTC (SEQ ID NO: 52) | 0.36 |
| | | C11orf80 | chromosome 11 open reading frame 80 | ENSCAFT00000019460 | chr18_53566794-53566794_G_A | 206P > L | Substitution | Nonsynonymous coding | TCAGANGCAGA (SEQ ID NO: 53) | 0.45 |
| | | C1orf168 | chromosome 1 open reading frame 168 | ENSCAFT00000030112 | chr5_55715053-55715053_C_T | 219T > I | Substitution | Nonsynonymous coding | AGAAANCCCTC (SEQ ID NO: 54) | 0.26 |
| | | C6orf211 | chromosome 6 open reading frame 211 | ENSCAFT00000000674 | chr1_44848305-44848305_C_T | 38R > X | Substitution | Nonsense | TGCATNGACAT (SEQ ID NO: 55) | 0.32 |
| | | CABP2 | calcium binding protein 2 | ENSCAFT00000018054 | chr18_52987478-52987478_G_A | 67G > E | Substitution | Nonsynonymous coding | AGTGGNGCCGG (SEQ ID NO: 56) | 0.35 |
| | | CEP250 | centrosomal protein 250kDa | ENSCAFT00000012850 | chr24_27405113-27405113_C_T | 550L > F | Substitution | Nonsynonymous coding | TCATTNTTCGG (SEQ ID NO: 57) | 0.6 |
| | | CSMD1 | CUB and Sushi multiple domains 1 | ENSCAFT00000013885 | chr16_58244318-58244318_G_A | 15515 > F | Substitution | Nonsynonymous coding | TCTGGNAATGG (SEQ ID NO: 58) | 0.48 |
| | | CSMD2 | CUB and Sushi multiple domains 2 | ENSCAFT00000005882 | chr15_11028241-11028241_C_T | 7285 > L | Substitution | Nonsynonymous coding | GACTTNGCCCA (SEQ ID NO: 59) | 0.18 |
| | | DCDC2 | doublecortin domain containing 2 | ENSCAFT00000016283 | chr35_25388917-25388917_C_T | 192G > E | Substitution | Nonsynonymous coding | GTTTTNCTTCT (SEQ ID NO: 60) | 0.54 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | DNMT3B | DNA (cytosine-5-)-methyltransferase 3 beta | ENSCAFT00000011678 | chr24_25068698-25068698_C_T | 615 > F | Substitution | Nonsynonymous coding | ATTGTNCAAGA (SEQ ID NO: 61) | 0.26 |
| | | EMR2 | EGF-like module-containing mucin-like hormone receptor-like 2 precursor | ENSCAFT00000025982 | chr20_50969425-50969425_C_T | 755 > N | Substitution | Nonsynonymous coding | GGCTGNTGAAG (SEQ ID NO: 62) | 0.43 |
| | | EXOC3L1 | exocyst complex component 3-like 1 | ENSCAFT00000032455 | chr5_85189666-85189666_G_A | 539R > K | Substitution | Nonsynonymous coding | GGTGANAGTCC (SEQ ID NO: 63) | 0.46 |
| | | FCRLA | Fc receptor-like | ENSCAFT00000020702 | chr38_23962108-23962108_C_A | 21A > S | Substitution | Nonsynonymous coding | GGCTGNCCAGA (SEQ ID NO: 64) | 0.14 |
| | | FLRT1 | fibronectin leucine rich transmembrane protein 1 | ENSCAFT00000023385 | chr18_55953743-55953743_C_T | 616G > D | Substitution | Nonsynonymous coding | CGGGGNCCCGG (SEQ ID NO: 65) | 0.31 |
| | | FMR1 | fragile X mental retardation 1 | ENSCAFT00000030311 | chrX_119344462-119344462_G_A | 331E > K | Substitution | Nonsynonymous coding | CCAAGNAAATT (SEQ ID NO: 66) | 0.24 |
| | | FMR1 | fragile X mental retardation 1 | ENSCAFT00000030311 | chrX_119344481-119344481_C_T | 3375 > F | Substitution | Nonsynonymous coding | AAATTNCCTAC (SEQ ID NO: 67) | 0.2 |
| | | FSCN3 | fascin homolog 3, actin-bundling protein, testicular (Strongylocentrotus purpuratus) | ENSCAFT00000002697 | chr14_11685668-11685668_G_A | 310R > C | Substitution | Nonsynonymous coding | TGCACNAAGCT (SEQ ID NO: 68) | 0.48 |
| | | FUT9 | Alpha-(1,3)-fucosyltransferase | ENSCAFT00000005507 | chr12_57775088-57775088_G_A | 331E > K | Substitution | Nonsynonymous coding | TTTGGNAATCA (SEQ ID NO: 69) | 0.28 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | FXYD3 | FXYD domain containing ion transport regulator 3 | ENSCAFT00000011413 | chr1_120363321-12063321_C_T | NA | Substitution | Splice site donor | TCTCANCATAG (SEQ ID NO: 70) | 0.88 |
| | | GPR126 | G protein-coupled receptor 126 | ENSCAFT00000000457 | chr1_37098753-37098753_C_T | 4155 > F | Substitution | Nonsynonymous coding | AATTTNCATAG (SEQ ID NO: 71) | 0.24 |
| | | GPR128 | G protein-coupled receptor 128 | ENSCAFT00000014844 | chr33_10191962-1019-1962_C_T | 34R > W | Substitution | Nonsynonymous coding | AAGGANGGAGG (SEQ ID NO: 72) | 0.33 |
| | | GPR82 | G protein-coupled receptor 82 | ENSCAFT00000022877 | chrX_36056596-36056596_C_T | 213S > L | Substitution | Nonsynonymous coding | ATTTTNATTTT (SEQ ID NO: 73) | 0.32 |
| | | GRM6 | glutamate receptor, metabotropic 6 | ENSCAFT00000000509 | chr11_5596380-5596-380_C_T | 523P > L | Substitution | Nonsynonymous coding | CCTCCNCTGTG (SEQ ID NO: 74) | 0.53 |
| | | GSX1 | GS homeobox 1 | ENSCAFT00000010870 | chr25_14841844-14841844_C_T | NA | Substitution | Splice site acceptor | GCTGTNTGGAG (SEQ ID NO: 75) | 0.36 |
| | | GTF2I | general transcription factor IIi | ENSCAFT00000038018 | chr6_8807549-8807549_G_A | 145Q > X | Substitution | Nonsense | AGACTNATCTC (SEQ ID NO: 76) | 0.43 |
| | | HDAC8 | histone deacetylase 8 | ENSCAFT00000027174 | chrX_59408793-59408793_G_A | 3595 > F | Substitution coding | Nonsynonymous | GGGAANAGAAG (SEQ ID NO: 77) | 0.71 |
| | | HECTD4 | HECT domain containing E3 ubiquitin protein ligase 4 | ENSCAFT00000014076 | chr26_12845851-12845851_C_T | 541R > Q | Substitution | Nonsynonymous coding | CTTCCNGCTTG (SEQ ID NO: 78) | 0.38 |
| | | K1C10 | keratin, type I cytoskeletal 10 | ENSCAFT00000025391 | chr9_25194405-25194405_G_A | 316E > K | Substitution | Nonsynonymous coding | AATACNAACAA (SEQ ID NO: 79) | 0.3 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | KCNG3 | potassium voltage-gated channel, subfamily G, member 3 | ENSCAFT00000035514 | chr17_37144629-37144629_G_A | 3665 > F | Substitution | Nonsynonymous coding | TGTTGNATGTT (SEQ ID NO: 80) | 0.43 |
| | | KIF25 | kinesin family member 25 | ENSCAFT00000001345 | chr1_58634208-58634208_G_A | 509E > K | Substitution | Nonsynonymous coding | TGTCGNAGCGC (SEQ ID NO: 81) | 0.33 |
| | | LAMB2 | laminin, beta 2 (laminin S) | ENSCAFT00000018765 | chr20_43058275-43058275_C_T | 1054P > L | Substitution | Nonsynonymous coding | GTGCCNGTCCA (SEQ ID NO: 82) | 0.38 |
| | | LIMK1 | LIM domain kinase 1 | ENSCAFT00000019799 | chr6_9274167-9274167_G_A | 222R > W | Substitution | Nonsynonymous coding | GATCCNGTCTC (SEQ ID NO: 83) | 0.6 |
| | | LY9 | lymphocyte antigen 9 | ENSCAFT00000020056 | chr38_24536297-24536297_C_T | 263E > K | Substitution | Nonsynonymous coding | CGACTNCCCCA (SEQ ID NO: 84) | 0.58 |
| | | MBD5 | methyl-CpG binding domain protein 5 | ENSCAFT00000008917 | chr19_53239621-53239621_C_T | 1189P > L | Substitution | Nonsynonymous coding | TGGTCNAGCTA (SEQ ID NO: 85) | 0.32 |
| | | MLF1 | myeloid leukemia factor 1 | ENSCAFT00000014162 | chr23_54989572-54989572_C_T | 164A > V | Substitution | Nonsynonymous coding | CCGAGNTCATG (SEQ ID NO: 86) | 0.33 |
| | | NELL1 | NEL-like 1 (chicken) | ENSCAFT00000015919 | chr21_46027895-46027895_G_A | 105E > K | Substitution | Nonsynonymous coding | CTGTCNAATGT (SEQ ID NO: 87) | 0.24 |
| | | NF1 | neurofibromin 1 | ENSCAFT00000029545 | chr9_44834512-44834512_G_A | 1933P > S | Substitution | Nonsynonymous coding | CCACGNAGTCA (SEQ ID NO: 88) | 0.48 |
| | | Novel gene | Uncharacterized protein | ENSCAFT00000021819 | chr27_39478508-39478508_G_A | 1291E > K | Substitution | Nonsynonymous coding | GTTCTNAACTA (SEQ ID NO: 89) | 0.36 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | Novel gene | Uncharacterized protein | ENSCAFT00000004310 | chr1_106460436-106460436_G_A | 314E > K | Substitution | Nonsynonymous coding | GGGAGNAGAAA (SEQ ID NO: 90) | 0.47 |
| | | Novel gene | Uncharacterized protein | ENSCAFT00000028222 | chr6_27157711-27157711_C_T | 319M > I | Substitution | Nonsynonymous coding | AAAATNATGCA (SEQ ID NO: 91) | 0.39 |
| | | Novel gene | Uncharacterized protein | ENSCAFT00000027418 | chr8_56643270-56643270_G_A | 395R > C | Substitution | Nonsynonymous coding | TAAACNATCAG (SEQ ID NO: 92) | 0.38 |
| | | Novel gene | Uncharacterized protein | ENSCAFT00000012946 | chr25_30547894-30547894_G_A | 397D > N | Substitution | Nonsynonymous coding | GGCATNATGGC (SEQ ID NO: 93) | 0.31 |
| | | Novel gene | Uncharacterized protein | ENSCAFT00000030235 | chrX_115997637-115997637_C_T | 6E > K | Substitution | Nonsynonymous coding | CAATTNGCCAG (SEQ ID NO: 94) | 0.41 |
| | | Novel gene | Uncharacterized protein | ENSCAFT00000024549 | chr6_14378075-14378075_G_A | 734S > F | Substitution | Nonsynonymous coding | TTTTGNAAATT (SEQ ID NO: 95) | 0.36 |
| | | Novel gene | Uncharacterized protein | ENSCAFT00000009040 | chr1_116977163-11g77163_C_A | 56E > X | Substitution | Nonsense | CACTTNGGAGC (SEQ ID NO: 96) | 0.17 |
| | | NTN5 | netrin 5 | ENSCAFT00000006331 | chr1_110537423-110B37423_G_A | 259W > X | Substitution | Nonsense | CTTCTNGAGGG (SEQ ID NO: 97) | 0.17 |
| | | NUP210L | nucleoporin 210kDa-like | ENSCAFT00000027524 | chr7_46057921-460E7921_C_T | 287P > S | Substitution | Nonsynonymous coding | GATTTNCTCTG (SEQ ID NO: 98) | 0.25 |
| | | NVL | nuclear VCP-like | ENSCAFT00000025949 | chr7_43088033-430E8033_C_T | 7835 > L | Substitution | Nonsynonymous coding | CTACTNGTGAG (SEQ ID NO: 99) | 0.16 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | OLFM4 | olfactomedin 4 | ENSCAFT00000038323 | chr22_13020301-13020301_G_C | 245Q > H | Substitution | Nonsynonymous coding | GTTCANCTCAA (SEQ ID NO: 100) | 0.26 |
| | | OR11H4 | olfactory receptor, family 11, subfamily H, member 4 | ENSCAFT00000008634 | chr15_20603710-2060-3710_G_A | 352M > I | Substitution | Nonsynonymous coding | GACATNAAATT (SEQ ID NO: 101) | 0.33 |
| | | OR11L1 | olfactory receptor, family 11, subfamily L, member 1 | ENSCAFT00000039246 | chr14_4576143-4576143_C_T | 164S > F | Substitution | Nonsynonymous coding | GATTTNCAAGT (SEQ ID NO: 102) | 0.25 |
| | | PEPB | pepsin B precursor | ENSCAFT00000031388 | chr6_43778633-43778633_G_A | 367D > N | Substitution | Nonsynonymous coding | TGGGANATGTC (SEQ ID NO: 103) | 0.14 |
| | | PHKA2 | phosphorylase kinase, alpha 2 (liver) | ENSCAFT00000020564 | chrX_14879295-14879295_C_T | NA | Substitution | Splice site donor | ACTTANTTTAT (SEQ ID NO: 104) | 0.46 |
| | | PKHD1 | polycystic kidney and hepatic disease 1 (autosomal recessive) | ENSCAFT00000003416 | chr12_22675987-22675987_G_A | 1323S > L | Substitution | Nonsynonymous coding | TCACTNAGTTG (SEQ ID NO: 105) | 0.38 |
| | | PRDM2 | PR domain containing 2, with ZNF domain | ENSCAFT00000025940 | chr2_86311966-86311966_G_A | 1366P > S | Substitution | Nonsynonymous coding | GGACGNCAGCG (SEQ ID NO: 106) | 0.31 |
| | | PTPRO | protein tyrosine phosphatase, receptor type, O | ENSCAFT00000020369 | chr27_34189070-34189070_C_T | 309E > K | Substitution | Nonsynonymous coding | TTTTTNCGTCT (SEQ ID NO: 107) | 0.57 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | PTPRZ1 | protein tyrosine phosphatase, receptor-type, Z polypeptide 1 | ENSCAFT00000005646 | chr14_62891929-62891929_T_C | 1733L > P | Substitution | Nonsynonymous coding | TAAACNT GCAC (SEQ ID NO: 108) | 0.11 |
| | | Q28302 | Uncharacterized protein | ENSCAFT00000035111 | chr20_54398781-54398781_C_T | 202L > F | Substitution | Nonsynonymous coding | AACTCNT CAAC (SEQ ID NO: 109) | 0.34 |
| | | Q38IV3 | Multidrug resistance protein 3 | ENSCAFT00000027259 | chr9_29903253-29903253_G_A | 761R > Q | Substitution | Nonsynonymous coding | CCAGCNA CAGC (SEQ ID NO: 110) | 0.47 |
| | | Q8HYR2 | Uncharacterized protein | ENSCAFT00000019633 | chr27_29388021-29388021_A_T | 166I > F | Substitution | Nonsynonymous coding | GAAATNT TATA (SEQ ID NO: 111) | 0.59 |
| | | RCC2 | regulator of chromosome condensation 2 | ENSCAFT00000024961 | chr2_83776440-83776440_C_T | 309P > L | Substitution | Nonsynonymous coding | GGTCCNC CGGC (SEQ ID NO: 112) | 0.46 |
| | | RP1 | oxygen-regulated protein 1 | ENSCAFT00000011204 | chr29_9140829-9140829_G_A | 1861E > K | Substitution | Nonsynonymous coding | AATCANA AAGA (SEQ ID NO: 113) | 0.3 |
| | | RTKN2 | rhotekin 2 | ENSCAFT00000020670 | chr4_173382177-173382177_G_A | 6025 > L | Substitution | Nonsynonymous coding | GCCATNA TCTG (SEQ ID NO: 114) | 0.29 |
| | | SAMD7 | sterile alpha motif domain containing 7 | ENSCAFT00000023423 | chr34_37539386-37539386_G_A | 369R > Q | Substitution | Nonsynonymous coding | TCTTCNA AGCA (SEQ ID NO: 115) | 0.29 |
| | | SLAF1 | Signaling lymphocytic activation molecule | ENSCAFT00000019982 | chr38_24663637-24663637_C_T | 2335 > L | Substitution | Nonsynonymous coding | GTCTTNG GGTG (SEQ ID NO: 116) | 0.53 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | SLC47A2 | solute carrier family 47, member 2 | ENSCAFT00000036298 | chr5_43495248-43495248_C_T | 83S > F | Substitution | Nonsynonymous coding | AGTTTNCATAG (SEQ ID NO: 117) | 0.38 |
| | | SULT4A1 | sulfotransferase family 4A, member 1 | ENSCAFT00000035674 | chr10_24862764-24862764_G_A | 72M > I | Substitution | Nonsynonymous coding | TTGATNAACAT (SEQ ID NO: 118) | 0.26 |
| | | TAF7L | TAF7-like RNA polymerase II, TATA box binding protein (TBP)-associated factor, 50kDa | ENSCAFT00000027954 | chrX_78291782-78291782_C_T | 366E > K | Substitution | Nonsynonymous coding | CTTTTNAIAAT (SEQ ID NO: 119) | 0.41 |
| | | TBC1D15 | TBC1 domain family, member 15 | ENSCAFT00000000735 | chr10_16382190-16382190_C_T | 176S > F | Substitution | Nonsynonymous coding | TGACTNTCTTG (SEQ ID NO: 120) | 0.3 |
| | | TLR1 | toll-like receptor 1 precursor | ENSCAFT00000037196 | chr3_76368607-76368607_G_A | 234W > X | Substitution | Nonsense | GGATGNTCTTA (SEQ ID NO: 121) | 0.3 |
| | | TMEM74 | transmembrane protein 74 | ENSCAFT00000001114 | chr13_12451185-12451185_G_A | 61R > C | Substitution | Nonsynonymous coding | AGGGCNAAGTT (SEQ ID NO: 122) | 0.34 |
| | | TOM1 | target of myb1 (chicken) | ENSCAFT00000002700 | chr10_31874137-31874137_A_C | 50V > G | Substitution | Nonsynonymous coding | GCATCNCCTCA (SEQ ID NO: 123) | 0.36 |
| | | TRIM58 | tripartite motif containing 58 | ENSCAFT00000001915 | chr14_4533386-4533386_G_C | 455T > R | Substitution | Nonsynonymous coding | CGTTTNTTACA (SEQ ID NO: 124) | 0.23 |
| | | TRIM66 | tripartite motif containing 66 | ENSCAFT00000011106 | chr21_35253035-35253035_G_A | 662L > F | Substitution | Nonsynonymous coding | TGGGANAGGCG (SEQ ID NO: 125) | 0.43 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | TTN | titin | ENSCAFT00000022319 | chr36_25212813-25212813_C_T | 25277E > K | Substitution | Nonsynonymous coding | ACTTTNTT TAA (SEQ ID NO: 126) | 0.31 |
| | | TTN | titin | ENSCAFT00000022319 | chr36_25208898-25208898_G_A | 26582P > S | Substitution | Nonsynonymous coding | GACCGNT TCGC (SEQ ID NO: 127) | 0.36 |
| | | TTN | titin | ENSCAFT00000022319 | chr36_25207752-25207752_C_T | 26964E > K | Substitution | Nonsynonymous coding | GTTTTNT GCAT (SEQ ID NO: 128) | 0.32 |
| | | TTN | titin | ENSCAFT00000022319 | chr36_25363681-25363681_C_T | 6209E > K | Substitution | Nonsynonymous coding | GTTCTNG TGAC (SEQ ID NO: 129) | 0.32 |
| | | U5P45 | ubiquitin specific peptidase 45 | ENSCAFT00000005638 | chr12_60682412-60682412_G_A | 232P > S | Substitution | Nonsynonymous coding | GGGAGNA AAAA (SEQ ID NO: 130) | 0.43 |
| 04-R04 | OSA_c | ASTN1 | astrotactin 1 | ENSCAFT00000022524 | chr7_25651338-25651338_C_T | 762A > V | Substitution | Nonsynonymous coding | TGTGGNC TTGT (SEQ ID NO: 131) | 0.26 |
| | | ASXL3 | additional sex combs like 3 (Drosophila) | ENSCAFT00000028551 | chr7_59080331-59080331_G_A | 1100P > L | Substitution | Nonsynonymous coding | CGGCCN GAGGC (SEQ ID NO: 132) | 0.33 |
| | | FRMPD4 | FERM and PDZ domain containing 4 | ENSCAFT00000018460 | chrX_9178376-9178376_G_A | 1180A > T | Substitution | Nonsynonymous coding | TGGACNC GGGC (SEQ ID NO: 133) | 0.17 |
| | | MC4R | melanocortin receptor 4 | ENSCAFT00000000145 | chr1_19140979-19140979_G_A | 47V > I | Substitution | Nonsynonymous coding | TCTTCNT CTCC (SEQ ID NO: 134) | 0.33 |
| | | MGAM | maltase-glucoamylase (alpha-glucosidase) | ENSCAFT00000006194 | chr16_10143723-10143723_T_ | NA | Deletion | Frameshift | GGGTGNT TTTT (SEQ ID NO: 135) | 0.24 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | NFATC1 | nuclear factor of activated T-cells, cytoplasmic, calcineurin-dependent 1 | ENSCAFT00000000013 | chr1_4124943-4124943_A_G | 8V > A | Substitution | Nonsynonymous coding | AAAGGNCTGGA (SEQ ID NO: 136) | 0.4 |
| | | NFE2L3 | nuclear factor (erythroid-derived 2)-like 3 | ENSCAFT00000038557 | chr14_42452261-42452264_GATG | NA | Deletion | Frameshift | AAGATNATGTA (SEQ ID NO: 137) | 0.3 |
| | | TP53 | cellular tumor antigen p53 | ENSCAFT00000026465 | chr5_35558664-35558664_A_G | 260F > S | Substitution | Nonsynonymous coding | CCTCANAGCTG (SEQ ID NO: 138) | 0.54 |
| | | PLEKHB1 | pleckstrin homology domain containing, family B (evectins) member 1 | ENSCAFT00000009009 | chr21_27601782-27601782_C_T | 142R > H | Substitution | Nonsynonymous coding | CTCGGNGGCTC (SEQ ID NO: 139) | 0.43 |
| | | PTPN14 | protein tyrosine phosphatase, non-receptor type 14 | ENSCAFT00000019934 | chr7_15317710-15317710_C_T | 911G > R | Substitution | Nonsynonymous coding | CATTCNCTCTT (SEQ ID NO: 140) | 0.12 |
| | | RBBP6 | retinoblastoma binding protein 6 | ENSCAFT00000027846 | chr6_24499626-24499626_T_C | 1730K > R | Substitution | Nonsynonymous coding | TCTTTNTGCTG (SEQ ID NO: 141) | 0.3 |
| | | TDRD6 | tudor domain containing 6 | ENSCAFT00000003223 | chr12_17857549-17857549_G_A | 1517W > X | Substitution | Nonsense | AACTGNTATAA (SEQ ID NO: 142) | 0.49 |
| | | TEX15 | testis expressed 15 | ENSCAFT00000010405 | chr16_36456696-36456696_G_T | 1265V > F | Substitution | Nonsynonymous coding | TTTCANTTTTG (SEQ ID NO: 143) | 0.58 |
| | | TRAP1 | TNF receptor-associated protein 1 | ENSCAFT00000030584 | chr6_40616562-40616562_C_A | 42A > D | Substitution | Nonsynonymous coding | TCCAGNCCAGT (SEQ ID NO: 144) | 0.3 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| 04-R02 | STS-PNST | KIAA1217 | uncharacterized protein | ENSCAFT00000006799 | chr2_11859851-11859851_G_A | 356A > V | Substitution | Nonsynonymous coding | GAGAGNC GGGG (SEQ ID NO: 145) | 0.45 |
| | | MFSD2B | major facilitator superfamily domain containing 2B | ENSCAFT00000006341 | chr17_21486565-21486565_C_T | 494R > C | Substitution | Nonsynonymous coding | GTGCANG TGGG (SEQ ID NO: 146) | 0.42 |
| | | Novel gene | uncharacterized protein | ENSCAFT00000030447 | chrX_123930541-123930541_G_C | 327R > P | Substitution | Nonsynonymous coding | AGGGCNC CCCG (SEQ ID NO: 147) | 0.14 |
| | | SLC16A2 | solute carrier family 16, member 2 (thyroid hormone transporter) | ENSCAFT00000027229 | chrX_60903455-60903455_G_A | 72A > T | Substitution | Nonsynonymous coding | CCTTCNC CTTT (SEQ ID NO: 148) | 0.4 |
| | | TEP1 | telomerase-associated protein 1 | ENSCAFT00000008693 | chr15_20729329-20729329_G_A | 1900L > F | Substitution | Nonsynonymous coding | CAGGANG CCCC (SEQ ID NO: 149) | 0.42 |
| | | XPNPEP2 | X-prolyl aminopeptidase (aminopeptidase P) 2, membrane-bound | ENSCAFT00000029688 | chrX_104033303-104033303_C_T | 502R > X | Substitution | Nonsense | CAGGGN GAATG (SEQ ID NO: 150) | 0.25 |
| 01-R02 | STS-PNST | ACD | adrenocortical dysplasia homolog (mouse) | ENSCAFT00000032411 | chr5_84799806-84799806_C_A | 388P > H | Substitution | Nonsynonymous coding | TGGCCNC CTGC (SEQ ID NO: 151) | 0.13 |
| | | ADAMTS5 | ADAM metallopeptidase with thrombospondin type 1 motif, 5 | ENSCAFT00000013627 | chr31_25306205-25306205_G_A | 226H > Y | Substitution | Nonsynonymous coding | CTGATNC TGCC (SEQ ID NO: 152) | 0.13 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | ADRB2 | beta-2 adrenergic receptor | ENSCAFT00000029135 | chr4_63253706-63253706_C_T | 76C > Y | Substitution | Nonsynonymous coding | CAGCANA GGCC (SEQ ID NO: 153) | 0.12 |
| | | ATP7B | copper-transporting ATPase 2 | ENSCAFT00000068859 | chr22_3160667-3160667_G_A | 1119V > M | Substitution | Nonsynonymous coding | TGGGCNT GGCC (SEQ ID NO: 154) | 0.2 |
| | | CDK14 | cyclin-dependent kinase 14 | ENSCAFT00000003009 | chr14_19522937-19522937_C_T | 102R > W | Substitution | Nonsynonymous coding | TCAGGNG GCAC (SEQ ID NO: 155) | 0.2 |
| | | IER5L | immediate early response 5-like | ENSCAFT00000031805 | chr9_57855189-57855189_G_A | 205 > N | Substitution | Nonsynonymous coding | CCACANC TCCC (SEQ ID NO: 156) | 0.16 |
| | | IRS1 | insulin receptor substrate 1 | ENSCAFT00000016522 | chr25_42687032-42687032_C_T | 139S > N | Substitution | Nonsynonymous coding | CCGAGNT GCCG (SEQ ID NO: 157) | 0.11 |
| | | JAG1 | jagged 1 | ENSCAFT00000009074 | chr24_14655994-14655994_G_A | 935 > N | Substitution | Nonsynonymous coding | CTGTANC TTCG (SEQ ID NO: 158) | 0.11 |
| | | JUNB | jun B proto-oncogene | ENSCAFT00000027182 | chr20_52362490-52362490_G_A | 775 > L | Substitution | Nonsynonymous coding | GCTCCNA TGAG (SEQ ID NO: 159) | 0.14 |
| | | LMNA | lamin A/C | ENSCAFT00000026695 | chr7_44690367-44690367_G_A | 64T > I | Substitution | Nonsynonymous coding | ACTCGNT GATG (SEQ ID NO: 160) | 0.15 |
| | | MADCAM1 | mucosal addressin cell adhesion molecule 1 precursor | ENSCAFT00000031356 | chr20_61126306-61126306_G_ | NA | Deletion | Frameshift | AAAGTNG GGGG (SEQ ID NO: 161) | 0.27 |
| | | MEFV | Mediterranean fever | ENSCAFT00000037775 | chr6_41024970-41024970_C_A | 673N > K | Substitution | Nonsynonymous coding | GGAAANA AGAC (SEQ ID NO: 162) | 0.26 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | Novel Gene | Aldehyde dehydrogenase | ENSCAFT000 00017771 | chr18_52833141-52833141_A_G | 250V > A | Substitution | Nonsynonymous coding | ACAGGNC GTAG (SEQ ID NO: 163) | 0.11 |
| | | NRM | nurim (nuclear envelope membrane protein) | ENSCAFT000 00000694 | chr12_3488483-3488483_C_T | 524S > N | Substitution | Nonsynonymous coding | GGCAGNT GCGG (SEQ ID NO: 164) | 0.11 |
| | | PIM1 | proto-oncogene serine/threonine-protein kinase pim-1 | ENSCAFT000 00002258 | chr12_9213964-9213964_G_A | 73G > D | Substitution | Nonsynonymous coding | CCCCGNC TCCT (SEQ ID NO: 165) | 0.22 |
| | | PIM1 | proto-oncogene serine/threonine-protein kinase pim-1 | ENSCAFT000 00002258 | chr12_9214807-9214807_C_T | 250H > Y | Substitution | Nonsynonymous coding | ACTGCNA CAAC (SEQ ID NO: 166) | 0.22 |
| | | PIM1 | proto-oncogene serine/threonine-protein kinase pim-1 | ENSCAFT000 00002258 | chr12_9214750-9214750_C_T | 231Q > X | Substitution | Nonsense | CCCTGNA GGAG (SEQ ID NO: 167) | 0.2 |

TABLE 3-continued

Somatic Alterations in Canine Sarcomas

| Case ID | Tumor Type | Gene Symbol | Gene Description | Transcript Accession | Nucleotide (genomic) Position of Mutation | Amino Acid (protein) Position of Mutation | Mutation Type | Consequence | Sequence Context (Position of Mutation Indicated by "N") | % Mutant Reads |
|---|---|---|---|---|---|---|---|---|---|---|
| | | PTCH1 | Patched-like protein 1 | ENSCAFT00000001978 | chr1_74305255-74305255_G_A | 73A > T | Substitution | Nonsynonymous coding | GGAAANCTACT (SEQ ID NO: 168) | 0.16 |
| | | TRPS1 | trichorhinophalangeal syndrome I | ENSCAFT00000001274 | chr13_18226051-18226051_C_T | 5305 > N | Substitution | Nonsynonymous coding | CATGANTGTCC (SEQ ID NO: 169) | 0.13 |
| | | ZFP36L1 | zinc finger protein 36, C3H type-like 1 | ENSCAFT00000026141 | chr8_45703888-45703888_C_T | 145 > N | Substitution | Nonsynonymous coding | CTTCGNTCAAG (SEQ ID NO: 170) | 0.13 |

STS - soft tissue sarcoma;
STS-PNST - soft tissue sarcoma, peripheral nerve sheath tumor;
OSA, - chondroblastic osteosarcoma.

TABLE 4a

Types of somatic changes observed across canine soft tissue sarcomas

| Type | Subtype | Number of alterations | Percentage of alterations (%) |
|---|---|---|---|
| Substitutions | Nonsense | 11 | 6 |
|  | Missense (non-synonymous) | 135 | 73 |
|  | Splice site acceptor | 1 | 1 |
|  | Splice site donor | 4 | 2 |
|  | Subtotal | 151 | 82 |
| INDELs | Deletion | 4 | 2 |
|  | Insertion | 1 | 1 |
|  | Subtotal | 5 | 3 |
| CNAs | Deletion | 0 | 0 |
|  | Amplification | 28 | 15 |
|  | Subtotal | 28 | 15 |
|  | Total | 184 | 100 |

INDELs - insertions and deletions;
CNAs - copy number alterations

TABLE 4b

Type of somatic mutations across canine soft tissue sarcomas

| Type of somatic alteration | Number | Percentage |
|---|---|---|
| 1 bp deletion | 3 | 1.9 |
| 3 bp deletion | 1 | 0.6 |
| 1 bp deletion | 1 | 0.6 |
| A:T > C:G | 3 | 1.9 |
| A:T > G:C | 4 | 2.6 |
| A:T > T:A | 3 | 1.9 |
| C:G > A:T | 4 | 2.6 |
| C:G > G:C | 2 | 1.3 |
| C:G > T:A | 71 | 45.5 |
| G:C > A:T | 53 | 34.0 |
| G:C > C:G | 3 | 1.9 |
| G:C > T:A | 4 | 2.6 |
| T:A > A:T | 1 | 0.6 |
| T:A > C:G | 1 | 0.6 |
| T:A > G:C | 2 | 1.3 |
| Total | 156 | 100 |

TABLE 5

Genes mutated in both human and canine cancers

| Gene | Number of somatic alterations | Type of alteration | Number of samples | Human driver gene or mutated in human soft tissue sarcoma |
|---|---|---|---|---|
| ANKRD11 | 1 | SBS (splice site) | 1 | Joseph et al., 2013 |
| ATP7B | 2 | SBS (missense) | 2 | Joseph et al., 2013 |
| BRDT | 1 | SBS (missense) | 1 | Chemielecki et al., 2013 |
| BRWD3 | 1 | SBS (missense) | 1 | Joseph et al., 2013 |
| CSMD2 | 1 | SBS (missense) | 1 | Joseph et al., 2013 |
| FCRLB | 1 | SBS (missense) | 1 | Lee et al., 2012 |
| IRS1 | 1 | SBS (missense) | 1 | Barretina et al., 2010 |
| LIMK1 | 1 | SBS (missense) | 1 | Lee et al., 2012 |
| MBD5 | 1 | SBS (missense) | 1 | Lee et al., 2012 |
| MLL3 | 1 | Deletion | 1 | Vogelstein et al., 2013 |
| NF1 | 1 | SBS (missense) | 1 | Barretina et al., 2010 |
| PKHD1 | 1 | SBS (missense) | 1 | Lee et al., 2012 |
| PTCH1 | 1 | SBS (missense) | 1 | Vogelstein et al., 2013 |
| PTPRZ1 | 1 | SBS (missense) | 1 | Chemielecki et al., 2013 |
| RP1 | 1 | SBS (missense) | 1 | Chemielecki et al., 2013 |
| TTN | 4 | SBS (missense) | 1 | Chemielecki et al., 2013 |
| MDM4 | 1 | Amplification | 1 | Vogelstein et al., 2013 |
| CNTN2 | 1 | Amplification | 1 | Chemielecki et al., 2013 |

Amplifications and deletions were less common, with an average of three per tumor (range: of 0-17) (FIG. 5). Seven of the 10 soft tissue sarcomas harbored no amplifications or deletions. The chondroblastic osteosarcoma exome was similar to those of the soft tissue sarcomas, with 14 somatic mutations and four amplifications (Table 3 and FIG. 6).

Single base substitutions were identified in four tumor suppressor genes that are frequently mutated in human tumors (NF1, MLL3, TP53, and PTCH1). Additionally, MDM4, an oncogene that has been shown to be amplified but not point-mutated in human cancers was found to be amplified (but not point-mutated) in one canine tumor (Lee, et al., 2012, Barretina, et al., 2010, Chmielecki, et al., 2013, Vogelstein, et al., 2013). The only genes mutated in more than one tumor were ATP7B (missense mutations in two tumors) and A/G1 (amplified in two tumors). Interestingly, mutations in ATP7B were also found in a human liposarcomas (Joseph, et al., 2013). Twenty-two of the 184 somatic mutations in canine tumors occurred in genes previously shown to be mutated in human soft tissue sarcomas (Table 5).

Larger studies of soft tissue sarcomas in both species will be required to determine whether these represent driver mutations that signify important, conserved tumorigenic pathways. Regardless, the genetic landscapes of canine tumors were similar to those of humans in terms of the numbers of genetic alterations and spectrum of mutations. Specifically, they exclude the possibility that the canine tumors have a very large number of mutations which might make them more likely to mount an immune response than analogous tumor types in humans.

Example 6

Intratumoral (IT) Administration of *C. novyi* NT—Study 1 Methods

To investigate the safety and efficacy of the method of the present invention, a comparative study in 16 dogs with spontaneously occurring solid tumors was performed (Table 6).

TABLE 6

Patient Characteristics

| Case ID | Sex[a] | Breed | Age (years) | Body Weight (kg) | Tumor type[b] | Grade[c] | Location | Longest diameter[d] (mm) | Previous treatment | # of IT C. novyi-NT treatments |
|---|---|---|---|---|---|---|---|---|---|---|
| 01-R02 | FN | Border collie | 14.3 | 21.7 | STS-PNST | II | Left flank | 43 | None | 4 |
| 04-R01 | MN | Golden retriever | 7.9 | 34.0 | STS-PNST | II | Right maxilla | 15 | Surgical | 4 |
| 04-R02 | MI | Golden retriever | 12.0 | 38.8 | STS-PNST | I | Right lateral metacarpus | 46 | Surgical | 4 |
| 04-R03 | MN | Boxer | 9.6 | 29.4 | STS | I | Left medial antebrachium | 56 | None | 3[TR] |
| 04-R04 | FN | St. Bernard | 11.7 | 31.0 | OSA$_c$ | III | Right proximal humerus | ND | Surgical | 1[AE] |
| 04-R05 | MN | Shetland sheepdog | 14.0 | 13.4 | STS | III | Right cranial antebrachium | 45 | Surgical & C. novyi-NT spores IV | 4 |
| 04-R06 | FN | Labrador retriever | 11.6 | 24.3 | MCT | III | Right hindlimb digit III | 23 | None | 4 |
| 04-R08 | FN | Shepherd | 7.2 | 28.9 | STS-PNST | I | Right medial hindlimb paw | 65 | Surgical | 3[PD] |
| 10-R01 | MN | Golden retriever | 13.7 | 33.6 | OMM | III | Left mandible | 27 | Surgical | 2[AE] |
| 10-R02 | MN | Pit bull terrier | 10.0 | 43.6 | STS | I | Right flank | 53 | Surgical | 4 |
| 11-R01 | MN | Maltese | 11.1 | 8.1 | STS-PNST | II | Left pinna | 28 | Surgical | 1[TR] |
| 11-R02 | FN | Labrador retriever | 12.2 | 30.3 | STS-PNST | II | Left stifle | 43 | None | 3[IV] |
| 11-R04 | MN | Husky | 10.3 | 44.3 | STS | I | Right forelimb paw | 29 | None | 4 |
| 16-R02 | MN | Labrador retriever | 9.8 | 36.8 | STS | I | Left lateral thigh | 91 | Surgical | 4 |
| 16-R03 | FN | Shepherd | 10.8 | 20.8 | STS | I | Left forelimb paw | 53 | Surgical | 4 |
| 26-R01 | MN | Labrador retriever | 7.9 | 30.8 | STS | II | Right forelimb paw | 24 | None | 4 |

[a]FN—female neutered; MN—male neutered; MI—male intact.
[b]STS—soft tissue sarcoma; STS - PNST—peripheral nerve sheath tumor; OSA$_c$—chondroblastic osteosarcoma; MCT—mast cell tumor; OMM—oral malignant melanoma.
[c]Grading based on published criteria (Dennis et al., 2011, Patnaik et al., 1984, Smedley et al., 2011, Sabattini et al., 2014): I—low grade; II—intermediate grade; III—high grade; NA—not assessed.
[d]Longest diameter at time of first C. novyi -NT administration (day 0). ND—unmeasurable due to location.
[e]04-R05—previous C. novyi -NT therapy with a single IV injection of $1 \times 10^7$ spores/m$^2$ 437 days prior to the first IT administration of C. novyi-NT spores.
[f]Reason for number of treatments less than 4 given in superscript: TR—tumor response; AE—adverse event; PD—progressive disease; IV—4th dose given intravenously.

Dogs were enrolled at multiple sites participating in the Animal Clinical Investigation oncology network (ACI, Washington, D.C.) and written informed consent was obtained from owner(s) prior to enrollment. Treatment, management, and study evaluations were overseen by board-certified veterinary oncologists. Enrollment was offered to client-owned dogs with spontaneous solid tumors, with a preference for soft-tissue sarcomas that had failed standard therapy or whose owner(s) had declined such therapy. Participation was restricted to tumor bearing dogs with a target lesion having a longest diameter between 1 and 7 centimeters. Dogs with tumors located in areas where abscess development would be catastrophic (e.g., nasal tumors that extended into the brain or significant pulmonary metastatic disease) were excluded from the study.

Dogs with evidence of an active bacterial infection requiring systemic antibiotic therapy within seven days or cancer therapy (chemotherapy, radiation therapy, and immunotherapy) within 21 days of C. novyi-NT spore treatment were ineligible. Dogs were required to have a performance score of 0 or 1 (Table 7) and to be available for the full duration of the study for enrollment. Concurrent use of anticancer agents and participation in other clinical trials were prohibited. Dogs that were pregnant or likely to become pregnant were not included in the study. Also, dogs that may have been unavailable for the entire study duration, and dogs that were considered unsuitable for study enrollment by the Investigator or Medical Director were not included in the study.

TABLE 7

Performance status evaluations

| Score | Description |
|---|---|
| 0 | Normal activity |
| 1 | Restricted activity: decreased activity from pre-disease status |
| 2 | Compromised: ambulatory only for vital activities, able to consistently defecate and urinate in acceptable areas |
| 3 | Disabled: must be force fed and/or unable to confine urination and defecation to acceptable areas |
| 4 | Death |

During a screening visit, each dog was assigned a unique study dog identification number consisting of a 5-digit numeric code (which may not have been sequentially in order of the screening dog number). The first 2 digits indicated the study site (01 to 99), the middle digit indicated the study 'R', and the last 2 digits described the study dog number within a study site (01 to 99). For example the 11th dog enrolled at Site 9 was assigned study dog number 09-R11. Study dog numbers were assigned chronologically in the order that dogs were enrolled at a given study site. A dog was considered enrolled in the study when it satisfied the inclusion and exclusion criteria.

Gross pathology and histopathology was performed in accordance with Food and Drug Administration's CVM Guidance for Industry 185. At necropsy, the following tissues (Table 8) were assessed for gross pathology and for histopathology and described in the necropsy report. Samples of brain, heart, lung, liver, spleen, kidney, muscle, bone, small intestine, large intestine and any tissue with gross abnormality were collected for microbiology.

TABLE 8

List of tissues to be examined by gross pathology and histopathology

Pituitary gland
Thyroid gland
Parathyroid gland
Adrenal gland
Pancreas
Ovaries
Uterus
Testes
Prostate
Epididymis
Heart
Ventricles
Brain
Spinal cord
Eyes
Lung
Muscle
Mammary gland
Liver
Gall bladder
Kidneys
Urinary bladder TABLE 8-continued List of tissues to be examined by gross pathology and histopathology Lymph nodes
Skin
Bone and marrow
Marrow smear
Spleen
Stomach
Duodenum
Jejunum
Ileum
Colon
Cecum
Thymus
Injection site
Any abnormal tissues All dogs were hospitalized from day 0 (DO) to day 4 (D4), and then optionally (at the Investigator's discretion) for 24 to 48 hours after each subsequent treatment for clinical observation. Fluids were administered to all study dogs during hospitalization following *C. novyi* NT treatment. On dosing days all dogs were administered intravenous (IV) crystalloids at 4 ml/kg/h for 2 hours. Dogs were closely monitored for six hours after each IT injection of *C. novyi*-NT spores. At the next visit (4 days later) all dogs were administered subcutaneous (SQ) crystalloids at 20 ml/kg. If a dog was hospitalized and receiving IV crystalloids on the day that SQ crystalloids were to be administered, it was not necessary to give the SQ dose.

Study visits and events are summarized in Table 9 as an example of a 4-dose treatment regimen. The dosing interval was suggested to be on a weekly basis, if the dog was to be treated with repeated dosing. Treatment delays for repeated dosing occurred during the course of the study due to adverse events or the decision of the investigator.

TABLE 9

Summary of study evaluations

| | Pretreatment Screening[a] | Day 0[b] | Day 4 | Day 7[b] | Day 11 | Day 14[b] | Day 18 | Day 21[b] | Day 25 | Day 60 | Day 90 |
|---|---|---|---|---|---|---|---|---|---|---|---|
| Informed Consent | X | | | | | | | | | | |
| Medical History & Demographics | X | | | | | | | | | | |
| Physical Exam | X | X | X | X | X | X | X | X | X | X | X |
| Weight & Vital Signs | X | X | X | X | X | X | X | X | X | X | X |
| Performance Score | X | | | | | | | | | | |
| Inclusion & Exclusion Criteria | X | | | | | | | | | | |
| Laboratory Values[c] | X | X | X | X | (X) | (X) | (X) | (X) | (X) | (X) | (X) |
| Imaging[d] | X | (X) | (X) | (X) | (X) | (X) | (X) | (X) | (X) | (X) | (X) |
| Biopsy | X | | | | | | | | | | |
| Research Bloodwork | X | | | | | | | | | | |
| Tumor Measurements & Photographs | X | X | | X | | X | | X | | X | X |
| Assign study dog number | X | | | | | | | | | | |
| Enrollment | X | | | | | | | | | | |
| IT *C. novyi*-NT | | X | | X | | X | | X | | X | |
| IV Fluid Therapy[e] | | X | | X | | X | | X | | X | |

TABLE 9-continued

Summary of study evaluations

| | Pretreatment Screening[a] | Day 0[b] | Day 4 | Day 7[b] | Day 11 | Day 14[b] | Day 18 | Day 21[b] | Day 25 | Day 60 | Day 90 |
|---|---|---|---|---|---|---|---|---|---|---|---|
| SQ Fluid Therapy[f] | | X | | X | | X | | X | | | |
| Study completion[g] | | | | | | | | | | | X |

[a]Screening evaluations undertaken 1-14 days prior to treatment.
[b]Patient monitored 6 hours post-treatment. Evaluation made every 15 minutes for 1st hour post-treatment, every 30 minutes for 2nd hour post treatment and every 60 minutes for 3rd-6th hour post-treatment.
[c]Laboratory values include: complete blood count, serum biochemistry panel, prothrombin time, thromboplastin time and urinalysis. (X)—at discretion of the investigator.
[d]Diagnostic imaging including: radiographs, ultrasound examination, or computed tomography.
[e]Crystalloid at 4 mL/kg/hr for two hours.
[f]Crystalloid at 20 mL/kg.
[g]Following study completion and if systemic antibiotics were required to manage adverse events, it was recommended to administer doxycycline 5-10 mg/kg orally twice a day (PO BID) to dogs for 3 months.

Sixteen dogs, 9 neutered males, 1 entire (intact) male, and 6 neutered females, were enrolled in the study. (Table 6). Their demographics and tumor characteristics are given in Table 6. Enrolled cases exhibited diverse breeds, weights and ages. Cases were previously diagnosed with naturally occurring cancers representing a variety of histological origins: 13 dogs had a diagnosis of soft tissue sarcoma (81.3%), 1 osteosarcoma (6.3%), 1 melanoma (6.3%) and 1 mast cell tumor (6.3%). Of the 13 soft tissue sarcomas, histologic subtype was available for 11 and included: 4 hemangiopericytomas (30.8%), 3 peripheral nerve sheath tumors (23.1%), 1 synovial cell sarcoma (7.7%), 1 myxosarcoma (7.7%), 1 rhabdosarcoma (7.7%) and 1 fibrosarcoma (7.7%). The mean weight of dogs in the trial was 29.4 kg (range 8.1-44.3 kg) and their mean age was 10.9 years (range: 7.2-14.3 years). Thirteen dogs had a diagnosis of soft tissue sarcoma, and one each had a diagnosis of osteosarcoma, malignant melanoma, and mast cell tumor. Of the 13 soft tissue sarcomas, six were available for immunohistochemistry (IHC). All six were positive for S100 and negative for smooth muscle actin, suggesting the diagnosis of a sarcoma subtype called peripheral nerve sheath tumors. Seven of the tumors were grade I, five were grade II, and four were grade III. Eight dogs had previous surgical therapy for their cancers.

Preparation and IT Injection of *C. novyi*-NT Spores in Spontaneous Canine Tumors

*C. novyi*-NT spores for use in the comparative canine study were produced as previously described (Dang, et al., 2001, Bettegowda, et al., 2006). In brief, bacteria were cultured in sporulation medium for at least two weeks to ensure maximum yield of mature spores. Mature spores were purified through two consecutive, continuous Percoll gradients followed by four washes and re-suspensions in PBS. Sterility testing of the final product was performed by culturing product in Soybean-Casein Digest Medium and Thioglycollate Medium in accordance with FDA 21CFR610.12 guidelines (Nelson Laboratories, Salt Lake City, Utah). Germination efficiency assays were performed under anaerobic conditions on *Brucella* agar with 5% horse blood to ensure the spores meet preset viability criteria. Spores were packaged in sterile 1.8 mL cryovials with O-ring sealed screw caps (Simport, Beloeil, Canada) at a volume of 1000 µL and a concentration of $1 \times 10^9$ spores/mL. *C. novyi*-NT cryovials were stored at 2-8° C. For dosing, a 0.4 mL aliquot of the stock spore solution was packaged into 0.5 mL cryovials. After dosing, the cryovials and unused *C. novyi*-NT spores were discarded according to applicable regulations for disposal of Biosafety Level 2 material. Prior to IT injection, spores were re-suspended with a vortex, mixing at maximum speed for 10 seconds for a total of three times before being withdrawn into a 1 mL syringe. The injection site was aseptically prepared. If available, ultrasound or computed tomography (CT) was used to identify a necrotic region of the tumor. If a necrotic region was not identified, the injection was directed to the center of the tumor. The needle was inserted once into the pre-defined region and 100 µL of spore suspension ($1 \times 10^8$ *C. novyi*-NT spores) were dispensed with even pressure. The injection needle was removed slowly and the injection site sterilized. All dogs received at least 1 cycle of an IT dose of $1 \times 10^8$ spores in 100 µL saline (biosurgery): 3 dogs received a single treatment cycle, 13 dogs received more than 1 and up to 4 treatment cycles. Dogs could receive up to 4 cycles of biosurgery with a one-week interval between cycles. Treated dogs were followed for at least 90 days after the first IT injection. Extended follow-up for disease progression and survival were warranted when available. Early withdrawal from the study was allowed for toxicity or progressive disease.

Study evaluations were undertaken as described in Table 9. Pre-screening evaluations were conducted 1 to 14 days before the first cycle of biosurgery. Dogs were monitored periodically on both an inpatient and outpatient basis during the study. Laboratory samples were taken as defined in Table 9 and included a complete blood count, serum biochemistry, prothrombin time, partial thromboplastin time, and urinalysis. Imaging was performed at screening and included regional CT, thoracic radiography, and abdominal ultrasonography. Additional imaging may be conducted during the study at the investigator's discretion.

Adverse events were evaluated, where possible, using the Veterinary Co-operative Oncology Group—Common Terminology Criteria for Adverse Events (VCOG-CTCAE) v1.0 (Veterinary Co-operative Oncology Group, 2004), with terminology from the Veterinary Dictionary for Drug Related Affairs (VeDDRA) rev.4 (European Medicines Agency, 2012). Terminologies for adverse events related to *C. novyi*-NT germination (target lesion reactions) are defined in Table 10. Clinical observations without appropriate VeDDRA or target lesion reaction terminology were classified separately as uncoded signs (Table 11). Relationship to *C. novyi*-NT therapy was determined by the reporting investigator.

TABLE 10

Coded terms to describe tumor adverse events associated with *C. novyi*-NT activity

| System Organ Class (SOC) Term | High Level Term (HLT) | Preferred Term (PT) | Low Level Term (LLT) |
|---|---|---|---|
| Target lesion reaction | Tumor inflammation | Tumor abscess | Tumor abscess |
| Target lesion reaction | Tumor inflammation | Tumor abscess | Tumor closed wound |
| Target lesion reaction | Tumor inflammation | Tumor abscess | Tumor malodorous |
| Target lesion reaction | Tumor inflammation | Tumor abscess | Tumor necrosis |
| Target lesion reaction | Tumor inflammation | Tumor abscess | Tumor open wound |
| Target lesion reaction | Tumor inflammation | Tumor abscess | Tumor tissue loss |
| Target lesion reaction | Tumor inflammation | Tumor abscess | Tumor tissue sloughing |
| Target lesion reaction | Tumor inflammation | Tumor abscess | Tumor ulceration |
| Target lesion reaction | Tumor inflammation | Tumor consistency change | Tumor consistency change |
| Target lesion reaction | Tumor inflammation | Tumor consistency change | Tumor firmer |
| Target lesion reaction | Tumor inflammation | Tumor consistency change | Tumor softer |
| Target lesion reaction | Tumor inflammation | Tumor discharge | Tumor bleeding |
| Target lesion reaction | Tumor inflammation | Tumor discharge | Tumor bloody discharge |
| Target lesion reaction | Tumor inflammation | Tumor discharge | Tumor discharge |
| Target lesion reaction | Tumor inflammation | Tumor discharge | Tumor purulent discharge |
| Target lesion reaction | Tumor inflammation | Tumor discharge | Tumor serous discharge |
| Target lesion reaction | Tumor inflammation | Tumor inflammation | Increased tumor heat |
| Target lesion reaction | Tumor inflammation | Tumor inflammation | Increased tumor warmth |
| Target lesion reaction | Tumor inflammation | Tumor inflammation | Tumor edematous |
| Target lesion reaction | Tumor inflammation | Tumor inflammation | Tumor inflammation |
| Target lesion reaction | Tumor inflammation | Tumor inflammation | Tumor inflammatory reaction |
| Target lesion reaction | Tumor inflammation | Tumor inflammation | Tumor pruritis |
| Target lesion reaction | Tumor inflammation | Tumor inflammation | Tumor swollen |
| Target lesion reaction | Tumor inflammation | Tumor pain | Tumor pain |
| Target lesion reaction | Tumor inflammation | Tumor skin disorder | Tumor bruising |
| Target lesion reaction | Tumor inflammation | Tumor skin disorder | Tumor discoloration |
| Target lesion reaction | Tumor inflammation | Tumor skin disorder | Tumor erythema |
| Target lesion reaction | Tumor inflammation | Tumor skin disorder | Tumor petichiation |
| Target lesion reaction | Tumor inflammation | Other tumor disorder | Other tumor disorder |
| Target lesion reaction | Tumor inflammation | Tumor pain | Tumor discomfort |

TABLE 11

Signs not attributable in VeDDRA to underlying clinical entity or *C. novyi*-NT related target lesion reaction

| Adverse Event (Preferred Term) | G-I | G-II | G-III | G-IV | # of dogs (with at least 1 occurrence of AE) | Total |
|---|---|---|---|---|---|---|
| Uncoded sign | 15 | 2 | | 1[a] | 5 | 18 |

[a]Grade IV decrease in blood eosinophils reported by investigator.

Longest diameter tumor measurements of the target (injected) lesion were made on day 0, day 7, day 14, day 21, day 60 and day 90 post-treatment (Table 9). Non-target and new lesions were recorded but not measured. The best overall target response was evaluated on or after the day 21 study visit: complete response (CR) was defined as the complete disappearance of the target lesion; partial response (PR) was defined as at least a 30% decrease in the longest diameter of the target lesion; and progressive target disease (PD) was defined as at least a 20% increase in the longest diameter of the target lesion or the appearance of new nontarget lesions. Stable disease (SD) was defined as insufficient decrease or increase in the longest diameter of the target lesion to qualify as CR, PR, or PD. In the case of *C. novyi*-NT related abscesses, medical, or surgical debridement of necrotic tissue was at the discretion of the investigator.

Evaluation of surgical samples and necropsies were conducted by board certified veterinary pathologists. Tissue specimens were fixed in 10% neutral buffered formalin and embedded in paraffin. Slides stained with H&E and or gram stained slides were prepared for evaluation according to standard procedure guidelines. For immunohistochemistry (IHC), formalin-fixed, paraffin-embedded tumor tissue was sectioned at 5 µm, deparaffinized in xylene, and rehydrated through graded alcohols. Antigen retrieval was done using unmasking solution (Vector Laboratories, Burlingame, Calif.). Primary antibodies S100 (DAKO, Carpinteria, Calif.) and anti-smooth muscle actin (DAKO, Carpinteria, Calif.) were used at 1:100. Secondary antibodies (Vector Laboratories, Burlingame, Calif.) labeled with DAB were used at 1:500. Sections were incubated with ABC reagent (Vector Laboratories, Burlingame, Calif.) and counterstained with hematoxylin. Tumor grades were assigned to each based on published criteria (Dennis, et al., 2011, Patnaik, et al., 1984, Smedley, et al., 2011, Sabattini, et al., 2014).

Example 7

Intratumoral (IT) Administration of *C. novyi*-NT—Study 1 Results

All dogs received at least one cycle of biosurgery, with 53 cycles given of a maximum of 64 planned. The majority of dogs, 10 of 16, received the intended four cycles. Cycles of biosurgery were typically one week apart. No placebo control or masking was used.

For dogs showing early tumor responses, toxicity, or progressive disease after the first cycle, subsequent cycles were stopped. The most common adverse events were consistent with local infection at the *C. novyi*-NT spore injection site, including: fever (17 incidents), tumor inflammation (12 incidents), tumor abscess (10 incidents), anorexia (nine incidents), and lethargy (six incidents) (Table 12). Clinical signs of an inflammatory response at the injected target lesion site was observed in 14 of 16 dogs (87.5%), including: tumor inflammation (12/14), tumor abscess (7/14), tumor pain (5/14), and tumor discharge (4/14) (Table 13).

TABLE 12

Summary of adverse events observed throughout study

| Adverse Event (Preferred Term) | G-I | G-II | G-III | G-IV | # of dogs (with at least 1 occurrence of AE) | Total |
|---|---|---|---|---|---|---|
| Hyperthermia | 14 | 3 | | | 10 | 17 |
| Tumor inflammation | 7 | 4 | 1 | | 12 | 12 |
| Tumor abscess | 6 | 3 | 1 | | 8 | 10 |
| Anorexia | 7 | 2 | | | 8 | 9 |
| Lethargy | 3 | 2 | 1 | | 6 | 6 |
| Lameness | 5 | | 1 | | 6 | 6 |
| Oedema | 5 | 1 | | | 5 | 6 |
| Hypertension | 6 | | | | 4 | 6 |
| Neutrophilia | 6 | | | | 6 | 6 |
| Tumor discharge | 6 | | | | 4 | 6 |
| Anaemia | 4 | | 1 | | 5 | 5 |
| Diarrhoea | | 3 | 1 | | 2 | 4 |
| Tumor pain | 3 | 1 | | | 4 | 4 |
| Leucocytosis | 4 | | | | 3 | 4 |
| Lymphadenitis | 4 | | | | 4 | 4 |
| Tumor consistency change | 3 | | | | 3 | 3 |
| Leucopenia | | 1 | | 1 | 1 | 2 |
| Thrombocytopenia | 1 | | | 1 | 2 | 2 |
| Localized pain | | 1 | 1 | | 2 | 2 |
| Lymphopenia | 1 | | 1 | | 2 | 2 |
| Change in blood protein | 1 | 1 | | | 2 | 2 |
| Emesis | 1 | 1 | | | 2 | 2 |
| Fluid in abdomen | 1 | 1 | | | 1 | 2 |
| General pain | 1 | 1 | | | 2 | 2 |
| Electrolyte disorder | 2 | | | | 2 | 2 |
| Impaired consciousness | 2 | | | | 2 | 2 |
| Tumor skin disorder | 2 | | | | 2 | 2 |
| Neutropenia | | | 1 | | 1 | 1 |
| Malaise | | 1 | | | 1 | 1 |
| Muscle weakness | | 1 | | | 1 | 1 |
| Recumbency | | 1 | | | 1 | 1 |
| Steatitis | | 1 | | | 1 | 1 |
| Digestive tract haemorrhage | | 1 | | | 1 | 1 |
| Skin and tissue infection | | 1 | | | 1 | 1 |
| Arrhythmia | 1 | | | | 1 | 1 |
| Bone and joint disorder | 1 | | | | 1 | 1 |
| Cardiac enlargement | 1 | | | | 1 | 1 |
| Digestive tract disorder | 1 | | | | 1 | 1 |
| Eosinophilia | 1 | | | | 1 | 1 |
| Erythema | 1 | | | | 1 | 1 |
| Hepatomegaly | 1 | | | | 1 | 1 |
| Hepatopathy | 1 | | | | 1 | 1 |
| Injection site pruritus | 1 | | | | 1 | 1 |
| Lymphocytosis | 1 | | | | 1 | 1 |
| Murmur | 1 | | | | 1 | 1 |
| Nausea | 1 | | | | 1 | 1 |
| Palpable mass | 1 | | | | 1 | 1 |
| Pulmonary disorder | 1 | | | | 1 | 1 |
| Skin haemorrhage | 1 | | | | 1 | 1 |
| Urine abnormalities | 1 | | | | 1 | 1 |
| Total | | | | | | 153 |

TABLE 13

Summary of clinical evidence of germination and response from *C. novyi*-NT therapy

| Case ID | Clinical evidence of germination[a] | Clinical response[b] |
|---|---|---|
| 01-R02 | Tumor inflammation, skin disorder and discharge | PD |
| 04-R01 | Tumor inflammation and pain | CR |
| 04-R02 | Tumor inflammation and abscess | PR |
| 04-R03 | Tumor inflammation, consistency change, discharge and tumor pain | CR |
| 04-R04 | Tumor inflammation and pain | NE |
| 04-R05 | Tumor inflammation, consistency change, skin disorder and pain | PR |
| 04-R06 | Tumor inflammation, abscess and discharge | CR |
| 04-R08 | Tumor abscess and discharge | NE |
| 10-R01 | — | PD |
| 10-R02 | Tumor inflammation, abscess and pain | SD |
| 11-R01 | Tumor inflammation and abscess | PR |
| 11-R02 | Tumor inflammation | SD |
| 11-R04 | Tumor abscess and consistency change | SD |
| 16-R02 | Tumor inflammation | PD |
| 16-R03 | Tumor inflammation and abscess | SD |
| 26-R01 | — | SD |

[a]Clinical evidence of *C. novyi*-NT germination on or after day 0 of the study and includes target lesion reactions (FIG. 5).
[b]Best response of the target lesion, as defined by the study protocol, after day 21 of the study: CR - complete response; PR - partial response; SD - stable disease; PD - progressive disease; NE - not evaluable for response after on or after day 21 of the study.

Early-Onset Adverse Events

Early-onset adverse events refer to the events occurring within the first 7 days following the first treatment cycle (13 dogs) or a single treatment cycle (3 dogs). A variety of adverse (AE) event findings were noted across multiple cases. The early-onset adverse events that occurred within 7 days either after the 1$^{st}$ treatment cycle (13 dogs that have received multiple cycles) or after the single treatment cycle (3 dogs that have received only one cycle) are summarized in Table 14.

TABLE 14

Summary of early onset[a] adverse events of any grade during the first treatment cycle

| Adverse Event | Type | Number of dogs[b] (N = 16) | Incidence (%) |
|---|---|---|---|
| Tumor inflammation | Target Lesion reaction | 9 | 56.3% |
| Anorexia | General signs or symptoms | 4 | 25.0% |
| Edema | General signs or symptoms | 4 | 25.0% |
| Fever | General signs or symptoms | 4 | 25.0% |
| WBC increased | Blood and lymphatic system | 2 | 12.5% |
| Hypertension | Circulatory disorders | 2 | 12.5% |
| Lethargy | General signs or symptoms | 2 | 12.5% |
| Pain | General signs or symptoms | 2 | 12.5% |
| Tumor abscess | Target Lesion reaction | 2 | 12.5% |
| Hb decreased | Blood and lymphatic system | 1 | 6.3% |
| MCV decreased | Blood and lymphatic system | 1 | 6.3% |
| Neutrophils increased | Blood and lymphatic system | 1 | 6.3% |
| RBC decreased | Blood and lymphatic system | 1 | 6.3% |
| WBC decreased | Blood and lymphatic system | 1 | 6.3% |
| Blood in feces | Digestive tract disorders | 1 | 6.3% |
| Diarrhea | Digestive tract disorders | 1 | 6.3% |
| Nausea | Digestive tract disorders | 1 | 6.3% |
| Regurgitation | Digestive tract disorders | 1 | 6.3% |
| Vomiting | Digestive tract disorders | 1 | 6.3% |
| Injection site pruritus | Injection site reactions | 1 | 6.3% |

TABLE 14-continued

Summary of early onset[a] adverse events of any grade during the first treatment cycle

| Adverse Event | Type | Number of dogs[b] (N = 16) | Incidence (%) |
|---|---|---|---|
| Tumor bleeding | Target Lesion reaction | 1 | 6.3% |
| Tumor erythema | Target Lesion reaction | 1 | 6.3% |

[a]Up to and less than 7 days after first treatment.
[b]Number of dogs with at least one adverse event of any grade Common early onset adverse event findings included: target tumor lesion reactions, alterations in general signs and symptoms, and blood and lymphatic system abnormalities. The majority of early onset adverse events were mild to moderate (Grade I-II), with tumor inflammation, anorexia, tumor edema, and fever being the most commonly observed events. Grade III tumor abscess and Grade III tumor inflammation were noted in two cases (10-R02 and 16-R03). Early onset adverse event findings appear consistent with the anticipated tumor inflammatory reactions resulting from the mechanism of action of the *C. novyi*-NT therapeutic.

Late-Onset Adverse Events

A subset of 3 dogs received only a single treatment cycle (as of Dec. 2, 2012). Late-onset adverse events refer to the events occurring after 7 days following the single treatment cycle and are summarized in Table 15 for the 3 dogs (04-R4, 10-R02, and 11-R01). The majority of late-onset adverse events were mild to moderate (Grade I-II) and 11 of the 12 later onset findings were noted in a single subject 04-R04. This dog presented with chondroblastic osteosarcoma of the right forelimb with a LD measurement of 94.5 mm at baseline (CT measurement not available). Amputation was pursued 20 days after *C. novyi*-NT spore injection due to progressive disease. The other two subjects have well tolerated the single treatment cycle. Their late-onset AE was exclusively limited to a mild fever (Grade I).

In summary, the safety profile observed following one treatment cycle of *C. novyi*-NT IT administration of $1\times10^8$ spores suggested suitable tolerability. The early-onset and late-onset adverse events were consistent with the anticipated tumor inflammatory reactions resulting from the mechanism of action of *C. novyi*-NT. The adverse events have been monitored and managed effectively as disclosed herein.

The adverse events noted when dogs were given multiple treatment cycles of *C. novyi*-NT by IT administration are summarized in Table 9 for adverse events (AEs) of any Grades and in Table 10 for AEs of Grade III and above.

The variety and incidence of adverse event findings following multiple cycles of treatment was broadly similar to that observed following a single treatment cycle. Likewise, the onset of events appeared to be largely consistent with what was observed following a single treatment cycle: of 169 findings across all cases, only 30 were noted more than seven days following a prior dose. Similarly, tumor inflammation, anorexia, and fever were the most commonly observed events. Adverse events that occurred in more than one case included: target lesion reactions, alterations in general signs and symptoms, blood and lymphatic system abnormalities, lameness, hypertension, lymphadenopathy, diarrhea, and new masses. The majority (about 95%) of findings were mild to moderate in intensity (Grade I to II).

Severe Adverse Events

Severe adverse events (Grade III and greater) were noted in 5 cases (Table 16). Subject 04-R05 experienced a Grade III increase in neutrophil count. Subject 10-R01 experienced Grade III anemia, lethargy, muscle weakness, myositis, pain and recumbency. Extensive metastatic disease, while not observed at baseline, was diagnosed following necropsy of case 10-R01 at Day 60; progressive disease may have influenced adverse event findings in this case. Subject 10-R02 experienced a Grade III tumor abscess. Subject 11-R01 experienced a Grade IV decreased thrombocyte count 93 days after first treatment cycle which resolved without intervention. Symptoms resolved 21 days after the Day 93 visit without any medical treatment. Notably, this subject also exhibited Grade I and Grade III symptoms of thrombocytopenia at screening and baseline, respectively. Subject 16-R03 experienced Grade III diarrhea, lameness and tumor inflammation that resolved within one week.

TABLE 15

Summary of later onset[a] adverse events of any grade after first treatment cycle

| Adverse Event | Type | Number of dogs[b] (N = 3) | Incidence (%) | Days to Finding[c] |
|---|---|---|---|---|
| Fever | General signs or symptoms | 1 | 33.3% | 9 |
| Pain | General signs or symptoms | 1 | 33.3% | 20 |
| Surgical site disorder | Systemic disorders NOS | 1 | 33.3% | 24 |
| Neutrophils increased | Blood and lymphatic system | 1 | 33.3% | 34 |
| RBC decreased | Blood and lymphatic system | 1 | 33.3% | 34 |
| Eosinophils increased | Blood and lymphatic system | 1 | 33.3% | 61 |
| WBC increased | Blood and lymphatic system | 1 | 33.3% | 61 |
| Tumor new mass | Neoplasia | 1 | 33.3% | 82 |
| Lymphadenopathy | Lymph node disorders | 1 | 33.3% | 82 |
| Thrombocytes decreased | Blood and lymphatic system | 1 | 33.3% | 93 |

[a]After 7 days following a single treatment only.
[b]Number of dogs with at least one adverse event of any grade.
[c]From day of first treatment.

TABLE 16

Summary of adverse events greater than or equal to Grade III for all treatment cycles

| Adverse Event | Type | Number of dogs[a] (N = 16) | Incidence (%) |
|---|---|---|---|
| Lameness | Musculoskeletal disorders | 3 | 18.8% |
| Pain | General signs or symptoms | 2 | 12.5% |
| Anemia | Blood and lymphatic system | 1 | 6.3% |
| Neutrophils decreased | Blood and lymphatic system | 1 | 6.3% |
| Thombocytes decreased | Blood and lymphatic system | 1 | 6.3% |
| Diarrhea | Digestive tract disorders | 1 | 6.3% |
| Lethargy | General signs or symptoms | 1 | 6.3% |
| Steatitis | General signs or symptoms | 1 | 6.3% |
| Myositis | Musculoskeletal disorders | 1 | 6.3% |
| Tumor abscess | Target Lesion reaction | 1 | 6.3% |
| Tumor inflammation | Target Lesion reaction | 1 | 6.3% |

[a]Number of dogs with at least one adverse event of any grade.

Two dogs had documented new masses during the study. A rectal mass was identified in subject 04-R04 on Day 82 and a lytic vertebral lesion of T1 in subject 10-R01 on Day 9. These findings may represent a metastasis or a second distinct pathology. In both cases, the relationship to C. novyi-NT therapy was unclear.

Response from C. novyi-NT Therapy

In summary, C. novyi-NT IT treatment in companion dogs at a dose of 1×10⁸ spores per cycle of therapy for up to 4 cycles is well tolerated. Most adverse events possibly or probably related to drug that were greater than Grade III resolved within one week. Expected adverse events have been largely associated with local inflammatory changes following intratumoral therapy and generally resolved within one week. The adverse events and serious adverse events have been monitored and managed effectively as disclosed herein.

Given that C. novyi-NT IT administration was accompanied by broad evidence of biological activity, a preliminary assessment of primary tumor response using RECIST 1.1 was made and is summarized in Table 17 below.

TABLE 17

Summary of clinical evidence of germination and response from C. novyi-NT therapy

| Case ID | Clinical evidence of germination[a] | Clinical Response[b] |
|---|---|---|
| 01-R02 | Tumor inflammation, skin disorder and disorder | PD |
| 04-R01 | Tumor inflammation and pain | CR |
| 04-R02 | Tumor inflammation and abscess | PR |
| 04-R03 | Tumor inflammation, consistency change, discharge and tumor pain | CR |
| 04-R04 | Tumor inflammation and pain | NE |
| 04-R05 | Tumor inflammation, consistency change, skin disorder and pain | PR |
| 04-R06 | Tumor inflammation, abscess and discharge | CR |
| 04-R08 | Tumor abscess and discharge | NE |

TABLE 17-continued

Summary of clinical evidence of germination and response from C. novyi-NT therapy

| Case ID | Clinical evidence of germination[a] | Clinical Response[b] |
|---|---|---|
| 10-R01 | — | PD |
| 10-R02 | Tumor inflammation, abscess and pain | SD |
| 11-R01 | Tumor inflammation and abscess | PR |
| 11-R02 | Tumor inflammation | SD |
| 11-R04 | Tumor abscess and consistency change | SD |
| 16-R02 | Tumor inflammation | PD |
| 16-R03 | Tumor inflammation and abscess | SD |
| 26-R01 | — | SD |

Dogs were evaluated for best response on or after day 21 of the study. Three had a complete response (CR) to therapy, three had partial responses (PR), five had stable disease (SD), three had progressive disease (PD), and two dogs (04-R04 and 04-R08) were not evaluable for response because the injected tumor was surgically resected before day 21. The objective response rate for biosurgery was 37.5% (6 of 16 dogs; 95 percent confidence interval: 15.2-64.6%). Tumor abscesses and responses occurred after one to four cycles of biosurgery. Dog 11-R01 experienced a PR after a single cycle, 04-R03 had a CR after three cycles, dogs 04-R02 and 04-R05 had PRs after four cycles, while 04-R01 and 04-R06 had CRs after four cycles. FIGS. 7A-F and FIGS. 8A-F show representative changes in dogs with partial (11-R01) and complete responses (04-R03), respectively. Resolution of abscesses occurred with debridement and wound healing was complete after 2 to 4 weeks. However, overt abscess formation was not always observed before an objective response. Dogs 04-R01 and 04-R06 received 4 cycles of biosurgery, with tumor inflammation, but not abscessation, observed up to the day 21 study visit. Even so, complete responses were noted on the day 42 (unscheduled visit) and day 60 study visits in these two dogs, respectively.

Figure 9:
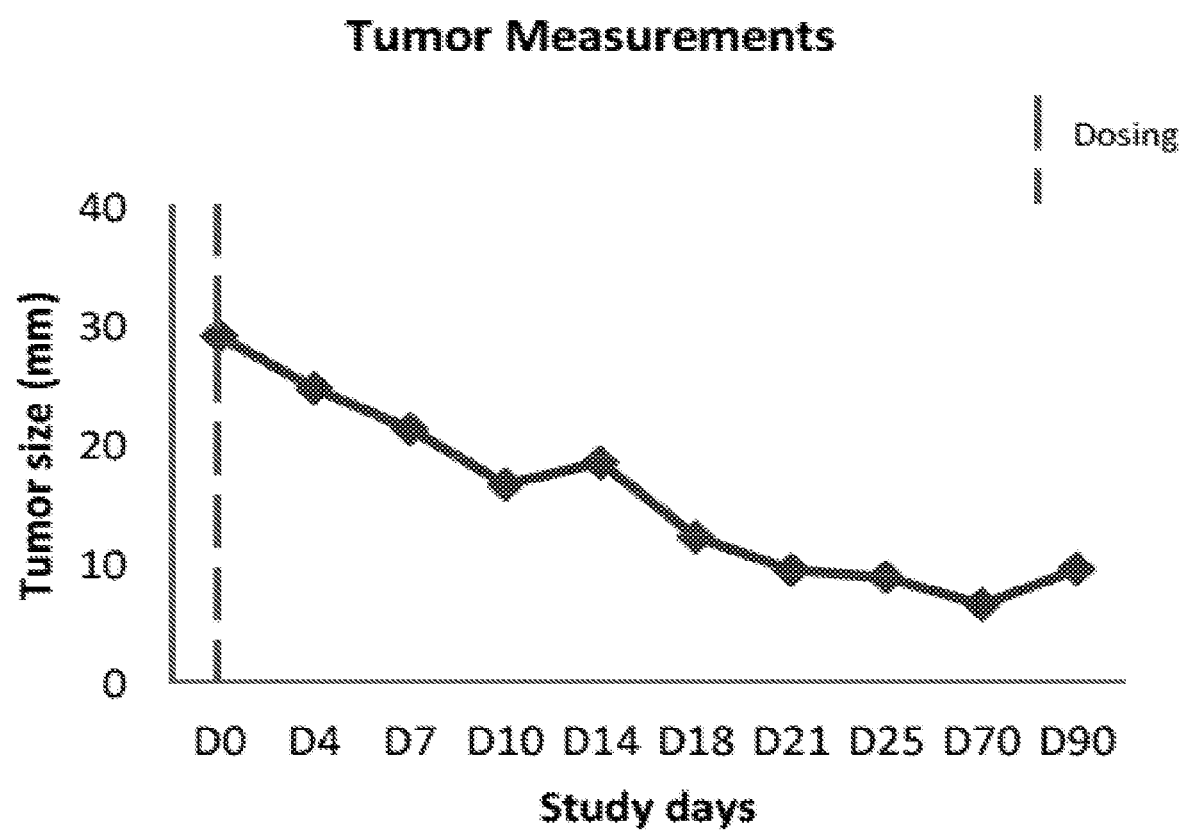

Individual subjects are discussed in more detail below:

Andy (11-R01, FIGS. 7A-F), a 10 year-old, neutered male, Maltese, presented with a grade II soft tissue sarcoma on the left pinna. His treatment history included surgery prior to enrollment. He received a single dose of C. novyi- NT spores on Jun. 18, 2012. Andy experienced Grade I tumor swelling on Day 1 (Jun. 19, 2012). Abscess formation led to ulceration of the tumor and discharge of purulent, necrotic material. The resulting wound healed without complication. During the extended follow-up period, a Grade IV thrombocytopenia was observed on Day 93 (Sep. 19, 2012) that resolved at a routine follow-up visit a few weeks later. A thickened cutaneous area of approximately 8 mm remained after wound healing (see FIG. 9 for a time course of tumor measurements over the course of the study). This may have represented scar tissue or residual tumor.

Molly (11-R02), a 12 year-old, neutered female, Labrador Retriever, presented with a grade II soft tissue sarcoma on the left stifle. She had no treatment history prior to enrollment. She received 3 cycles of IT C. novyi-NT spores, followed by 1 IV dose of 1×10$^8$ C. novyi-NT spores, 7 days after the 3rd IT dose. Her 1st, 2nd and 3rd IT doses on Jul. 11, 2012, Jul. 18, 2012, and Jul. 25, 2012, respectively. The single IV dose of C. novyi-NT spores was given on Aug. 1, 2012 due to lack of biological activity seen with the prior IT doses. The only adverse event noted was Grade I hypertension after the 3rd IT dose. Hypertension was transient and self-limiting, resolving within 1 hour. Molly's tumor was surgically removed on Day 30 (Aug. 10, 2012) for histologic analysis. The mass was confirmed to be a soft tissue sarcoma with areas of necrosis and inflammation. Bacteria were not present on gram stains, supporting lack of biological activity in this case.

Ricky (10-R01), a 13 year-old, male neutered, Golden retriever, presented with oral melanoma. His treatment history included surgery prior to enrollment. He received 2 cycles of IT C. novyi-NT spores. C. novyi-NT IT treatments were administered on Aug. 2, 2012 and Aug. 9, 2012. On Day 9 (Aug. 11, 2012), Ricky developed sudden onset of cervical pain and rear leg neurological deficits 2 days after the 2nd treatment cycle. Grade III anemia was also noted. An MRI was performed and revealed probable cervical steatitis and cervical spinal cord compression. Corticosteroids and gastrointestinal protectants were administered and Ricky recovered after 3 days. No changes in the oral melanoma were noted and no additional C. novyi-NT treatments were administered. On Day 21 (Aug. 23, 2012), an MRI was performed and showed improvement in the previously described steatitis; however, metastatic pulmonary nodules were noted on CT of the thorax. Excision of the oral melanoma was performed. A human tyrosinase melanoma vaccine was started on Aug. 30, 2012. On Day 42 (Sep. 13, 2012), Ricky presented with recurrent cervical pain and forelimb pain (2 weeks after discontinuation of corticosteroids) and 2 weeks after receiving the melanoma vaccine. Medical management with pain medication did not result in improvement after 4 days so corticosteroids were restarted. On Day 46, Grade III anemia and elevated BUN were noted. A presumptive gastrointestinal bleed was treated with gastrointestinal protectants. On Day 60, Ricky collapsed and developed hematemesis. Humane euthanasia was performed. A necropsy revealed disseminated metastatic melanoma including submandibular lymph node, mediastinal lymph node, mesenteric lymph node, kidney, and perispinal fat in the region of the cervical spine. No evidence of gastric or intestinal ulceration was found. The presumed cause for the two episodes of spinal pain is metastatic melanoma. The relationship to C. novyi-NT is uncertain.

Finnegan (04-R02), an 11 year-old, entire male, Golden Retriever, presented with a soft tissue sarcoma (hemangiopericytoma) on the right lateral metacarpus. His treatment history included surgery prior to enrollment. He received 4 cycles of IT C. novyi-NT spores. Adverse events were mild and well tolerated. Complete ablation of the tumor occurred after 4 cycles of treatment, leaving a margin of normal tissue about the site of the tumor. Finnegan received his 1st, 2nd, 3rd and 4th treatment cycles on Aug. 3, 2012, Aug. 10, 2012, Aug. 17, 2012 and Aug. 24, 2012, respectively. Administration of C. novyi-NT was associated with only Grade I adverse events reported after the 1st, 2nd and 3rd cycles. Grade I and II adverse events were noted 48 hours after the 4th dose. Tumor infection was noted and consisted of fever, leukocytosis, neutrophilia and tumor-associated pain and abscess formation. Infection progressed to abscess formation and ablation of the entire tumor with minimal debridement occurring 96 hours after the 4th dose. Tumor measurements at this visit were recorded in the morning prior to complete ablation of gross tumor later that day. Amputation of the limb was pursued instead of open-wound management on Day 25 (Aug. 28, 2012) and antibiotics were given. Finnegan recovered uneventfully from surgery and remains grossly tumor free 94 days (Nov. 5, 2012) after his first treatment.

Figure 10A:
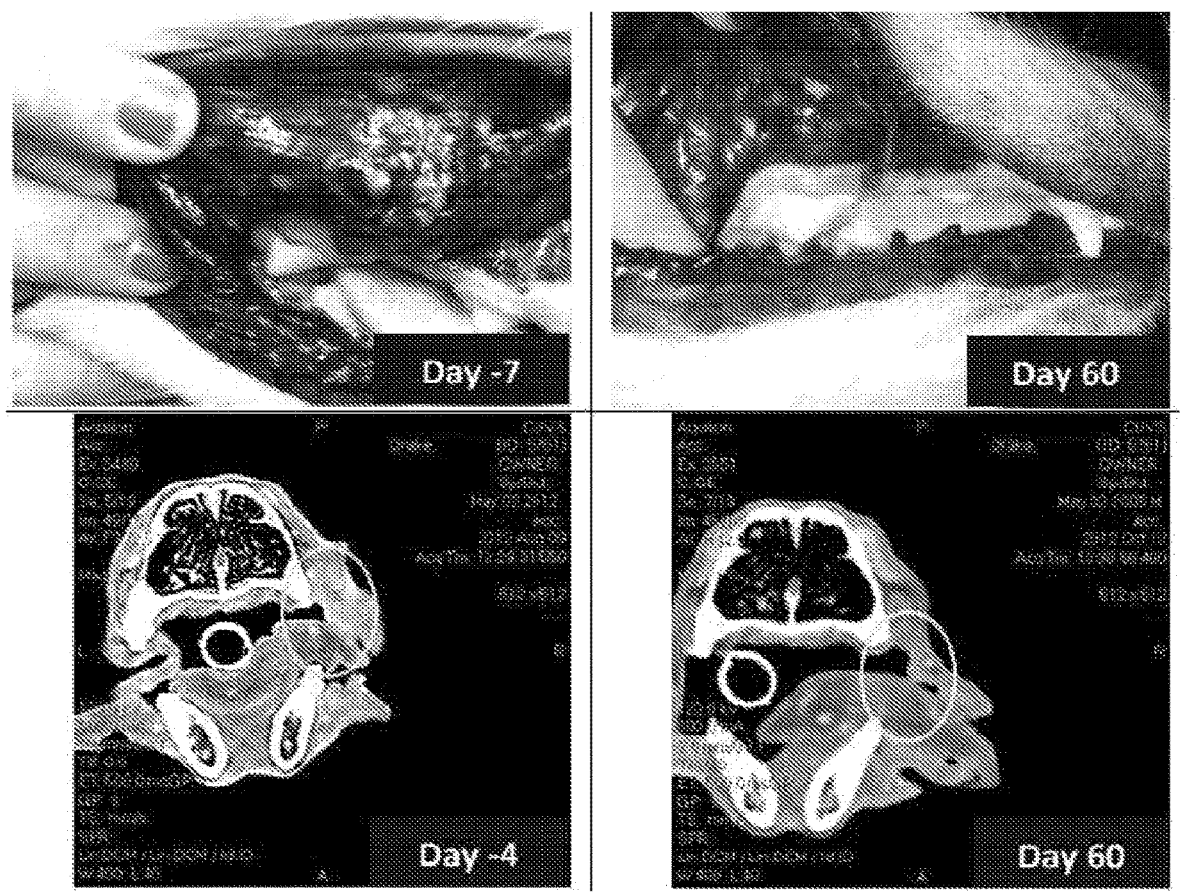
Figure 10B:
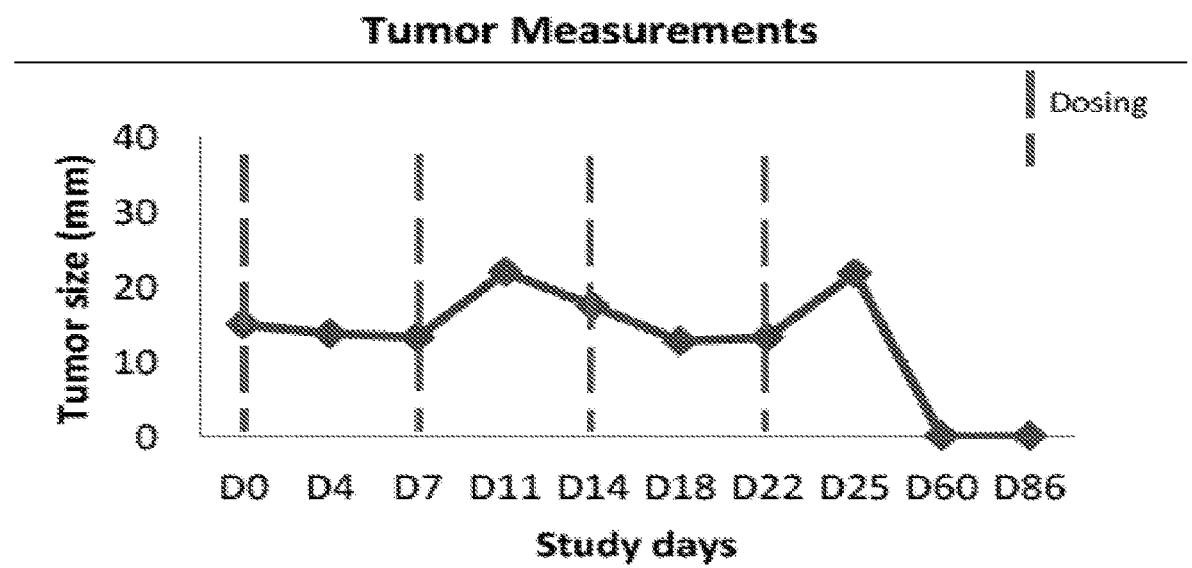

Drake (04-R01, FIG. 10A), a 7 year-old, neutered male, Golden Retriever, presented with a soft tissue sarcoma (fibrosarcoma) in the right mid maxillary region. He had no treatment history prior to enrollment. He received 4 cycles of IT C. novyi-NT spores. Adverse events were mild and well tolerated. Complete ablation of the tumor occurred after 4 cycles, leaving a margin of normal tissue about the site of the tumor. Drake received his 1st, 2nd, 3rd, and 4th treatments on Aug. 13, 2012, Aug. 20, 2012, Aug. 27, 2012, and Sep. 4, 2012, respectively. The intervals between 1st, 2nd, and 3rd doses were 7 days; while the interval between 3rd and 4th doses was 8 days in observance of a national holiday. Administration of C. novyi-NT was associated with mild adverse events, including Grade I lethargy and inappetence and Grade II vomiting and hematochezia reported 24-48 hours after the 1st cycle. These AEs were treated successfully with an anti-emetic and antibiotic. AEs were noted within 24 hours of the 4$^{th}$ dose, including Grade I tumor pain and swelling. Further evidence of tumor infection and abscess formation was not observed. Ablation of the tumor was evident on day 60 (Oct. 12, 2012) and the tumor was not measurable (see FIG. 10B for a time course of tumor measurements over the course of the study). The region was firm and remained slightly swollen and a CT scan was performed. Drake remains free of tumor on day 86 (Nov. 7, 2012) after 1st dose.

Figure 11:
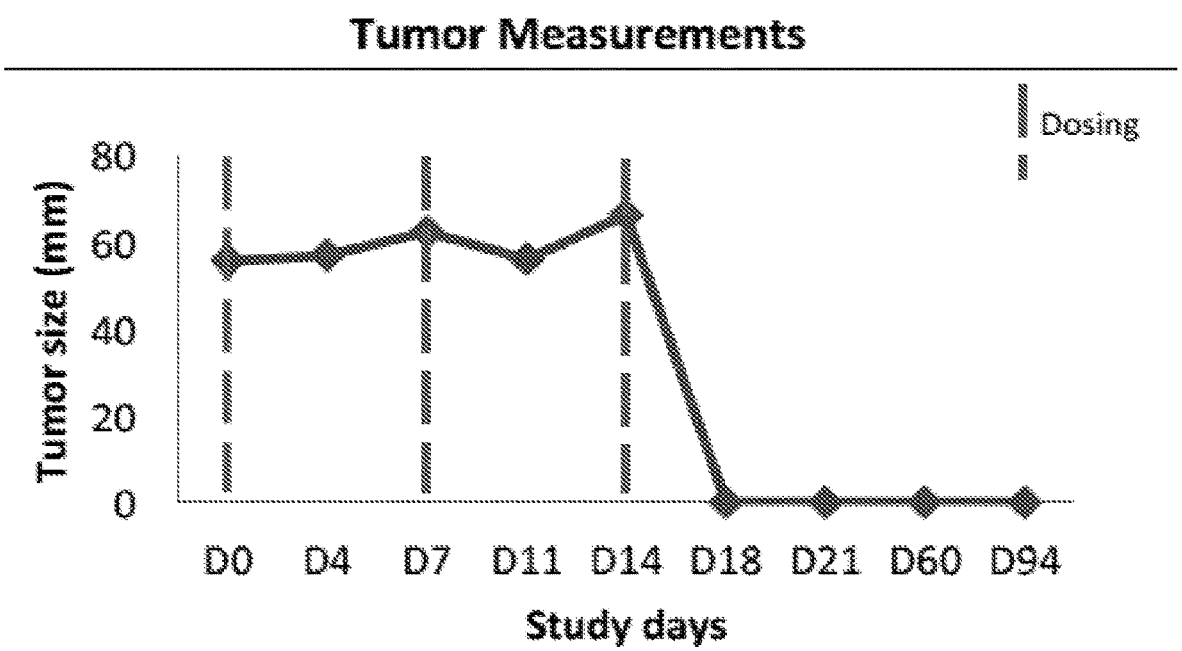

Baxter (04-R03, FIGS. 8A-F), a 9 year-old, neutered male, Boxer, presented with a grade II soft tissue sarcoma on the left medial antebrachium. He had no treatment history prior to enrollment. He received three cycles of IT C. novyi-NT spores. Adverse events were mild and well tolerated. Complete ablation of the tumor occurred after three injections, leaving a margin of normal tissue about the site of the tumor. Baxter received his 1st, 2nd and 3rd doses of C. novyi-NT spores on Aug. 17, 2012, Aug. 24, 2012, and Aug. 31, 2012, respectively. Administration of C. novyi-NT was well tolerated, with no study agent related toxicity reported after the 1st or 2nd dose. Study-related adverse events were noted 24 hours after the 3rd dose. These adverse events were associated with tumor infection and consisted of fever, anorexia, lethargy and tumor-associated pain, swelling and bleeding. Adverse events were mild (Grade II or lower) and were managed with supportive care and analgesics. C. novyi-NT related tumor infection progressed to involve the entire tumor and abscess formation. Surgical debridement of the tumor on Sep. 2, 2012 resulted in rapid resolution of AEs. Wound healing was without complication and complete by Oct. 16, 2012. Baxter remains grossly tumor free at 94 days (Nov. 19, 2012) after his first treatment (see FIG. 11 for a time course of tumor measurements over the course of the study).

Harley (26-R01), a 7 year-old, neutered male, Labrador Retriever, presented with a grade II soft tissue sarcoma (hemangiopericytoma) on the right paw. He had no treatment history prior to enrollment. He received 4 cycles of IT C. novyi-NT spores. The 1st, 2nd, 3rd and 4th doses were given on Aug. 20, 2012, Aug. 27, 2012, Sep. 4, 2012 and Sep. 10, 2012. The interval between doses was 6-8 days. A baseline elevation of temperature was noted at the time of the 1st and 2nd doses. IT treatment of C. novyi-NT spores was well tolerated with no adverse events reported. There was no response to therapy.

Ursula (04-R-04), an 11 year old, female spayed, Saint Bernard mix, presented with chondroblastic osteosarcoma of the right forelimb. Her treatment history included surgery prior to enrollment. She received a single IT dose of C. novyi-NT spores. No metastatic disease was present at enrollment. Following the first treatment on Aug. 31, 2012, tumor abscess formation and peritumoral inflammation was evident within the first 24 hours and medically managed with pain medication, warm compresses and intravenous crystalloids. After no improvement, the tumor/abscess was lanced on Day 2 (Sep. 2, 2012). Moderate serosanguineous fluid was present. An anaerobic culture isolated C. novyi. Antibiotics were administered starting on Day 4 (Sep. 4, 2012). The incision was managed as an open wound until Day 20 (Sep. 20, 2012) when amputation was pursued for progressive disease. Histopathology revealed severe necrosis and hemorrhage along with persisting chondroblastic osteosarcoma. Following amputation, an incision site infection was noted. Cultures did not reveal C. novyi. No adjuvant therapy was pursued following amputation. On Day 81 (Nov. 21, 2012), Ursula presented for rectal prolapse and was found to have rectal polyps. Thoracic radiographs performed at the time of this evaluation revealed pulmonary metastasis.

Gabriel (16-R02), a 9 year-old, neutered male, Labrador Retriever, presented with a grade I soft tissue sarcoma on the left lateral thigh. His treatment history included surgery prior to enrollment. He received 4 cycles of IT C. novyi-NT spores. IT administration of C. novyi-NT was generally well tolerated with a 1 week delay between the 1st and 2nd doses due to Grade II diarrhea that responded to medical management. Gabriel received his 1st, 2nd, 3rd and 4th doses on Sep. 12, 2012, Sep. 26, 2012, Oct. 3, 2012 and Oct. 10, 2012 respectively. Toxicity was mild and consisted mainly of diarrhea and constitutive symptoms. Grade II diarrhea was noted after each dose and responded well to medical management. After the 1st dose, a 1-week dose delay was implemented resulting in a 14 day interval between the 1st and 2nd doses. Dose delays were not implemented for further doses for Grade II diarrhea. Additionally, Grade II tumor swelling was observed on Day 4 (Sep. 16, 2012). Tumor size remained stable from DO (Sep. 12, 2012) to D63 (Nov. 14, 2012), the most recent study visit.

Buddy (04-R05), a 13 year-old, neutered male, Shetland sheepdog, presented with soft tissue sarcoma (rhabdomyosarcoma) on the right antebrachium. His treatment history included surgery, chemotherapy, and a previous C. novyi-NT clinical trial prior to enrollment. No metastatic disease was noted at the time of study entry. He received 4 cycles of IT C. novyi-NT spores. Clinically significant adverse events contemporaneous with C. novyi-NT were isolated to a Grade III neutropenia and fever following the 3rd cycle of therapy. This event resolved within 48 hours of medical management with intravenous antibiotics and fluid therapy. Buddy received his 1st, 2nd, 3rd and 4th treatment cycles on Sep. 20, 2012, Sep. 27, 2012, Oct. 5, 2012, and Oct. 12, 2012. Mild tumor inflammation (erythema, warmth, swelling) was noted associated with 2 of the 4 cycles. A transient decrease in tumor size was noted at Day 4 (Sep. 24, 2012). A new non-target lesion was noted near the primary tumor site on Day 21 (Oct. 12, 2012). The primary target tumor was stable at Day 61.

Amber (16-R03), a 10 year-old, neutered female, Shepherd, presented with a grade I soft tissue sarcoma on the left paw, palmar and dorsal surfaces. Her treatment history included surgery prior to enrollment. She received 4 cycles of IT C. novyi-NT spores. The 1st, 2nd, 3rd and 4th doses were given on Sep. 26, 2012, Oct. 3, 2012, Oct. 15, 2012, and Oct. 24, 2012. The interval between doses was 7-12 days. Amber experienced Grade II tumor swelling and pain after her 1st and 2nd doses. Grade I inappetence was noted on Day 2 (Sep. 28, 2012). On Day 8 (Oct. 4, 2012, 1 day after 2nd dose), a Grade I fever, Grade II tumor warmth and Grade III lameness was noted. Her tumor was lanced and analgesics were given. A Grade III diarrhea was noted on Day 11 (Oct. 7, 2012) and managed medically. Due to the tumor associated adverse events and diarrhea, the 3rd dose was delayed until Day 19 (Oct. 15, 2012). Grade II tumor swelling was again observed on Day 19, after the 3rd dose of C. novyi-NT and this was managed with analgesics. No adverse events were noted after the 4th dose.

Six (11-R04), a 9 year-old, neutered male, Husky, presented with a grade I soft tissue sarcoma on the right paw. She had no treatment history prior to enrollment. She received 4 cycles of IT C. novyi-NT spores. Six received the 1st, 2nd, 3rd and 4th doses on Oct. 1, 2012, Oct. 8, 2012, Oct. 15, 2012, and Oct. 22, 2012, respectively. Administration of C. novyi-NT spores was well tolerated with only mild adverse events observed. After the 1st dose, Grade I hypertension and fever were noted. Fever and hypertension were self-limiting and resolved within 1 and 2 hours of dosing respectively. On Day 4 (Oct. 5, 2012), the tumor was subjectively softer and a small area of ulceration (Grade I) was observed at the site of a previous biopsy. Ulceration continued to Day 31 (Nov. 1, 2012), the most current study visit. This ulceration may be associated with either the study agent or a complication of the biopsy required for study enrollment.

Belle (04-R06), an 11 year-old, female spayed, Labrador retriever, presented with a mast cell tumor (originally aspirated as a soft tissue sarcoma) on the right rear digit 3 with metastasis to the popliteal lymph node. She had no treatment history prior to enrollment. She received 4 cycles of IT C. novyi-NT spores. Adverse events were mild and limited to Grade I fever and Grade I tumor inflammation. Belle received the 1st, 2nd, 3rd and 4th treatment cycles on Oct. 19, 2012, Oct. 26, 2012, Nov. 2, 2012, and Nov. 9, 2012. Grade I fever contemporaneous with C. novyi-NT treatment and tumor inflammation. Fever and inflammation were self-resolving without the need for medical management other than protocol required subcutaneous fluids administered on scheduled study visits. Ulceration of the tumor was noted on Day 21 (Nov. 9, 2012). Photographs of the tumor sent to the investigator by the dog owner showed resolution of the ulceration and marked regression in the mass. An unscheduled visit was performed on Day 46 (Dec. 4, 2012) to capture tumor response assessment. Complete regression of the tumor was noted.

Frida (11-R01), a 7 year-old, female spayed, German shepherd mix, presented with a soft tissue sarcoma (hemangiopericytoma) on the right rear paw with possible lymph node metastasis (based on CT). Her treatment history included surgery prior to enrollment. She traveled with her owner from Mexico to participate in this clinical trial. She received 3 cycles of IT *C. novyi*-NT spores. Adverse events were limited to a waxing and waning fever for 48 hours, which resolved with intravenous fluids and NSAIDs. Frida received the 1st, 2nd, and 3rd cycles of therapy on Nov. 6, 2012, Nov. 14, 2012, and Nov. 21, 2012. The only significant adverse events included Grade I fever requiring hospitalization and fluids starting on Day 4 (Nov. 10, 2012) and progressing to Grade II fever on Day 5 (Nov. 11, 2012). The fever resolved after 48 hours. A Grade I fever was also noted after the 3rd cycle of therapy on Day 18 (Nov. 24, 2012). Tumor progression prompted amputation on Day 21 (Nov. 27, 2012).

Mhija (01-R02), a 7 year-old, neutered male, Border Collie, presented with soft tissue sarcoma (peripheral nerve sheath tumor) on the left thoracic flank. She had no treatment history prior to enrollment. She has received 3 cycles of IT *C. novyi*-NT spores. Adverse events were mild and well tolerated. Tumor inflammation, heat and serosanguineous to mucopurulent discharge are probably related to *C. novyi*-NT activity. A 4th cycle of *C. novyi*-NT spores is planned. Mhija received the 1st, 2nd and 3rd doses on Nov. 12, 2012, Nov. 20, 2012, and Nov. 27, 2012, respectively. The interval between 1st and 2nd doses was 8 days; while the interval between 2nd and 3rd doses was 7 days. Administration of *C. novyi*-NT was associated with mild, Grade I-II toxicity. Grade I nausea and regurgitation was noted after the 1st dose, with Grade I inappetence and lethargy noted after the 3rd dose. Toxicities resolved shortly with medical management. Most toxicities were localized to the tumor site, Grade I or II in severity (heat, inflammation, pruritis, serosanguineous to mucopurulent discharge and erythema) and occurring within 2 days of an administration of *C. novyi*-NT. Additionally, Grade I-II ventral edema was observed 2 days after the 1st and 3rd doses.

Tank (10-R02), a 10 year-old, male neutered, mixbreed, presented with soft tissue sarcoma (hemangiopericytoma) on the right flank. His treatment history included surgery prior to enrollment. He received 1 cycle of IT *C. novyi*-NT spores on Nov. 12, 2012. Grade I fever, decreased appetite, Grade II edema surrounding the tumor, and Grade III tumor abscess were noted on Day 4 (Nov. 16, 2012) following treatment. Medical management including pain medication, IV fluids, and broad-spectrum antibiotics were used to manage the abscess. Tumor inflammation and surrounding edema resolved on Day 11 (Nov. 23, 2012). Tank received a 2nd treatment cycle on Dec. 3, 2012. The interval between cycles was 21 days. The 2nd dose was delayed due to the antibiotics washout period.

Figure 12A:
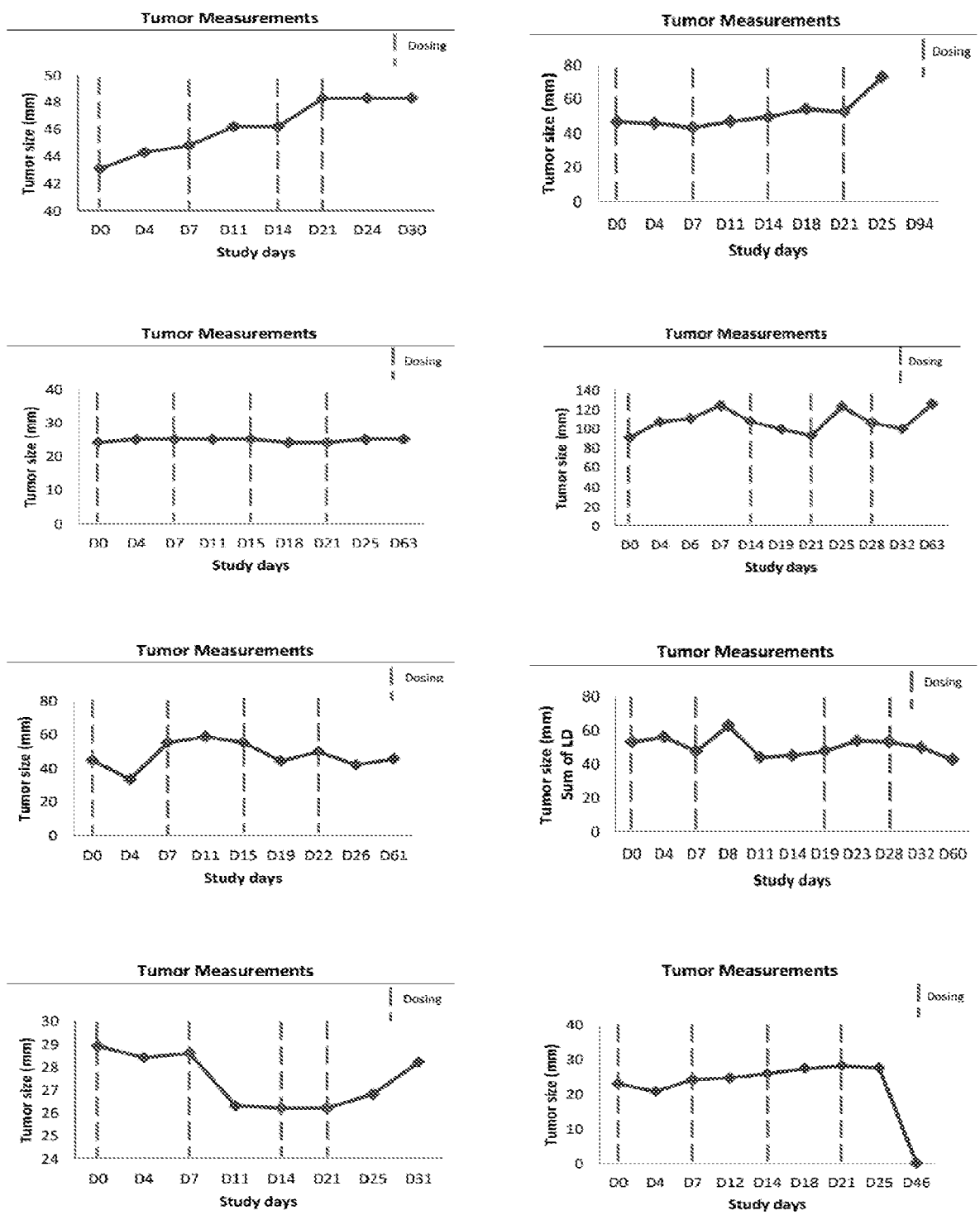
Figure 12B:
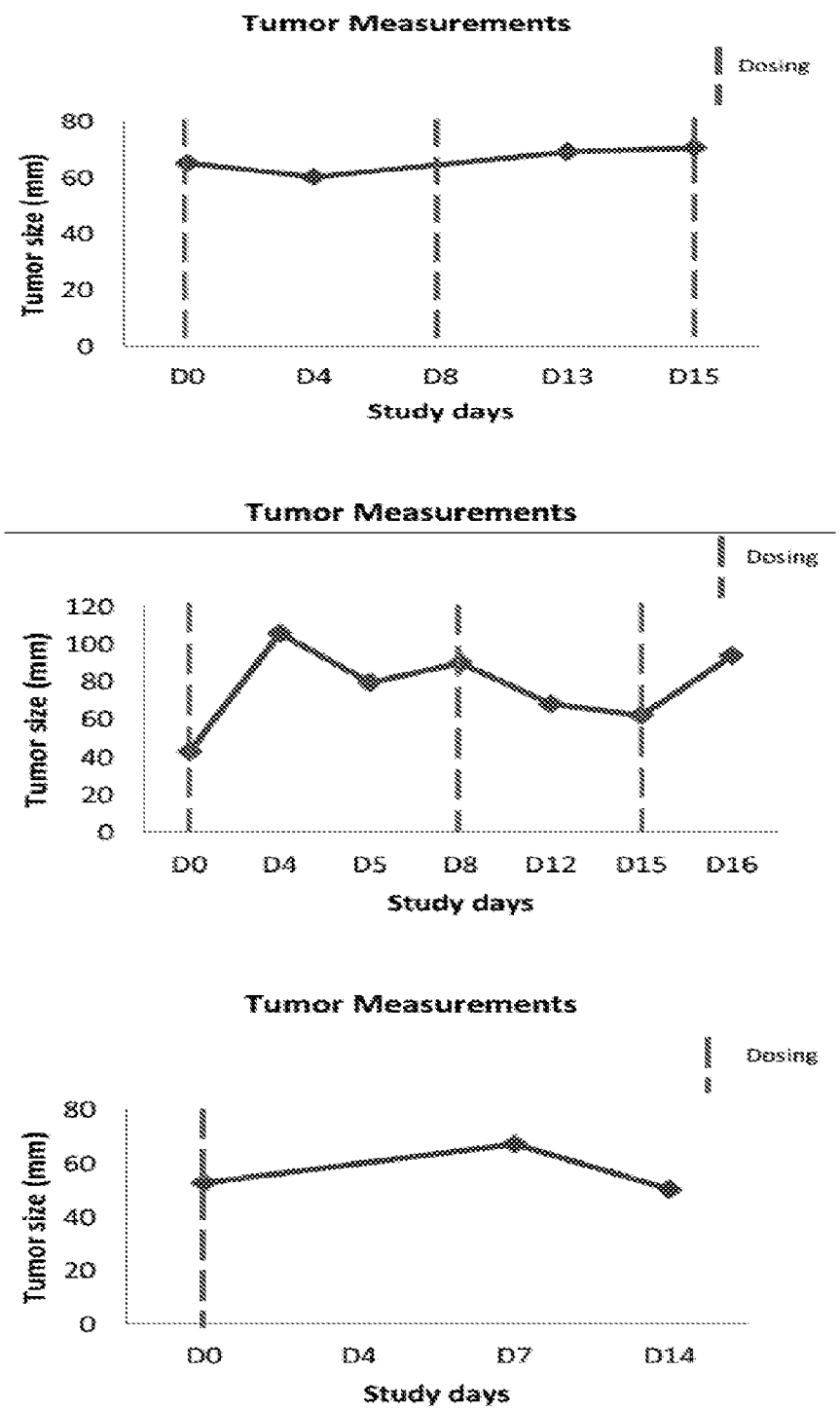

Time courses of tumor measurements from eight of the dogs are shown in FIG. 12A. FIG. 12B shows three time courses that were shortened due to amputation or data cut-off.

In summary, *C. novyi*-NT administered by IT injection at a dose of $1\times10^8$ spores per cycle with up to 4 cycles of treatment exhibits meaningful biological and anti-tumor activities and appears to be well-tolerated in companion dogs with naturally occurring solid tumors. Tumor responses are rapid, with significant tumor necrosis and notable disease regression occurring within days of *C. novyi*-NT administration. Most adverse events are limited to Grade 1 and Grade 2, and are consistent with the mechanism-based tumor inflammatory reactions expected from the *C. novyi*-NT therapeutic. Several cases are currently under long-term follow-up for assessment of progression and survival.

Example 8

Intratumoral (IT) Administration of *C. novyi*-NT—Study 2 Methods

A study characterizing dose and volume of *C. novyi*-NT administration by IT injection for the treatment of dogs with solid tumors (excluding osteosarcoma or mast cell tumor) is being performed.

Dogs with solid tumors (except osteosarcoma or mast cell tumor) of any weight, breed, sex, or age were screened for enrollment. Inclusion criteria was similar to that presented in Example 6, with the exception that each dog had a cytologic or histologic diagnosis of any cancer excluding osteosarcoma or mast cell tumor, and that each dog had at least 1 measurable tumor lesion with a longest diameter 1 cm.

During the initial screening visit each dog was assigned a unique study dog identification number consisting of a 5-digit numeric code (which may not be sequentially in order of the screening dog number). The first 2 digits indicated the study site (01 to 99), the middle digit indicated the study '5', and the last 2 digits described the study dog number within a study site (01 to 99). For example the 11th dog enrolled at Site 9 was assigned study dog number 09-511. Study dog numbers were assigned chronologically in the order that dogs were enrolled at a given study site. A dog was considered enrolled in the study when it satisfied the inclusion and exclusion criteria.

Gross pathology, histopathology, and necropsy were performed as described in Example 6.

*C. novyi*-NT spores were prepared as set forth above prior to shipment at a concentration of $1\times10^8$ spores/mL and suspended in sterile saline in 2 mL cryovials. Each cycle of *C. novyi* treatment was composed of up to 5 injections of 1 mL spore suspension ($1\times10^8$ spores) for each injection into a single target lesion. The spore suspension containing $1\times10^8$ spores was packed in individual cryovials for each 1 mL injection, and the vial, syringe, and needle were discarded after each injection.

Figure 13:
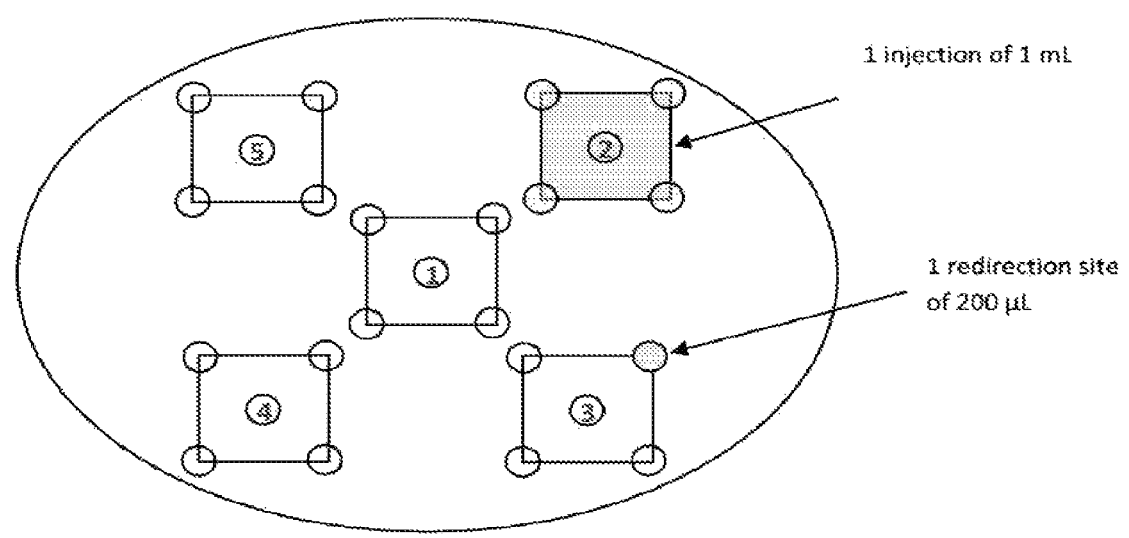

The scheme for injection is shown in FIG. 13. Five 1 mL injection sites (as represented by squares) were distributed within the tumor: center, and four (4) evenly allocated injection sites within the tumor. The site for each 1 mL injection further consisted of 5 redirection sites (as represented by circles in FIG. 13). Each redirection site received 200 μL of spore suspension. The needle was first directed within the center of the injection site, and then evenly redirected to the four corners of the injection site without withdrawing the needle. Upon the completion of the first 1 mL injection, the needle was withdrawn and the syringe was discarded. The depth of each injection should be adequately distributed such that the best distribution is achieved. The recommended size of syringe was 1 mL for each injection, the recommended needle was between 22-gauge and 25-gauge. Adequate length of needle should be selected based on the depth of the tumor lesion.

All dogs were hospitalized from DO to D2, and then at the Investigator's discretion for 24 to 48 hours after each subsequent treatment for clinical observation. Fluids were administered to all study dogs during hospitalization following *C. novyi*-NT treatment. On dosing days all dogs were administered IV crystalloids at 4 ml/hg/h for 2 hours post-treatment with *C. novyi*-NT.

Study visits and events are summarized in Table 18, as an example of an 8-cycle treatment regimen. The dosing interval was suggested to be weekly if the intent was to treat the dog with multiple cycles of therapy.

TABLE 18

Summary of study visits and events

|  | Screen D-14 to D 0 | Cycle 1* D 0 | Cycle 2-8† D_ | D 70 ± 7 days | D 90 ± 7 days |
|---|---|---|---|---|---|
| Informed consent | X | | | | |
| Demographics | X | | | | |
| Weight and vitals | X | X | X | X | X |
| Physical examination | X | X | X | X | X |
| Lab samples | X | X | (X) | (X) | X |
| Research blood samples | X | X | X | X | X |
| Research tumor sample | X | | | | |
| Diagnostic imaging | X | | | | X*** |
| Performance score | X | | | | |
| Inclusion/exclusion | X | | | | |
| Enrollment | X | | | | |
| Tumor measurement | X | X | X | X | X |
| C. novyi-NT* | | x* | x† | | |
| Crystalloids** | | x** | x** | | |
| Study completion | | | | | X†† |

*Owners will leave their dog in clinic from the D 0 until D 2, and IV crystalloids will be administered to all dogs in hospital. For subsequent cycles, Investigators will fill in the D according to the number of days on study, relative to D 0.
**Dogs will be administered IV crystalloids.
***Thoracic radiographs only.
†Dogs may not receive 8 cycles. For this study, the decision to continue subsequent cycle of dosing will be made on a case by case basis via consultation among the Medical Director, Investigator and Sponsor.
††Following study completion and if systemic antibiotics were required to manage adverse events, it is recommended to administer doxycycline 5-10 mg/kg PO BID to dogs for 3 months.

Example 9

Intratumoral (IT) Administration of C. novyi-NT—Study 2 Interim Results

As of Dec. 2, 2012, two companion dogs have been treated in the study. Both animals received a dose level of $5 \times 10^8$ spores administered at 5 unique IT injection sites per treatment cycle.

The first dog, Buddy (04-503), a 9 year-old, male neutered, Belgian malinois, presented with soft tissue sarcoma on the left carpus with a LD measurement of 69 mm at baseline (4.4×3.3×0.7 cm by CT). His treatment history included surgery prior to enrollment. He received 2 cycles of IT C. novyi-NT spores. Adverse events were mild and limited to Grade I fever and Grade I tumor inflammation. Buddy received the 1st and 2nd treatment cycles on Nov. 21, 2012 and Nov. 28, 2012. Grade I fever and tumor redness, swelling and increased pain were noted within 6 hours of the first injection. The fever resolved within 6 hours following treatment with the NSAID carprofen. Mild tumor ulceration was noted on Day 2 (Nov. 23, 2012) following treatment. At Day 7 (Nov. 28, 2012), a slight decrease in the size of the mass was noted (−12.0%). Each cycle of treatment was well tolerated with no adverse events greater than Grade I.

The second dog, Guinness (04-502), a 9 year-old, male neutered, Wheaton terrier, presented with squamous cell carcinoma on the left shoulder with a LD measurement of 122 mm at baseline (9.1×9.3×14.5 cm by CT), a low-grade hemangiosarcoma on the rear leg, and evidence of pulmonary metastasis (based on CT). His treatment history included surgery prior to enrollment. Preexisting mitral valve disease was evident based on echocardiography performed prior to enrollment. He received a single dose of IT C. novyi-NT spores on Nov. 28, 2012. Grade III fever was noted within 6 hours of treatment and medically managed with IV fluids. On Day 1 (Nov. 29, 2012), abscess of the mass, purulent discharge, and neutrophilia were appreciated. IV fluids were continued and pain medications (including NSAIDs) were started. On Day 2 (Nov. 30, 2012), progressive tumor swelling and evidence of sepsis (fever, neutropenia, hypoglycemia, hypoalbuminemia) prompted lancing of the tumor and irrigation. Broad-spectrum antibiotics, hetastarch and human albumin were administered. On Day 3 (Dec. 1, 2012), progressive decline in status was noted resulting in respiratory distress. Euthanasia solution was administered. A necropsy was performed. Gross clinically significant findings included vegetative endocarditis, suppurative lung nodules, and whole-body subcutaneous hemorrhage and edema. Postmortem aerobic cultures from various tissues and organs (lung, liver, heart, kidney, spleen, GI, stomach) revealed polymicrobial bacterial growth (*Staphylococcus aureus, Pseudomonas aeruginosa, E. coli, Streptococcus* species); anaerobic cultures from all organs and tissues were negative for C. novyi-NT growth except in the tumor tissue and urinary bladder. Histopathology of affected tissues are pending. Septic toxemia shock is considered the most likely cause of death and relationship to C. novyi-NT therapy is unknown at this time.

Example 10

Intratumoral (IT) Administration of C. novyi-NT in Humans—Methods

Phase I Human Clinical Trial of IT Injected C. novyi-NT Spores

An open-label, non-randomized, multi-center phase I safety study of a single IT injection of C. novyi-NT spores is currently ongoing in patients with treatment-refractory solid tumors. The clinical study protocol was reviewed and approved by the Institutional Review Board (IRB) of each participating institution, and all regulatory steps were performed under the guidance of the Food and Drug Administration (FDA) (number NCT01924689). All patients were required to sign a written Informed Consent Form (ICF) before inclusion in the study.

The primary objectives of this phase I study were to determine the safety profile, dose limiting toxicities (DLT), and maximum tolerated dose (MTD) of IT injected *C. novyi*-NT. In addition, the anti-tumor activity of the therapeutic was explored.

Preparation and IT Injection of *C. novyi*-NT Spores in Phase I Study

The clinical supply of *C. novyi*-NT spores was packaged in a single-use 2 mL sterile and pyrogen-free, Type I borosilicate glass vial with a rubber stopper and aluminum seal with a tamper resistant cap at a concentration of $8.52 \times 10^8$ spores/mL suspended in sterile phosphate buffered saline (PBS) with a 1.0 mL fill volume. The vials were stored between 2-8° C. in controlled temperature environment under constant temperature monitoring. The GMP product was manufactured and formulated by Omnia Biologics, Inc. (Rockville, Md.).

After a patient was enrolled in the trial, one vial was shipped to the study site. Further preparation of *C. novyi*-NT was required and occurred on the same day of the IT injection. Dilution of the concentrated spore suspension was performed in a designated biological safety cabinet using sterile saline (0.9%) infusion bags of appropriate size to achieve the required dose based on the assigned cohort. The injection volume (3 mL) was then withdrawn from the saline bag and injected under radiographic guidance. *C. novyi*-NT spores were injected with an 18-gauge multi-prong needle (Quadra-Fuse®, Rex-Medical, Conshohocken, Pa.).

Design and Conduct of Human Clinical Trial

The study was conducted with a standard 3+3 dose-escalation design. Patients must have been diagnosed as having an advanced solid tumor malignancy with a target tumor that was measureable, palpable or clearly identifiable under ultrasound or radiographic guidance and amenable to percutaneous injection of *C. novyi*-NT spores. The targeted lesion must have a longest diameter≥1 cm and be measurable as defined by RECIST 1.1 criteria. The main eligibility criteria included history of a treatment refractory malignancy; age of at least 18 years; Eastern Cooperative Oncology Group (ECOG) performance status≤2; able to stay within 45 minutes driving time of an emergency room and having a caregiver for 28 days after IT injection. The main exclusion criteria were pregnancy; primary brain malignancy or brain metastases; clinically significant ascites or clinical evidence or history of portosystemic hypertension or cirrhosis; Glasgow Coma Score (GCS)<15; serum creatinine level>1.5× the upper limit of normal (ULN), chronic renal failure requiring hemodialysis or peritoneal dialysis; oxygen saturation ($SpO_2$)<95% (room air); mean arterial blood pressure (BP)<70 mmHg; platelet count≤100,000/$mm^3$; hemoglobin<9.0 g/dL; absolute neutrophil count (ANC)<1,000/$mm^3$; clinically significant pleural effusion, pericardial effusion, circumferential pericardial effusion, or any effusion greater than 1.0 cm at any location around the heart; need to ongoing treatment with an immunosuppressive agent; history of solid organ transplantation; systemic or localized infection.

Eligible patients were admitted and enrolled into a dose cohort. Under the protocol, patients remain hospitalized after spore administration and observed for 8 days, and patients return to the clinical site for routinely scheduled follow-up visits for 12 months, during which time assessments of safety and efficacy were performed.

Clinical response and progression were evaluated using the RECIST version 1.1. Objective responses were measured by serial CT or MRI scans of the injected tumor, as well as distant metastases (up to 5 target lesions). Safety monitoring for infectious complications or other treatment-emergent adverse events were continuously conducted for 12 months.

Example 11

Intratumoral (IT) Administration of *C. novyi*-NT in Humans—Results

*C. novyi*-NT Causes Rapid Local Tumor Destruction in the First Human Patient

The promising outcomes and favorable risk/benefit profiles of biosurgery in the comparative canine trial, in conjunction with the results observed in rats, provided a rationale for attempting biosurgery in humans. Accordingly, a Phase I investigational study in human patients with solid tumors that were either refractory to standard therapy or without an available standard therapy was initiated (NCT01924689). The first patient enrolled in this trial is reported herein: a 53-year-old female diagnosed with a retroperitoneal leiomyosarcoma in August 2006. The patient underwent several surgical resections and received multiple chemotherapy and radiotherapy treatments, including a right radical nephrectomy and radiation therapy in March 2007, chemotherapy with gemcitabine, taxol, adriamycin, and ifosfamide, resection of liver metastasis in November 2008, multiple wedge resections of right-sided pulmonary metastases in December 2009, trabectedin treatment from March 2010 to April 2011, multiple wedge resection of left-sided pulmonary metastases in December 2010, pazopanib treatment in April 2011, left lower lobectomy in October 2011, HAI abraxane, gemcitabine, and avastin from February 2012 to January 2013, everolimus and pazopanib from February 2013 to July 2013, and bland arterial hepatic embolization in August 2013 and September 2013. However, the patient progressed, with metastatic disease present in her liver, lungs, peritoneum, and soft tissue in the right shoulder and adjacent right humerus.

Biosurgery was performed with the planned starting dose of $1 \times 10^4$ *C. novyi*-NT spores injected into her metastatic right shoulder tumor with an 18-gauge multi-prong needle (day 0, Nov. 19, 2013).

CT-Guided Intratumoral Injection Using a Three-Pronged Needle

Figure 16A:
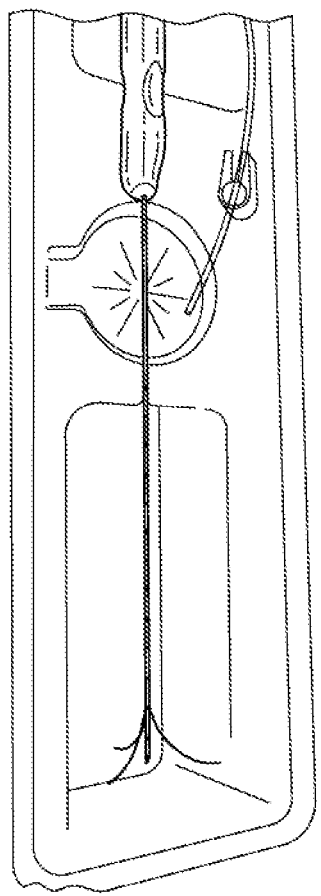
Figure 16B:
Figure 16C:
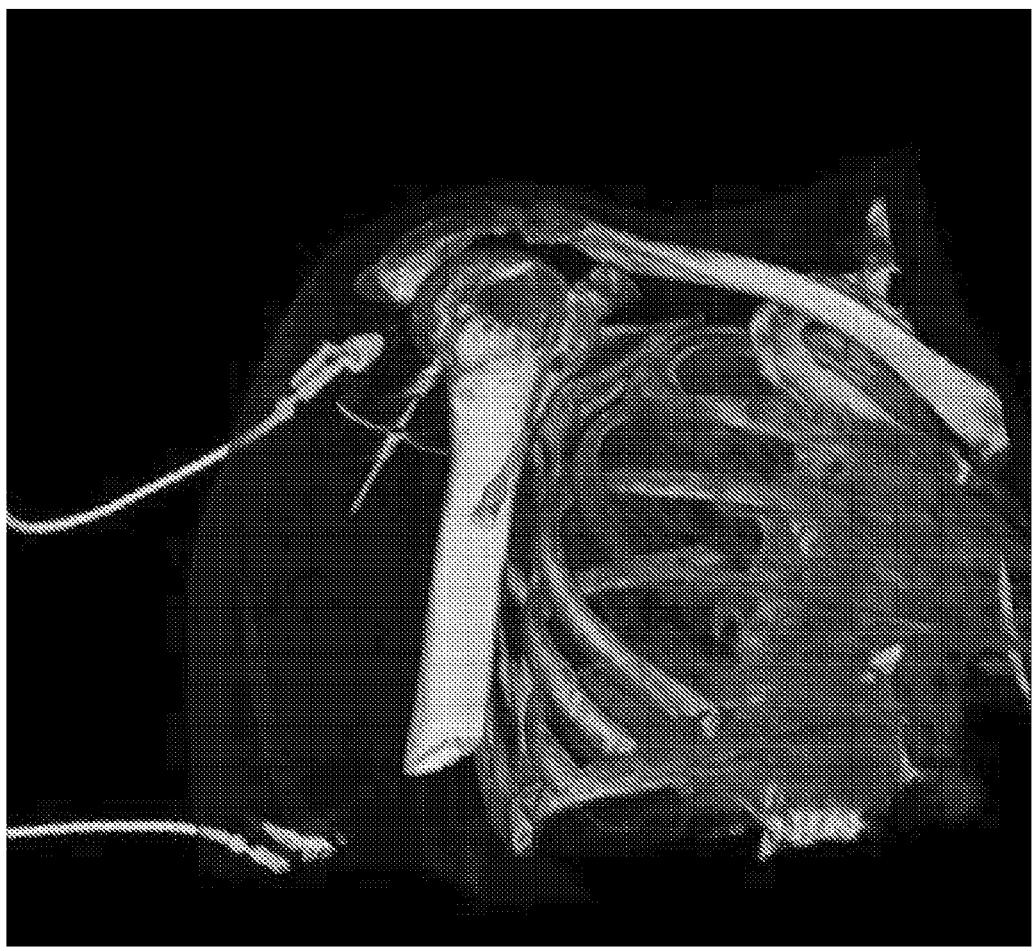
Figure 16D:
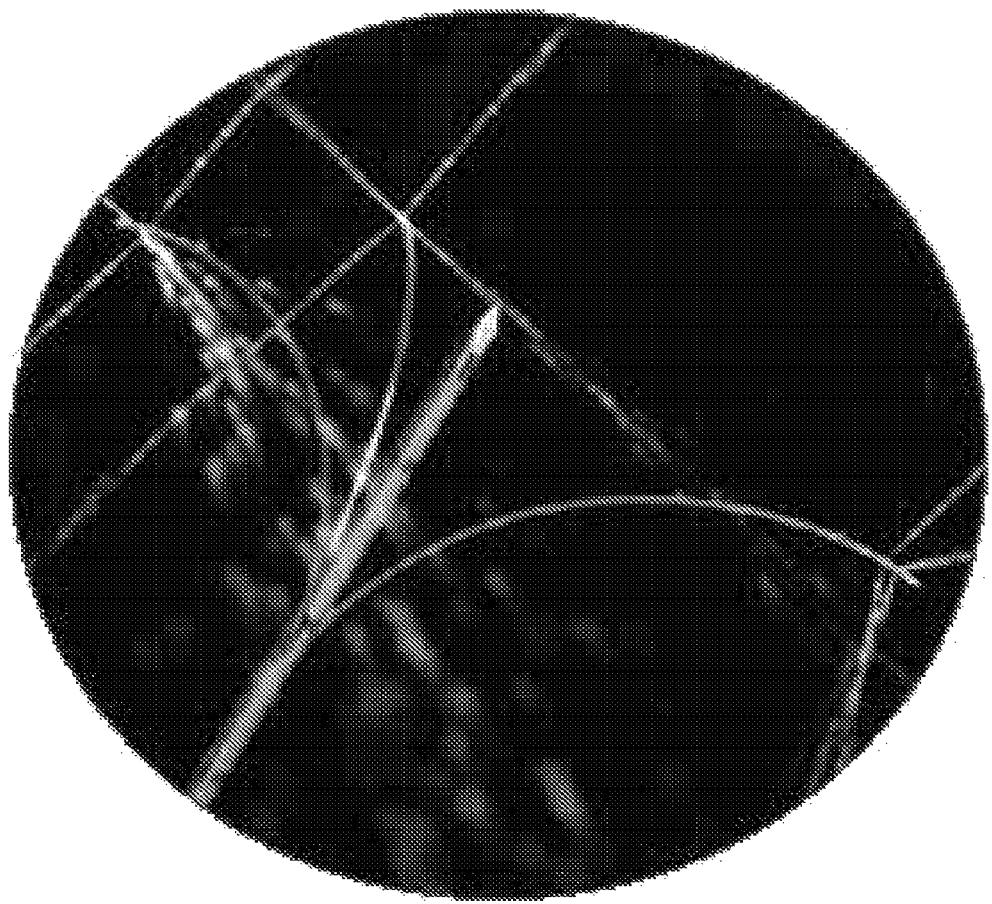
Figure 16E:
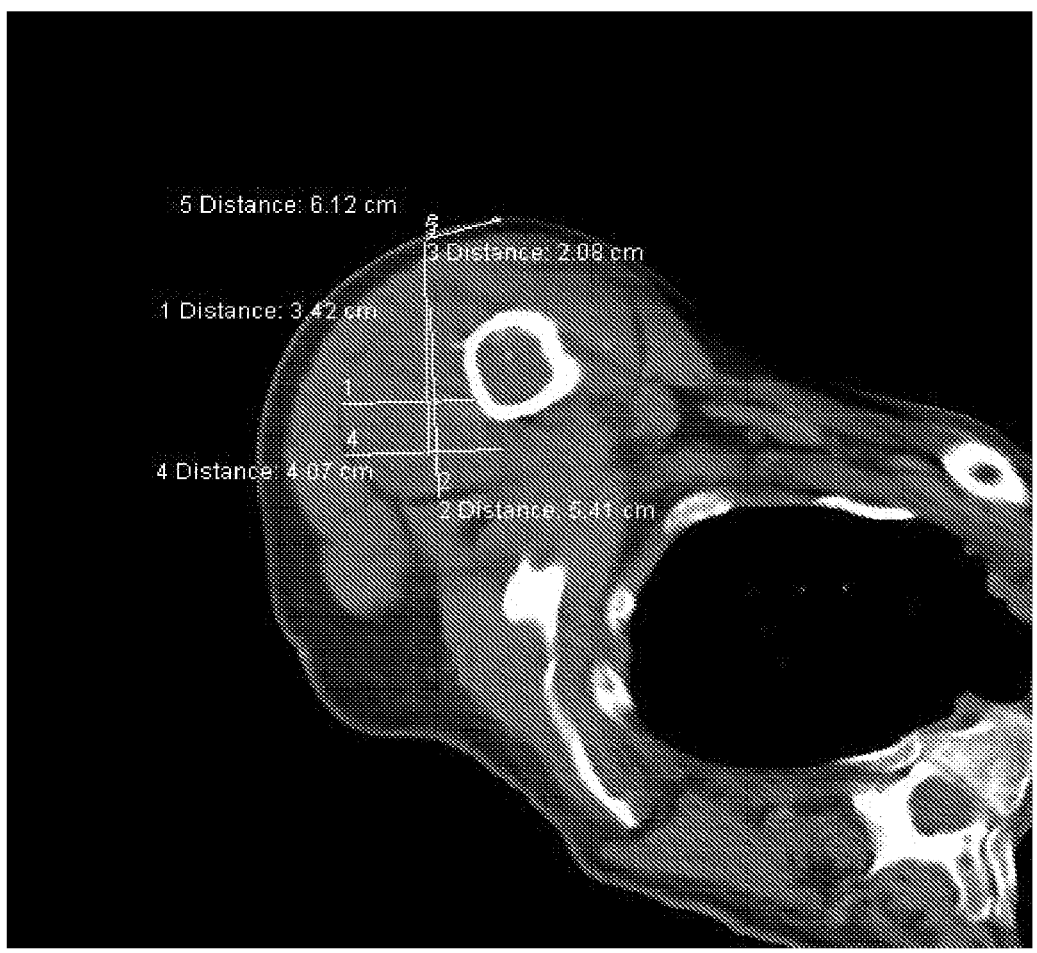

The subject was placed under moderate sedation with fentanyl and versed for 35 minutes. An 18-gauge Quadra-Fuse device (Rex Medical) (FIG. 16A) was employed for injection under CT guidance by inserting the 3-pronged needle (27 g) in the target injection area (FIGS. 16B and 16C). Three tines (each having 2 through holes, for 4 fluid exits) (FIG. 16D) were deployed at 4, 3, and 2 cm at which location (FIG. 16E), a 1 ml aliquot of *C. novyi*-NT spore solution was injected during the staged retraction process. The device was removed after the deployed tines were fully retracted into the needle cannula and manual compression was utilized to achieve hemostasis.

Figure 14A:
Figure 14B:
Figure 14C:
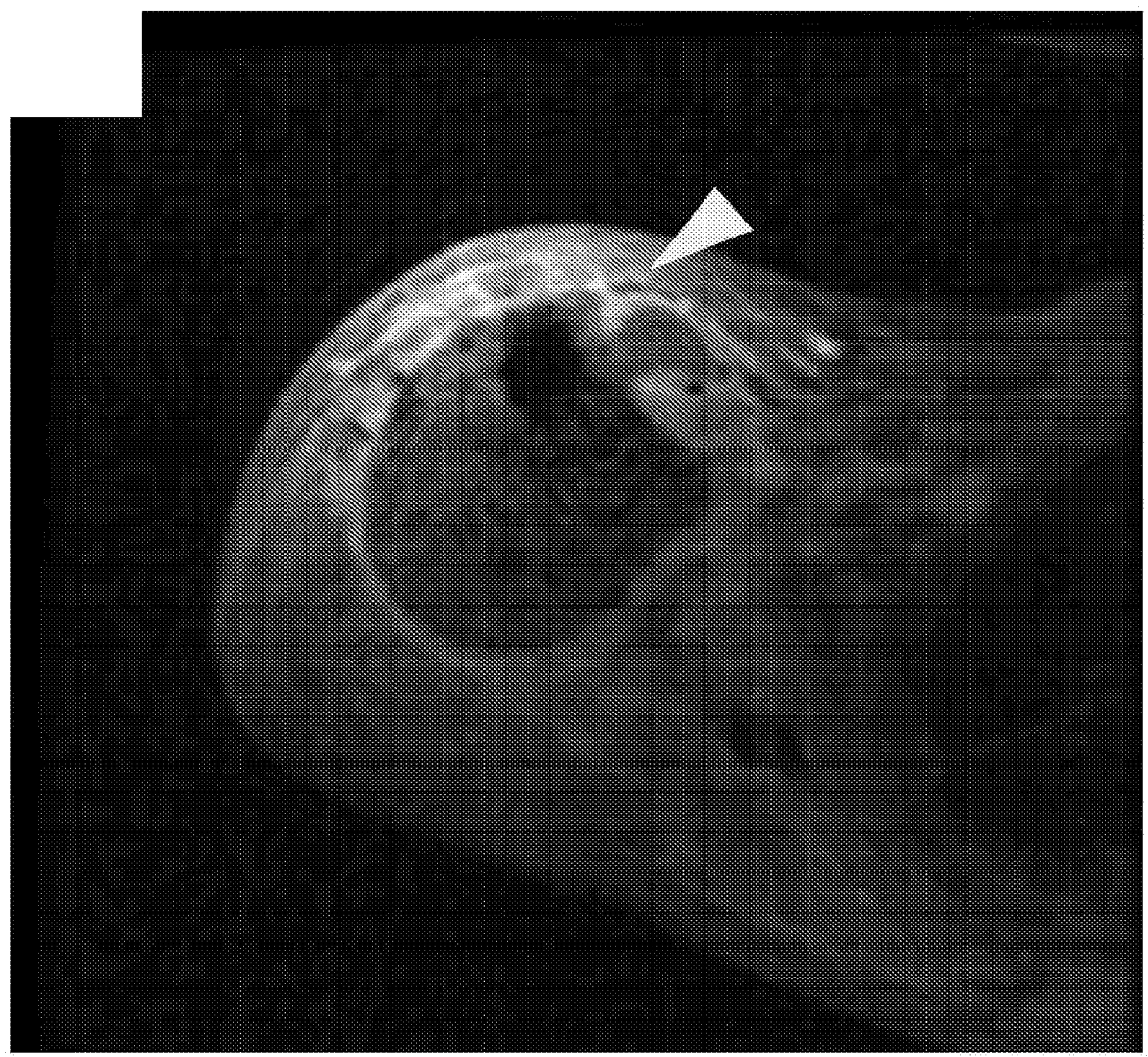
Figure 14D:
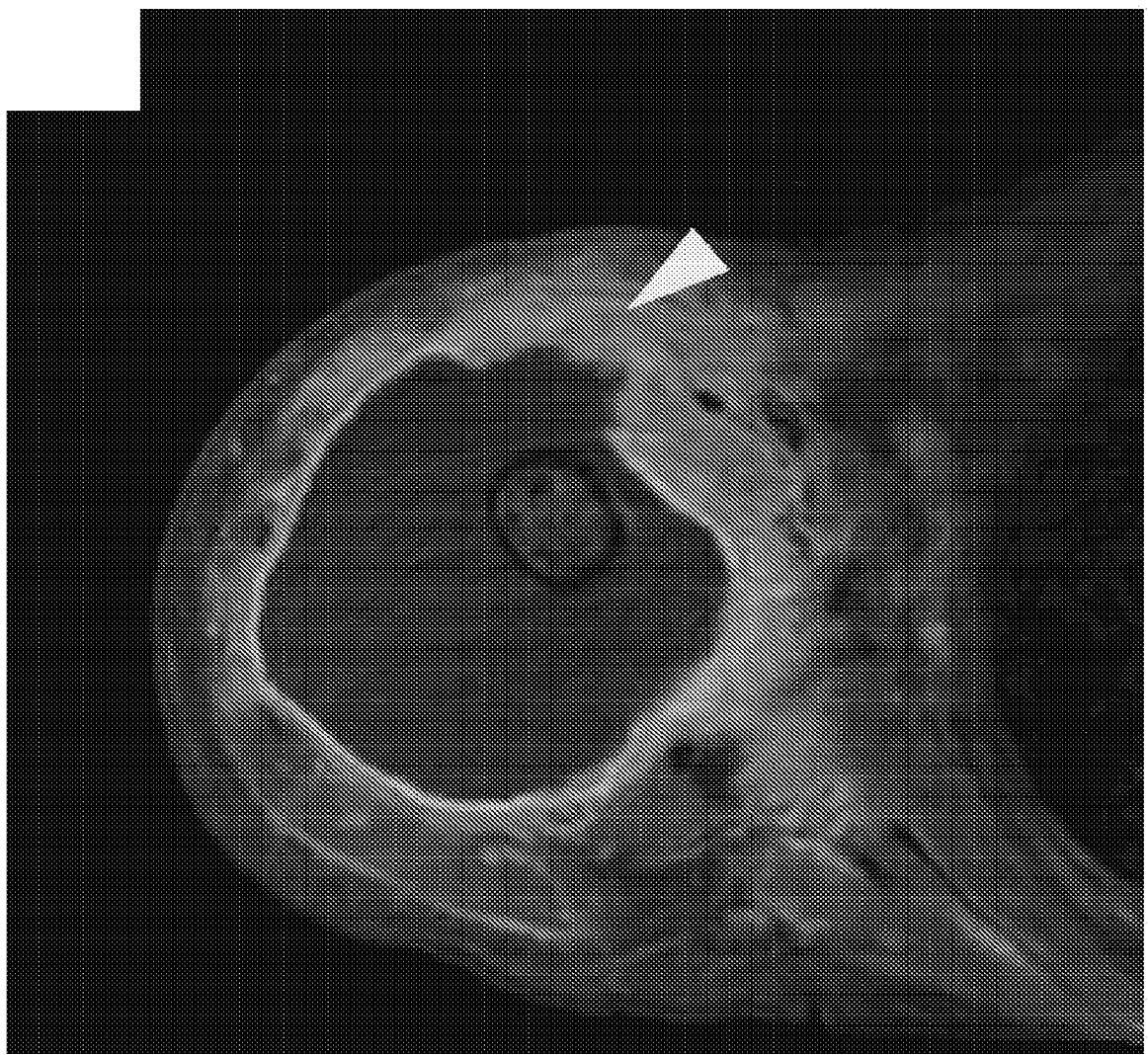
Figure 15A:
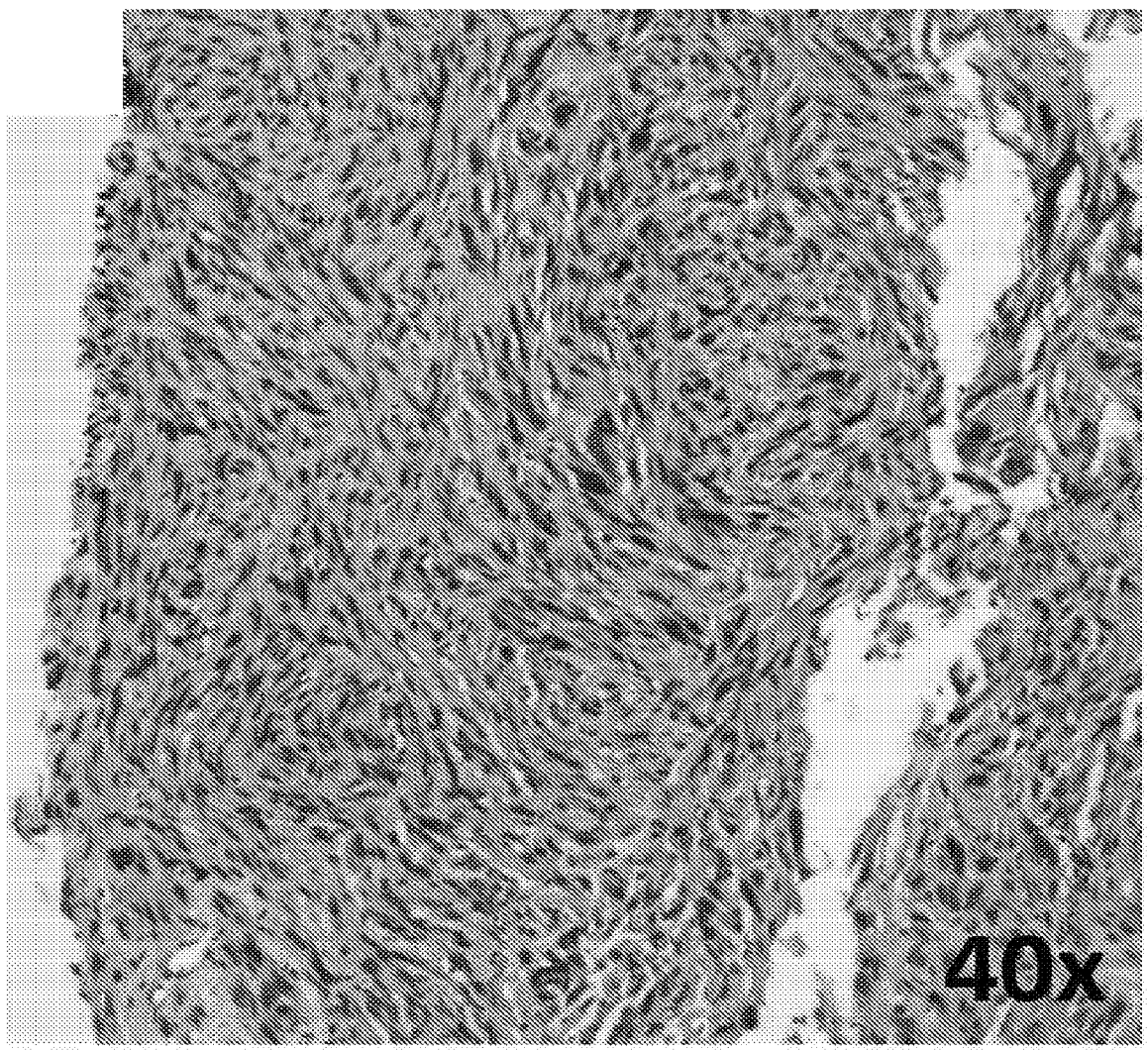
Figure 15B:
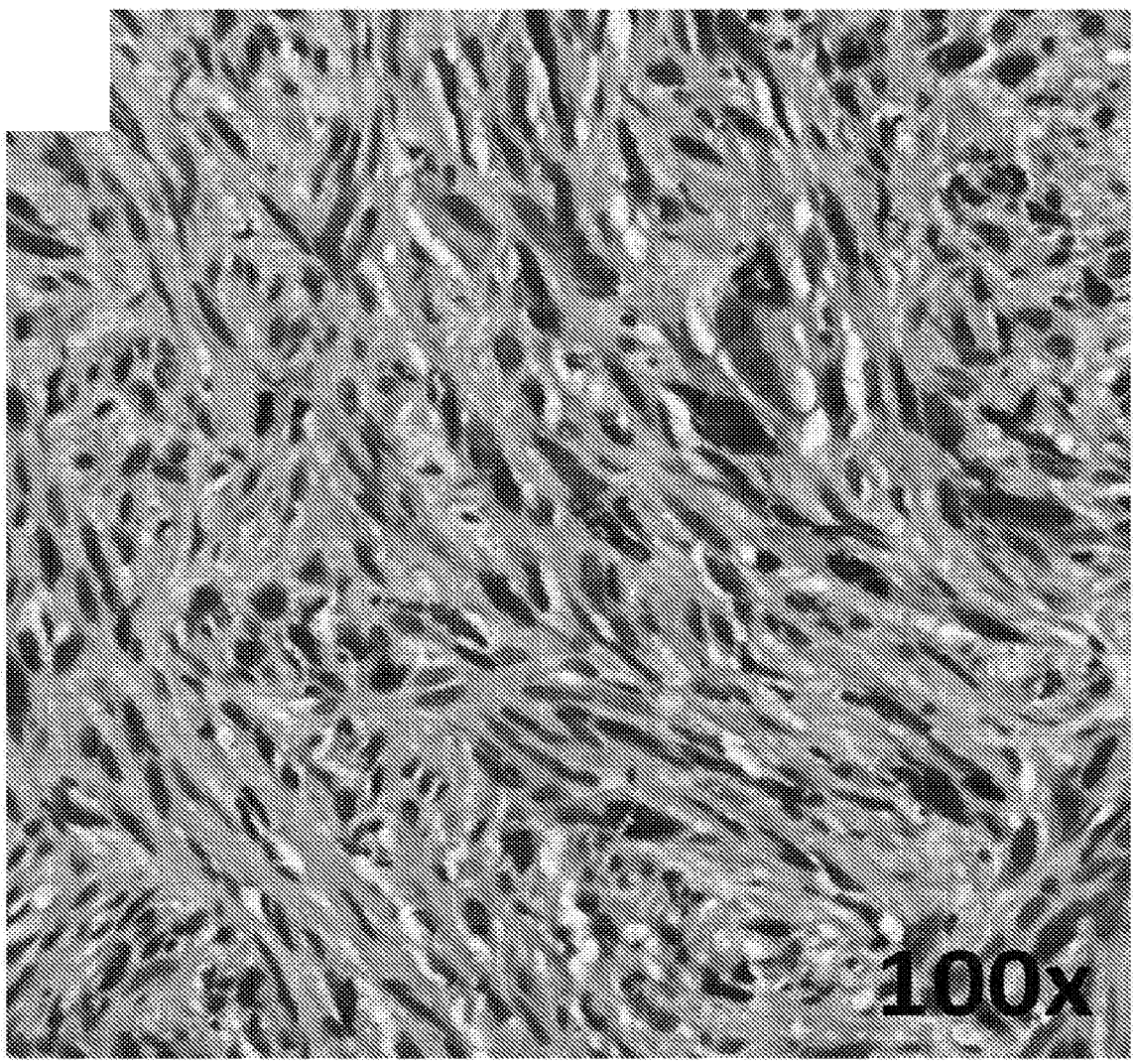
Figure 15C:
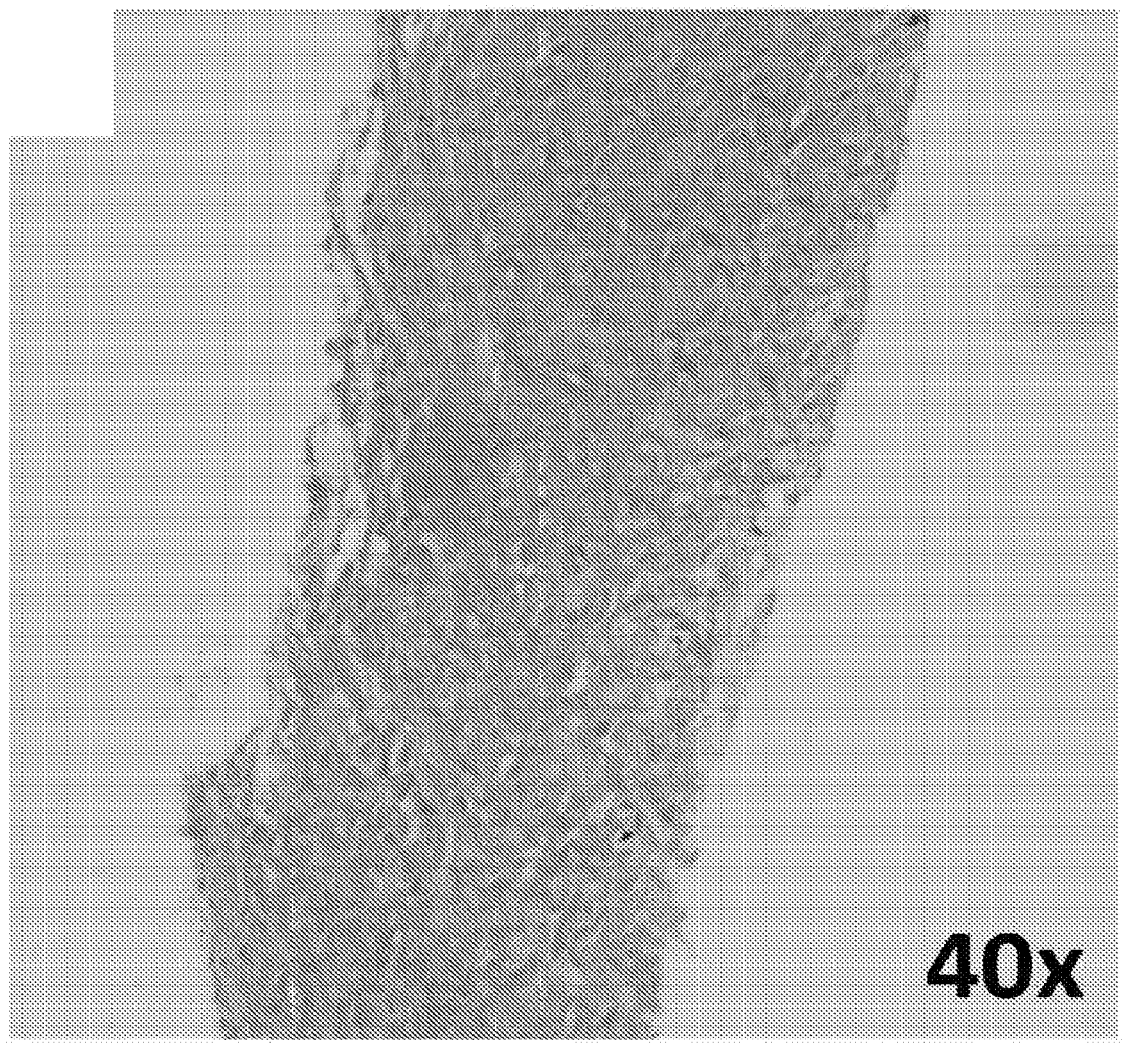
Figure 15D:
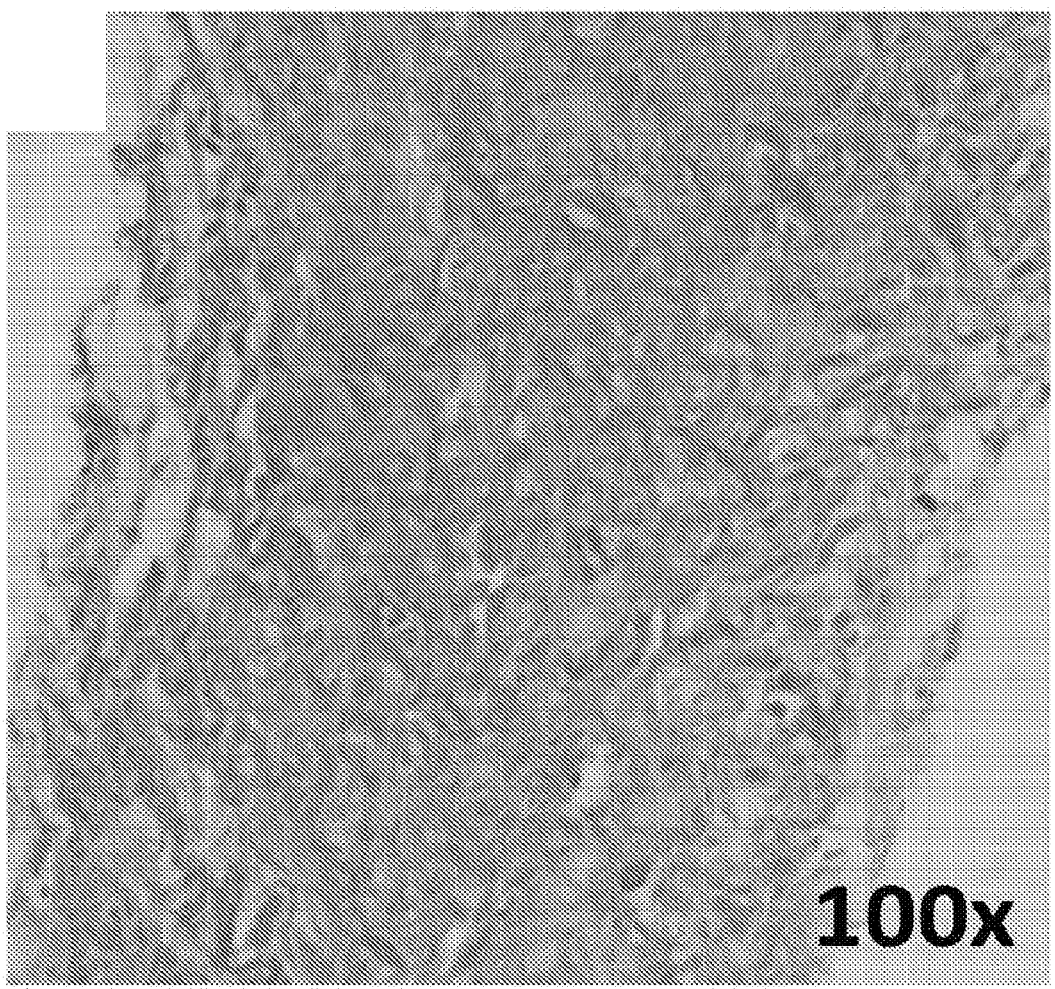

On day 1, the patient experienced mild right shoulder pain extending to the scapula, which responded to tramadol and acetaminophen. On day 2, her pain required IV patient controlled analgesia with hydromorphone, her leukocyte count increased to 18,300 per μL, and she developed fever with a maximum temperature of 39.2° C. On day 3, the pain in the patient's right shoulder and scapula was difficult to control. Her maximum temperature was 37.8° C. The CT scan of the right upper extremity demonstrated extensive tumor destruction with gas in the soft tissue and bony component of the tumor (FIG. 14A). Necrosis of her humerus was discussed. A CT-guided aspirate of her tumor revealed *C. novyi*-NT growth under anaerobic culture conditions. The patient was then started on antibiotics and defervesced shortly after. On day 4, a MRI of the right upper extremity demonstrated markedly diminished enhancement confined to the tumor mass compared to baseline (FIGS. 14B and 14C). Biopsies from the tumor showed many gram-positive bacteria and an absence of viable tumor cells. At the time of the biopsies, a percutaneous drain was placed within the tumor abscess to drain fluid and debris. The patient remained afebrile and her leukocyte count gradually normalized. She continued on antibiotics and was kept in the hospital for IV analgesia until day 20 when she was transitioned to oral analgesics. She was discharged on orally administered metronidazole and doxycycline per protocol. On day 29, a follow-up MRI demonstrated an ongoing reduction in tumor enhancement (FIG. 14D). On day 55 the patient presented with localized pain as a result of a patient-effort induced pathologic fracture of the right proximal humerus. Subsequent partial resection of the humerus, debridement, and internal fixation with an intramedullary nail and cement spacer resulted in significant improvement in pain and an increase in range of motion. Intraoperative cultures revealed *C. novyi*-NT growth under anaerobic culture conditions. Histopathology demonstrated extensive tumor necrosis with small foci of residual tumor cells. (FIGS. 15A-D). The patient continues to be monitored and has a performance status of 1 on the Eastern Cooperative Oncology Group scale (ECOG) with no clinical signs of infection.

DOCUMENTS

AGRAWAL, N. et al. Bacteriolytic therapy can generate a potent immune response against experimental tumors. Proc Natl Acad Sci USA 101, 15172-7 (2004).

BAI, R. Y., et al. V. Antiparasitic mebendazole shows survival benefit in 2 preclinical models of glioblastoma multiforme. Neuro-oncology 13, 974-982 (2011).

BARRETINA, J., et al. Subtype-specific genomic alterations define new targets for soft-tissue sarcoma therapy. Nature genetics 42, 715-721 (2010).

BETTEGOWDA, C., et al. The genome and transcriptomes of the anti-tumor agent *Clostridium novyi*-NT. Nature biotechnology 24, 1573-1580 (2006).

BREED, R. S., et al. The Number of Colonies Allowable on Satisfactory Agar Plates. Journal of Bacteriology 1 (3): 321-331 (1916).

CAREY, R. W., et al. Clostridial oncolysis in man. Eur. J. Cancer 3, 37-46 (1967).

CHMIELECKI, J., et al. Whole-exome sequencing identifies a recurrent NAB2-STAT6 fusion in solitary fibrous tumors. Nature genetics 45, 131-132 (2013).

DANG, L. H. et al. Targeting Vascular and Avascular Compartments of Tumors with *C. novyi*-NT and Anti-Microtubule Agents. Cancer Biol Ther 3, 326-37 (2004).

DANG, L. H., et al. Combination bacteriolytic therapy for the treatment of experimental tumors. PNAS. Vol. 98, pages 15155-15160 (2001).

DANG, L. H., et al. U.S. Pat. No. 7,344,710.

DENNIS, M. M., et al. Prognostic factors for cutaneous and subcutaneous soft tissue sarcomas in dogs. Veterinary pathology 48, 73-84 (2011).

DIAZ, L. A., Jr. et al. Pharmacologic and toxicologic evaluation of *C. novyi*-NT spores. Toxicol Sci 88, 562-75 (2005).

EUROPEAN MEDICINES AGENCY. Combined VeDDRA list of clinical terms for reporting suspected adverse reactions in animals and humans to veterinary medicinal products (2012).

GAVHANE, Y. N. et al. Solid Tumors: Facts, Challenges and Solutions. International J. of Pharma Science and Research, Vol. 2, pages 1-12 (2011).

JAIN, R. K., et al. Can engineered bacteria help control cancer? Proc Natl Acad Sci USA 98, 14748-50 (2001).

JONES, S., et al. Frequent mutations of chromatin remodeling gene ARID1A in ovarian clear cell carcinoma. Science 330, 228-231 (2010).

JOSEPH, C., et al. Exomic Analysis of myxoid liposarcomas, synovial sarcomas and osteosarcomas. Submitted, (2013).

LEE, R. S., et al. A remarkably simple genome underlies highly malignant pediatric rhabdoid cancers. The Journal of clinical investigation 122, 2983-2988(2012).

MOSE, J. R. *Clostridium* Strain M55 and its effect on Malignant Tumors. in Bactéries anaérobies 1st edn (ed. Fredette, V.) 229-247 (Montreal: Institut de Microbiologie et l'Hygiène de Université de Montréal, 1967).

MOSE, J. R. Onkolyse durch Clostridien. in 3rd Internationals Congress of Chemotherapy (ed. Thieme, G.) 1972 (Stuttgart, Germany, 1963).

PAOLONI, M., et al. Translation of new cancer treatments from pet dogs to humans. Nature Reviews Cancer 8, 147-156 (2008).

PARKER, R. C., et al. Effect of *histolyticus* infection and toxin on transplantable mouse tumors. Proc. Soc. Exp. Biol. Med. 66, 461 (1947).

PATNAIK, A. K., et al. Canine cutaneous mast cell tumor: morphologic grading and survival time in 83 dogs. Veterinary pathology 21, 469-474 (1984).

SABATTINI, S., et al. Histologic Grading of Canine Mast Cell Tumor: Is 2 Better Than 3? Veterinary pathology, published online Feb. 10, 2014.

SMEDLEY, R. C., et al. Prognostic markers for canine melanocytic neoplasms: a comparative review of the literature and goals for future investigation. Veterinary pathology 48, 54-72 (2011).

VAIL, D. M., et al. Spontaneously occurring tumors of companion animals as models for human cancer. Cancer investigation 18, 781-792 (2000).

VETERINARY CO-OPERATIVE ONCOLOGY GROUP. Veterinary Co-operative Oncology Group—Common Terminology Criteria for Adverse Events (VCOG-CTCAE) following chemotherapy or biological antineoplastic therapy in dogs and cats v1.0. Veterinary and comparative oncology 2, 195-213(2004).

VOGELSTEIN, B., et al. Cancer genome landscapes. Science 339, 1546-1558 (2013).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for debulking or abalating a solid tumor present in a human comprising administering intratumorally to the human a unit dose of C. novyi colony forming units (CFUs) comprising $1 \times 10^3$-$1 \times 10^6$ CFUs suspended in a pharmaceutically acceptable carrier or solution, wherein the C. novyi is effective to debulk or ablate the solid tumor without administration of additional anti-cancer agents.

2. The method according to claim 1, wherein the solid tumor is selected from the group consisting of soft tissue sarcoma, hepatocellular carcinoma, breast cancer, pancreatic cancer, and melanoma.

3. The method according to claim 1, wherein the solid tumor is leiomyosarcoma.

4. The method according to claim 3, wherein the solid tumor is retroperitoneal leiomyosarcoma.

5. The method according to claim 1, wherein the unit dose comprises about $1 \times 10^4$-$1 \times 10^6$ C. novyi CFUs.

6. The method according to claim 1, wherein the C. novyi CFUs are selected from the group consisting of vegetative and spore forms.

7. The method according to claim 1, wherein the C. novyi is C. novyi NT.

8. The method according to claim 7, wherein the unit dose comprises $1 \times 10^4$-$1 \times 10^6$ C. novyi NT spores.

9. The method according to claim 8, wherein the unit dose comprises $1 \times 10^5$-$1 \times 10^6$ C. novyi NT spores.

10. The method according to claim 1, wherein the administering step comprises injecting the unit dose at a single location into the tumor.

11. The method according to claim 1, wherein the administering step comprises injecting the unit dose at multiple unique locations into the tumor.

12. The method according to claim 1, wherein the administering step comprises injecting the unit dose at 1-5 unique locations into the tumor.

13. The method according to claim 1, wherein the administering step comprises injecting the unit dose at 5 or more unique locations into the tumor.

14. The method according to claim 1 further comprising administering a plurality of treatment cycles to the human, each treatment cycle comprising injecting one unit dose of the C. novyi CFUs into the solid tumor.

15. The method according to claim 14, wherein 2-10 treatment cycles are administered.

16. The method according to claim 14, wherein 2-4 treatment cycles are administered.

17. The method according to claim 14, wherein an interval between each treatment cycle is about 5-100 days.

18. The method according to claim 14, wherein an interval between each treatment cycle is about 7 days.

19. The method according to claim 7 further comprising administering IV fluids to the human before, during, and/or after each administration of the C. novyi NT spores.

20. The method according to claim 7 further comprising administering a plurality of treatment cycles to the human, each treatment cycle comprising injecting one unit dose of the C. novyi NT spores into the solid tumor.

21. The method according to claim 20, wherein 2-4 treatment cycles are administered.

22. The method according to claim 1 further comprising administering IV fluids to the human before, during, and/or after each administration of the C. novyi.

23. The method according to claim 1 further comprising providing the human with a first course of antibiotics for a period of time and at a dosage that is effective to treat or alleviate an adverse side effect selected from the group consisting of infections, vomiting, hematochezia, fever, and combinations thereof caused by the C. novyi.

24. The method according to claim 23, wherein the antibiotics are administered for two weeks post C. novyi administration.

25. The method according to claim 23, wherein the antibiotics are selected from the group consisting of amoxicillin, clavulanate, metronidazole, and combinations thereof.

26. The method according to claim 23 further comprising providing the human with a second course of antibiotics for a period of time and at a dosage that is effective to treat or alleviate an adverse side effect selected from the group consisting of infections, vomiting, hematochezia, fever, and combinations thereof caused by the C. novyi.

27. The method according to claim 26, wherein the second course of antibiotics is initiated after completion of the first course of antibiotics and is carried out for 1-6 months.

28. The method according to claim 26, wherein the second course of antibiotics is initiated after completion of the first course of antibiotics and is carried out for 3 months.

29. The method according to claim 26, wherein the antibiotic used in the second course is doxycycline.

30. The method according to claim 1, further comprising administering to the human an anti-cancer agent selected from the group consisting of chemotherapy, radiation therapy, immunotherapy, and combinations thereof, after the C. novyi have acted to debulk or ablate the solid tumor.

31. The method according to claim 30, wherein the immunotherapy comprises administering to the human an immune checkpoint inhibitor.

32. The method according to claim 1, wherein the solid tumor is resistant to a therapy selected from the group consisting of chemotherapy, radiation therapy, immunotherapy, and combinations thereof.

33. The method according to claim 30, wherein the chemotherapy comprises administering to the human an agent selected from the group consisting of an anti-metabolite, a microtubule inhibitor, a DNA damaging agent, an antibiotic, an anti-angiogenesis agent, a vascular disrupting agent, a molecularly targeted agent, and combinations thereof.

34. The method according to claim 30, wherein the chemotherapy comprises administering to the human an agent selected from the group consisting of gemcitabine, taxol, adriamycin, ifosfamide, trabectedin, pazopanib, abraxane, avastin, everolimus, and combinations thereof.

35. The method according to claim 1, wherein the solid tumor is refractory to standard therapy or the solid tumor is without an available standard therapy.

36. The method according to claim 1, wherein the unit dose of *C. novyi* induces a potent localized inflammatory response and an adaptive immune response in the human.

37. A method for microscopically precise excision of tumor cells in a human comprising administering intratumorally to the human a unit dose of *C. novyi* NT colony forming units (CFUs) comprising $1 \times 10^3$-$1 \times 10^6$ CFUs suspended in a pharmaceutically acceptable carrier or solution, wherein the *C. novyi* is effective for microscopically precise excision of the tumor cells without administration of additional anti-cancer agents.

38. A method for debulking or ablating a solid tumor that has metastasized to one or more sites in a human comprising administering intratumorally to the human a unit dose of *C. novyi* NT colony forming units (CFUs) comprising $1 \times 10^3$-$1 \times 10^6$ CFUs suspended in a pharmaceutically acceptable carrier or solution, wherein the *C. novyi* is effective to debulk or ablate the solid tumor without administration of additional anti-cancer agents.

39. The method according to claim 38, wherein at least one site is distal to the original solid tumor.

40. A method for debulking a solid tumor present in a human comprising administering intratumorally to the human a unit dose of *C. novyi* CFUs comprising $1 \times 10^3$-$1 \times 10^6$ CFUs suspended in a pharmaceutically acceptable carrier or solution, wherein the *C. novyi* is effective to debulk the solid tumor without administration of additional anti-cancer agents.

41. The method according to claim 40, wherein the solid tumor is selected from the group consisting of soft tissue sarcoma, hepatocellular carcinoma, breast cancer, pancreatic cancer, and melanoma.

42. A method for debulking a solid tumor present in a human comprising administering intratumorally to the human one to four cycles of a unit dose of *C. novyi* NT spores comprising $1 \times 10^3$-$1 \times 10^6$ spores per cycle, each unit dose of *C. novyi* NT being suspended in a pharmaceutically acceptable carrier or solution, wherein the *C. novyi* is effective to debulk the solid tumor without administration of additional anti-cancer agents.

43. A method for debulking or ablating a solid tumor present in a human comprising administering intratumorally to the human one to four cycles of a unit dose of *C. novyi* NT spores comprising $1 \times 10^3$-$1 \times 10^6$ spores per cycle, each unit dose of *C. novyi* NT spores being suspended in a pharmaceutically acceptable carrier or solution, wherein the *C. novyi* is effective to debulk or ablate the solid tumor without administration of additional anti-cancer agents.

44. A method for ablating a solid tumor present in a human comprising administering intratumorally to the human a unit dose of *C. novyi* CFUs comprising $1 \times 10^3$-$1 \times 10^6$ CFUs suspended in a pharmaceutically acceptable carrier or solution, wherein the *C. novyi* is effective to ablate the solid tumor without administration of additional anti-cancer agents leaving a margin of normal tissue.

45. The method according to claim 44, wherein the tumor is a sarcoma.

\* \* \* \* \*

SEQUENCE LISTING

<160> NUMBER OF SEQ ID NOS: 170

<210> SEQ ID NO 1
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 1
ccctanctgg g    11

<210> SEQ ID NO 2
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 2
aaaacntcca g    11

<210> SEQ ID NO 3
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 3
ggtcantatt a    11

<210> SEQ ID NO 4
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 4
aggagngacg c    11

<210> SEQ ID NO 5
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 5
gcccgngatg g					11

<210> SEQ ID NO 6
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 6
cgcacncacc t					11

<210> SEQ ID NO 7
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 7
ttaccncaat c					11

<210> SEQ ID NO 8
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 8
aacaangtca t					11

<210> SEQ ID NO 9
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 9
ccgtgntgag t					11

<210> SEQ ID NO 10
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

```
<400> SEQUENCE: 10
acaagncggc c                                                                11

<210> SEQ ID NO 11
<211> LENGTH: 11
<212> TYPE: DNA
<213> ORGANISM: Artificial Sequence
<220> FEATURE:
<223> OTHER INFORMATION: mutation site

<400> SEQUENCE: 11
atctgcggtt c                                                                11

<210> SEQ ID NO 12
<211> LENGTH: 11
<212> TYPE: DNA
<213> ORGANISM: Artificial Sequence
<220> FEATURE:
<223> OTHER INFORMATION: mutation site

<400> SEQUENCE: 12
gattcggaag t                                                                11

<210> SEQ ID NO 13
<211> LENGTH: 11
<212> TYPE: DNA
<213> ORGANISM: Artificial Sequence
<220> FEATURE:
<223> OTHER INFORMATION: mutation site

<400> SEQUENCE: 13
acctactttg a                                                                11

<210> SEQ ID NO 14
<211> LENGTH: 11
<212> TYPE: DNA
<213> ORGANISM: Artificial Sequence
<220> FEATURE:
<223> OTHER INFORMATION: mutation site

<400> SEQUENCE: 14
tgtcacactc a                                                                11

<210> SEQ ID NO 15
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 15
aagcanagca c                                                                11

<210> SEQ ID NO 16
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t
```

<400> SEQUENCE: 16
agttgntgga c                                                               11

<210> SEQ ID NO 17
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 17
cctgangaat t                                                               11

<210> SEQ ID NO 18
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 18
tcttgnagaa g                                                               11

<210> SEQ ID NO 19
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 19
acccanagat g                                                               11

<210> SEQ ID NO 20
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 20
ctgggnctta c                                                               11

<210> SEQ ID NO 21
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)

```
<223> OTHER INFORMATION: n is a, c, g, or t

<400> SEQUENCE: 21
aggtanagca g                                                          11

<210> SEQ ID NO 22
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 22
atcgangtca a                                                          11

<210> SEQ ID NO 23
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 23
gctgtngctg c                                                          11

<210> SEQ ID NO 24
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 24
agacangccc c                                                          11

<210> SEQ ID NO 25
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 25
cggtcnccca g                                                          11

<210> SEQ ID NO 26
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
```

```
<222> LOCATION: (6)..(6)
<223> OTHER INFORMATION: n is a, c, g, or t

<400> SEQUENCE: 26
gaaggncttc t                                                            11

<210> SEQ ID NO 27
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 27
aggcgngcac a                                                            11

<210> SEQ ID NO 28
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 28
gaagantttg g                                                            11

<210> SEQ ID NO 29
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 29
tttggnttta t                                                            11

<210> SEQ ID NO 30
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 30
ttcggnggcg g                                                            11

<210> SEQ ID NO 31
<211> LENGTH: 11
<212> TYPE: DNA
<213> ORGANISM: Artificial Sequence
<220> FEATURE:
<223> OTHER INFORMATION: mutation site
<220> FEATURE:
```

<221> NAME/KEY: misc_feature
<222> LOCATION: (6)..(6)
<223> OTHER INFORMATION: n is a, c, g, or t

<400> SEQUENCE: 31
cccccncagt g                                                          11

<210> SEQ ID NO 32
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 32
tttttnctcg g                                                          11

<210> SEQ ID NO 33
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 33
ccaccngctc a                                                          11

<210> SEQ ID NO 34
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 34
attacngcag c                                                          11

<210> SEQ ID NO 35
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 35
atcacnccgg a                                                          11

<210> SEQ ID NO 36
<211> LENGTH: 11
<212> TYPE: DNA
<213> ORGANISM: Artificial Sequence
<220> FEATURE:
<223> OTHER INFORMATION: mutation site

```
<220> FEATURE:
<221> NAME/KEY: misc_feature
<222> LOCATION: (6)..(6)
<223> OTHER INFORMATION: n is a, c, g, or t

<400> SEQUENCE: 36
gacatnctct a                                                          11

<210> SEQ ID NO 37
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 37
aatgcnacca g                                                          11

<210> SEQ ID NO 38
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 38
cagctngccc a                                                          11

<210> SEQ ID NO 39
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 39
gggggncagg c                                                          11

<210> SEQ ID NO 40
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 40
cacttnagga a                                                          11

<210> SEQ ID NO 41
<211> LENGTH: 11
<212> TYPE: DNA
<213> ORGANISM: Artificial Sequence
<220> FEATURE:
```

```
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 41
gggctncttc c                                                               11

<210> SEQ ID NO 42
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 42
tgatantact a                                                               11

<210> SEQ ID NO 43
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 43
ctcctngtct c                                                               11

<210> SEQ ID NO 44
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 44
ttcaancatg t                                                               11

<210> SEQ ID NO 45
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 45
catttntttg c                                                               11

<210> SEQ ID NO 46
<211> LENGTH: 11
<212> TYPE: DNA
<213> ORGANISM: Artificial Sequence
```

```
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 46
aatgtncgtg c                                                          11

<210> SEQ ID NO 47
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 47
ggcccnccat g                                                          11

<210> SEQ ID NO 48
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 48
attttnggga c                                                          11

<210> SEQ ID NO 49
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 49
agatgnccca t                                                          11

<210> SEQ ID NO 50
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 50
aactcnctgc g                                                          11

<210> SEQ ID NO 51
<211> LENGTH: 11
<212> TYPE: DNA
```

```
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 51
attttnttga a                                                              11

<210> SEQ ID NO 52
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 52
aaccancctt c                                                              11

<210> SEQ ID NO 53
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 53
tcagangcag a                                                              11

<210> SEQ ID NO 54
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 54
agaaanccct c                                                              11

<210> SEQ ID NO 55
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 55
tgcatngaca t                                                              11

<210> SEQ ID NO 56
<211> LENGTH: 11
```

```
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 56
agtggngccg g                                                        11

<210> SEQ ID NO 57
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 57
tcattnttcg g                                                        11

<210> SEQ ID NO 58
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 58
tctggnaatg g                                                        11

<210> SEQ ID NO 59
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 59
gacttngccc a                                                        11

<210> SEQ ID NO 60
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 60
gttttncttc t                                                        11

<210> SEQ ID NO 61
```

```
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 61
attgtncaag a                                                    11

<210> SEQ ID NO 62
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 62
ggctgntgaa g                                                    11

<210> SEQ ID NO 63
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 63
ggtganagtc c                                                    11

<210> SEQ ID NO 64
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 64
ggctgnccag a                                                    11

<210> SEQ ID NO 65
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 65
cggggncccg g                                                    11
```

```
<210> SEQ ID NO 66
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 66
ccaagnaaat t                                                          11

<210> SEQ ID NO 67
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 67
aaattnccta c                                                          11

<210> SEQ ID NO 68
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 68
tgcacnaagc t                                                          11

<210> SEQ ID NO 69
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 69
tttggnaatc a                                                          11

<210> SEQ ID NO 70
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 70
tctcancata g                                                          11
```

<210> SEQ ID NO 71
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 71
aatttncata g                                                              11

<210> SEQ ID NO 72
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 72
aagganggag g                                                              11

<210> SEQ ID NO 73
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 73
attttnattt t                                                              11

<210> SEQ ID NO 74
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 74
cctccnctgt g                                                              11

<210> SEQ ID NO 75
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 75
gctgtntgga g                                                              11

-continued

```
<210> SEQ ID NO 76
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 76
agactnatct c                                                        11

<210> SEQ ID NO 77
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 77
gggaanagaa g                                                        11

<210> SEQ ID NO 78
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 78
cttccngctt g                                                        11

<210> SEQ ID NO 79
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 79
aatacnaaca a                                                        11

<210> SEQ ID NO 80
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 80
```
tgttgnatgt t                                                            11

<210> SEQ ID NO 81
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 81
tgtcgnagcg c                                                            11

<210> SEQ ID NO 82
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 82
gtgccngtcc a                                                            11

<210> SEQ ID NO 83
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 83
gatccngtct c                                                            11

<210> SEQ ID NO 84
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 84
cgactncccc a                                                            11

<210> SEQ ID NO 85
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 85
tggtcnagct a                                                             11

<210> SEQ ID NO 86
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 86
ccgagntcat g                                                             11

<210> SEQ ID NO 87
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 87
ctgtcnaatg t                                                             11

<210> SEQ ID NO 88
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 88
ccacgnagtc a                                                             11

<210> SEQ ID NO 89
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 89
gttctnaact a                                                             11

<210> SEQ ID NO 90
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

```
<400> SEQUENCE: 90
gggagnagaa a                                                          11

<210> SEQ ID NO 91
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 91
aaaatnatgc a                                                          11

<210> SEQ ID NO 92
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 92
taaacnatca g                                                          11

<210> SEQ ID NO 93
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 93
ggcatnatgg c                                                          11

<210> SEQ ID NO 94
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 94
caattngcca g                                                          11

<210> SEQ ID NO 95
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t
```

<400> SEQUENCE: 95
ttttgnaaat t                                                                    11

<210> SEQ ID NO 96
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 96
cacttnggag c                                                                    11

<210> SEQ ID NO 97
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 97
cttctngagg g                                                                    11

<210> SEQ ID NO 98
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 98
gatttnctct g                                                                    11

<210> SEQ ID NO 99
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 99
ctactngtga g                                                                    11

<210> SEQ ID NO 100
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)

```
<223> OTHER INFORMATION: n is a, c, g, or t

<400> SEQUENCE: 100
gttcanctca a                                                                11

<210> SEQ ID NO 101
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 101
gacatnaaat t                                                                11

<210> SEQ ID NO 102
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 102
gatttncaag t                                                                11

<210> SEQ ID NO 103
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 103
tggganatgt c                                                                11

<210> SEQ ID NO 104
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 104
acttanttta t                                                                11

<210> SEQ ID NO 105
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
```

```
<222> LOCATION: (6)..(6)
<223> OTHER INFORMATION: n is a, c, g, or t

<400> SEQUENCE: 105
tcactnagtt g                                                          11

<210> SEQ ID NO 106
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 106
ggacgncagc g                                                          11

<210> SEQ ID NO 107
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 107
tttttncgtc t                                                          11

<210> SEQ ID NO 108
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 108
taaacntgca c                                                          11

<210> SEQ ID NO 109
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 109
aactcntcaa c                                                          11

<210> SEQ ID NO 110
<211> LENGTH: 11
<212> TYPE: DNA
<213> ORGANISM: Artificial Sequence
<220> FEATURE:
<223> OTHER INFORMATION: mutation site
<220> FEATURE:
```

```
<221> NAME/KEY: misc_feature
<222> LOCATION: (6)..(6)
<223> OTHER INFORMATION: n is a, c, g, or t

<400> SEQUENCE: 110
ccagcnacag c                                                              11

<210> SEQ ID NO 111
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 111
gaaatnttat a                                                              11

<210> SEQ ID NO 112
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 112
ggtccnccgg c                                                              11

<210> SEQ ID NO 113
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 113
aatcanaaag a                                                              11

<210> SEQ ID NO 114
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 114
gccatnatct g                                                              11

<210> SEQ ID NO 115
<211> LENGTH: 11
<212> TYPE: DNA
<213> ORGANISM: Artificial Sequence
<220> FEATURE:
<223> OTHER INFORMATION: mutation site
```

```
<220> FEATURE:
<221> NAME/KEY: misc_feature
<222> LOCATION: (6)..(6)
<223> OTHER INFORMATION: n is a, c, g, or t

<400> SEQUENCE: 115
tcttcnaagc a                                                                11

<210> SEQ ID NO 116
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 116
gtcttngggt g                                                                11

<210> SEQ ID NO 117
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 117
agtttncata g                                                                11

<210> SEQ ID NO 118
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 118
ttgatnaaca t                                                                11

<210> SEQ ID NO 119
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 119
cttttnataa t                                                                11

<210> SEQ ID NO 120
<211> LENGTH: 11
<212> TYPE: DNA
<213> ORGANISM: Artificial Sequence
<220> FEATURE:
```

```
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 120
tgactntctt g                                                              11

<210> SEQ ID NO 121
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 121
ggatgntctt a                                                              11

<210> SEQ ID NO 122
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 122
agggcnaagt t                                                              11

<210> SEQ ID NO 123
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 123
gcatcncctc a                                                              11

<210> SEQ ID NO 124
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 124
cgtttnttac a                                                              11

<210> SEQ ID NO 125
<211> LENGTH: 11
<212> TYPE: DNA
<213> ORGANISM: Artificial Sequence
```

```
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 125
tggganaggc g                                                          11

<210> SEQ ID NO 126
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 126
actttnttta a                                                          11

<210> SEQ ID NO 127
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 127
gaccgnttcg c                                                          11

<210> SEQ ID NO 128
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 128
gttttntgca t                                                          11

<210> SEQ ID NO 129
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 129
gttctngtga c                                                          11

<210> SEQ ID NO 130
<211> LENGTH: 11
<212> TYPE: DNA
```

```
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 130
gggagnaaaa a                                                              11

<210> SEQ ID NO 131
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 131
tgtggncttg t                                                              11

<210> SEQ ID NO 132
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 132
cggccngagg c                                                              11

<210> SEQ ID NO 133
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 133
tggacncggg c                                                              11

<210> SEQ ID NO 134
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 134
tcttcntctc c                                                              11

<210> SEQ ID NO 135
<211> LENGTH: 11
```

```
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 135
gggtgntttt t                                                           11

<210> SEQ ID NO 136
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 136
aaaggnctgg a                                                           11

<210> SEQ ID NO 137
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 137
aagatnatgt a                                                           11

<210> SEQ ID NO 138
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 138
cctcanagct g                                                           11

<210> SEQ ID NO 139
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 139
ctcggnggct c                                                           11

<210> SEQ ID NO 140
```

```
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 140
cattcnctct t                                                            11

<210> SEQ ID NO 141
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 141
tctttntgct g                                                            11

<210> SEQ ID NO 142
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 142
aactgntata a                                                            11

<210> SEQ ID NO 143
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 143
tttcantttt g                                                            11

<210> SEQ ID NO 144
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 144
tccagnccag t                                                            11
```

```
<210> SEQ ID NO 145
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 145
gagagncggg g                                                          11

<210> SEQ ID NO 146
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 146
gtgcangtgg g                                                          11

<210> SEQ ID NO 147
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 147
agggcnaccc g                                                          11

<210> SEQ ID NO 148
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 148
ccttcncctt t                                                          11

<210> SEQ ID NO 149
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 149
caggangccc c                                                          11
```

```
<210> SEQ ID NO 150
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 150
cagggngaat g                                                          11

<210> SEQ ID NO 151
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 151
tggccncctg c                                                          11

<210> SEQ ID NO 152
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 152
ctgatnctgc c                                                          11

<210> SEQ ID NO 153
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 153
cagcanaggc c                                                          11

<210> SEQ ID NO 154
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 154
tgggcntggc c                                                          11
```

<210> SEQ ID NO 155
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 155
tcaggnggca c                                                          11

<210> SEQ ID NO 156
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 156
ccacanctcc c                                                          11

<210> SEQ ID NO 157
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 157
ccgagntgcc g                                                          11

<210> SEQ ID NO 158
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 158
ctgtancttc g                                                          11

<210> SEQ ID NO 159
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 159
gctccnatga g                                                              11

<210> SEQ ID NO 160
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 160
actcgntgat g                                                              11

<210> SEQ ID NO 161
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 161
aaagtngggg g                                                              11

<210> SEQ ID NO 162
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 162
ggaaanaaga c                                                              11

<210> SEQ ID NO 163
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 163
acaggncgta g                                                              11

<210> SEQ ID NO 164
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 164
ggcagntgcg g                                                               11

<210> SEQ ID NO 165
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 165
ccccgnctcc t                                                               11

<210> SEQ ID NO 166
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 166
actgcnacaa c                                                               11

<210> SEQ ID NO 167
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 167
ccctgnagga g                                                               11

<210> SEQ ID NO 168
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 168
ggaaanctac t                                                               11

<210> SEQ ID NO 169
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

```
<400> SEQUENCE: 169
catgantgtc c                                                    11

<210> SEQ ID NO 170
<211> LENGTH: 11
<212> TYPE: DNA
<213> ORGANISM: Artificial Sequence
<220> FEATURE:
<223> OTHER INFORMATION: mutation site
<220> FEATURE:
<221> NAME/KEY: misc_feature
<222> LOCATION: (6)..(6)
<223> OTHER INFORMATION: n is a, c, g, or t

<400> SEQUENCE: 170
cttcgntcaa g                                                    11
```